US008521275B2

(12) United States Patent
Stadler et al.

(10) Patent No.: US 8,521,275 B2
(45) Date of Patent: Aug. 27, 2013

(54) METHOD OF DUAL EGM SENSING AND HEART RATE ESTIMATION IN IMPLANTED CARDIAC DEVICES

(75) Inventors: Robert W. Stadler, Shoreview, MN (US); Carissa Lynn Bellardine Black, Medford, MA (US)

(73) Assignee: Medtronic, Inc., Minneapolis, MN (US)

( * ) Notice: Subject to any disclaimer, the term of this patent is extended or adjusted under 35 U.S.C. 154(b) by 226 days.

(21) Appl. No.: 13/080,820

(22) Filed: Apr. 6, 2011

(65) Prior Publication Data

US 2011/0270334 A1    Nov. 3, 2011

Related U.S. Application Data

(60) Provisional application No. 61/328,744, filed on Apr. 28, 2010.

(51) Int. Cl.
*A61N 1/00*   (2006.01)
*A61B 5/02*   (2006.01)
*A61B 5/04*   (2006.01)

(52) U.S. Cl.
USPC .............................. 607/4; 600/508; 600/509

(58) Field of Classification Search
USPC ...................................... 600/508–509; 607/4
See application file for complete search history.

(56) References Cited

U.S. PATENT DOCUMENTS

| 5,193,535 | A | 3/1993 | Bardy |
| 5,251,626 | A | 10/1993 | Nickolls |
| 5,545,185 | A | 8/1996 | Denker |
| 5,766,227 | A | 6/1998 | Nappholz |
| 6,058,328 | A | 5/2000 | Levine |
| 6,181,966 | B1 | 1/2001 | Nigam |
| 6,301,503 | B1 | 10/2001 | Hsu |
| 6,321,115 | B1 | 11/2001 | Mouchawar |
| 6,393,316 | B1 | 5/2002 | Gillberg |
| 6,449,503 | B1 | 9/2002 | Hsu |
| 6,754,528 | B2 | 6/2004 | Bardy |
| 7,010,347 | B2 | 3/2006 | Schecter |
| 7,027,856 | B2 | 4/2006 | Zhou |
| 7,031,764 | B2 | 4/2006 | Schwartz |
| 7,039,461 | B1 | 5/2006 | Lovett |
| 7,177,683 | B2 | 2/2007 | Belk |
| 7,200,435 | B2 | 4/2007 | Ricci |
| 7,236,828 | B2 | 6/2007 | Casavant |

(Continued)

OTHER PUBLICATIONS (PCT/US2011/031875) PCT Notification of Transmittal of the International Search Report and the Written Opinion of the International Searching Authority, Mailed Sep. 9, 2011, 11 pages.

(Continued)

*Primary Examiner* — Nicole F Lavert
(74) *Attorney, Agent, or Firm* — Michael C. Soldner

(57) ABSTRACT

A method and apparatus for monitoring a patient's heart rate sense first cardiac events in a heart chamber using a first cardiac electrode pair and sense second cardiac events in the heart chamber using a second cardiac electrode pair. The method includes estimating a first heart rate using the first cardiac events, comparing the first heart rate to a heart rate threshold and estimating a second heart rate using the second cardiac events in response to the first heart rate exceeding the heart rate threshold, determining whether the second cardiac events are unreliable, and setting the second heart rate equal to the first heart rate in response to the second cardiac events being unreliable.

23 Claims, 25 Drawing Sheets

(56) References Cited

U.S. PATENT DOCUMENTS

| | | |
|---|---|---|
| 7,283,863 B2 | 10/2007 | Gunderson |
| 7,353,060 B2 | 4/2008 | Sun |
| 7,353,062 B2 | 4/2008 | Kim |
| 7,369,890 B2 | 5/2008 | Lovett |
| 7,369,893 B2 | 5/2008 | Gunderson |
| 7,474,916 B2 | 1/2009 | Gutierrez |
| 7,567,835 B2 | 7/2009 | Gunderson |
| 7,650,182 B2 | 1/2010 | Kim |
| 2002/0058878 A1 | 5/2002 | Kohler |
| 2002/0087091 A1 | 7/2002 | Koyrakh |
| 2003/0083587 A1 | 5/2003 | Ferek-Petric |
| 2004/0093035 A1 | 5/2004 | Schwartz et al. |
| 2006/0052830 A1 | 3/2006 | Spinelli |
| 2006/0095083 A1* | 5/2006 | Zhang et al. .............. 607/14 |
| 2006/0217621 A1 | 9/2006 | Kim et al. |
| 2007/0038253 A1 | 2/2007 | Kim et al. |
| 2007/0135848 A1 | 6/2007 | Kim |
| 2007/0197928 A1 | 8/2007 | Kim |
| 2007/0232944 A1 | 10/2007 | Ghanem |
| 2007/0239048 A1 | 10/2007 | Ghanem |

OTHER PUBLICATIONS (PCT/US2011/031876) PCT Notification of Transmittal of the International Search Report and the Written Opinion of the International Searching Authority, Mailed Sep. 9, 2011, 11 pages.

* cited by examiner

METHOD OF DUAL EGM SENSING AND HEART RATE ESTIMATION IN IMPLANTED CARDIAC DEVICES

REFERENCE TO RELATED APPLICATIONS

The present non-provisional U.S. Patent Application claims the benefit of U.S. Patent Application 61/328,744, filed provisionally on Apr. 28, 2010, and entitled "METHOD OF DUAL EGM SENSING AND HEART RATE ESTIMATION IN IMPLANTED CARDIAC DEVICES", incorporated by herein by reference in it's entirety.

TECHNICAL FIELD

The disclosure relates generally to implantable medical devices and, in particular, to a method and apparatus for discriminating supraventricular tachycardia (SVT) from ventricular tachycardia (VT).

BACKGROUND

A typical implantable cardioverter defibrillator (ICD) has the capability of providing a variety of anti-tachycardia pacing (ATP) regimens as well as cardioversion/defibrillation shock therapy. Normally, arrhythmia therapies are applied according to a pre-programmed sequence of less aggressive to more aggressive therapies depending on the type of arrhythmia detected. Typically, termination of an arrhythmia is confirmed by a return to either a demand-paced rhythm or a sinus rhythm in which successive spontaneous R-waves are separated by at least a defined interval. When ATP attempts fail to terminate the tachycardia, high-voltage cardioversion shocks may be delivered. Since shocks can be painful to the patient and consume relatively greater battery charge than pacing pulses, it is desirable to avoid the need to deliver shocks by successfully terminating the tachycardia using less aggressive pacing therapies.

The success of a tachycardia therapy depends in part on the accuracy of the tachycardia detection. In some cases, a tachycardia originating in the atria, i.e. a supraventricular tachycardia (SVT), is difficult to distinguish from a tachycardia originating in the ventricles, i.e. a ventricular tachycardia (VT). For example, both the atrial chambers and the ventricular chambers may exhibit a similar tachycardia cycle length when an SVT is conducted to the ventricles or when a VT is conducted retrograde to the atria. Accordingly, methods are needed for accurately classifying a detected tachycardia as VT or SVT to allow the most appropriate therapy to be delivered by the ICD, with the highest likelihood of success and without unacceptably delaying attempts at terminating the tachycardia.

DETAILED DESCRIPTION

Figure 1:
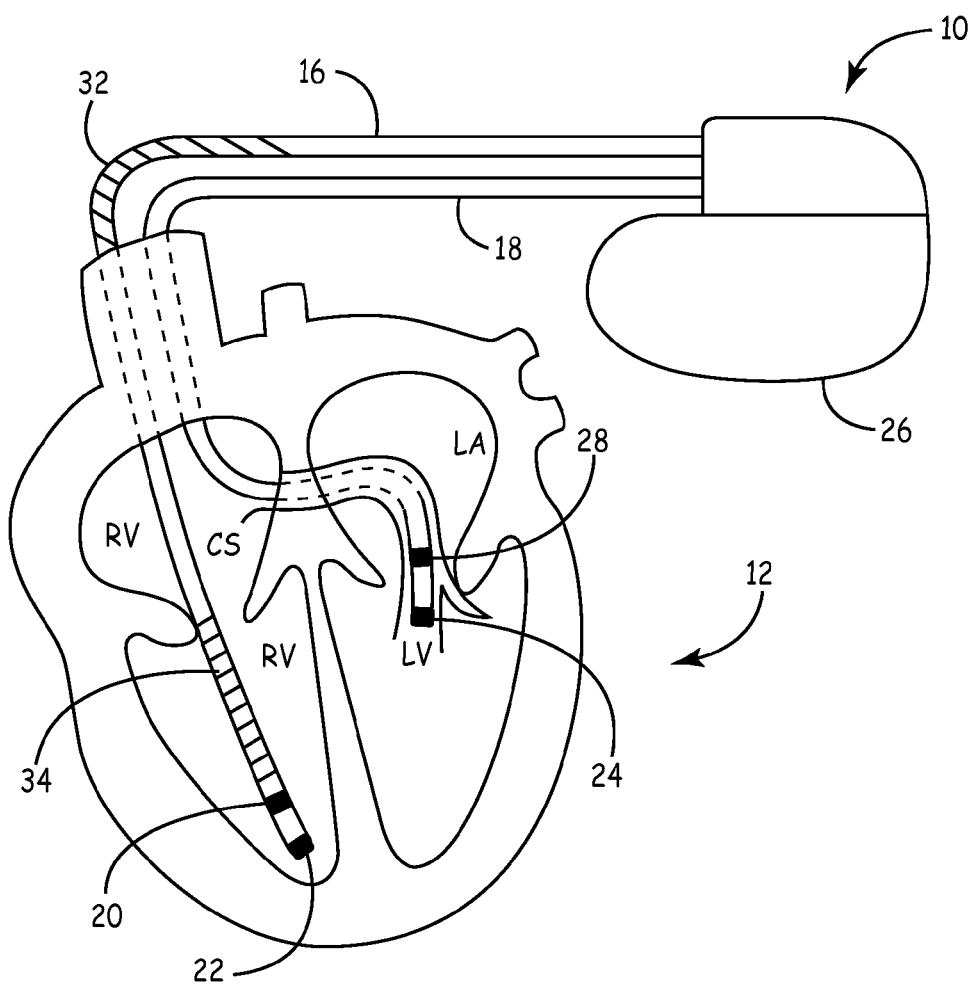
FIG. 1 is a schematic representation of an implantable medical device (IMD) 10.

In the following description, references are made to illustrative embodiments. It is understood that other embodiments may be utilized without departing from the scope of the disclosure. In some instances, for purposes of clarity, identical reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

A tachycardia detection algorithm for detecting and discriminating between treatable and non-treatable rhythms is disclosed. The term "treatable rhythm", as used herein, refers to any tachycardia that is ventricular in origin and can potentially be treated by delivering a therapy in the ventricles for terminating the ventricular tachycardia such as anti-tachycardia pacing or ventricular cardioversion or defibrillation shocks. A "non-treatable" rhythm is any rhythm with a relatively slow ventricular rate (below a ventricular tachycardia rate) and any tachycardia that is supraventricular in origin. Delivering a therapy only in the ventricular chambers frequently does not resolve a supraventricular tachycardia.

As used herein, a "concerning rhythm" is any heart rhythm that meets criteria to transition from an unconcerned detection state to a concerned detection state for detecting a potentially treatable rhythm. The criteria for transitioning to a concerned detection state may vary between embodiments but typically includes detecting rhythms that are either a fast enough ventricular rate to potentially be a treatable tachycardia or rhythms that have a sudden change in the heart rhythm that could be associated with VT, e.g. an abrupt increase in the ventricular rate or an abrupt decrease in RR interval (RRI) variability.

VT refers inclusively to any fast ventricular rhythm meeting detection criteria as described herein and does not exclude ventricular fibrillation unless explicitly stated. In the illustrative embodiment described herein, the detection algorithm relies on various heart rate limits for detecting and discriminating VT and SVT. A "detection lower limit" is the heart rate (or associated RRI) below which a treatable tachycardia can not be detected. The ventricular rate must be faster than the detection lower rate limit (or the RRI shorter than the detection lower limit interval) in order to detect a treatable rhythm. An SVT limit is the heart rate above which the rhythm is classified as a VT and is identified as a treatable rhythm. A ventricular rate faster than the SVT rate limit (or RRIs shorter than the SVT limit interval) is considered to be too fast to be supraventricular in origin. For example, in one embodiment a nominal value for the detection lower limit interval is approximately 400 ms and a nominal value of the SVT limit interval is approximately 240 ms.

FIG. 1 is a schematic representation of an implantable medical device (IMD) 10. IMD 10 is embodied as an ICD in FIG. 1. Methods described herein, however, should not be interpreted as being limited to any particular implantable medical device or any particular cardiac medical device. Instead, embodiments may include any cardiac medical device so long as the device utilizes a plurality of electrodes or other sensors for monitoring the cardiac rhythm of a patient. The electrodes are capable of sensing cardiac EGM or ECG signals, referred to herein collectively as "cardiac signals".

In FIG. 1, the right atrium (RA), left atrium (LA), right ventricle (RV), left ventricle (LV), and the coronary sinus (CS), extending from the opening in the right atrium to form the great cardiac vein, are shown schematically in heart 12. Two transvenous leads 16 and 18 connect IMD 10 with the RV and the LV, respectively. Each lead includes at least one electrical conductor and pace/sense electrode. For example, leads 16 and 18 are respectively connected to pace/sense electrodes 20, 22, and 24, 28. In addition, a housing electrode 26 can be formed as part of the outer surface of the housing of the device 10. The pace/sense electrodes 20, 22, and 24, 28 and housing electrode 26 can be selectively employed to provide a number of unipolar and bipolar pace/sense electrode combinations for pacing and sensing functions. The depicted positions in or about the right and left heart chambers are merely illustrative. Moreover, other leads and pace/sense electrodes can be used instead of, or in combination with, any one or more of the depicted leads and electrodes.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes in programmed or default combinations for sensing cardiac signals and delivering pace pulses. The leads and electrodes described can be employed to record cardiac signals. The recorded data can be periodically transmitted to a programmer or other external device enabled for telemetric communication with the IMD 10.

An RV coil electrode 34 and a superior vena cava (SVC) coil electrode 32 are also shown as being coupled to a portion of RV lead 16. Coil electrodes can additionally or alternatively be coupled to portions CS lead 18. The coil electrodes 32 and 34, or other similar electrode types, can be electrically coupled to high voltage circuitry for delivering high voltage cardioversion/defibrillation shock pulses.

Electrodes shown in FIG. 1 can be disposed in a variety of locations in, around, and on the heart and are not limited to the locations shown. Furthermore, other lead and electrode systems may be substituted for the system shown in FIG. 1. The detection algorithm described herein does not require the use of electrodes for sensing atrial signals for detecting and discriminating treatable rhythms. As such, IMD 10 is shown coupled only to ventricular leads 16 and 18 but implementation of the detection algorithm is not limited to systems employing only ventricular leads. In other embodiments, dual chamber or multi-chamber systems may be used which include atrial leads used to position electrodes in, on or around the atrial chambers.

ICDs and pacemakers typically use a single ventricular EGM signal for sensing ventricular events (R-waves) for determining a need for pacing and for detecting a RR intervals meeting tachycardia detection criteria. An EGM sensing vector may be a unipolar or bipolar sensing vector using one or two electrodes, respectively, placed in or on the ventricular heart chambers. Sensing errors that may occur on a single ventricular EGM signal may result in unneeded therapies being delivered by the ICD. Typical sensing errors that may occur include oversensing of T-waves, electromagnetic interference, non-cardiac myopotential noise, lead-related artifact, or other non-physiologic noise and double sensing of a single QRS complex. Sensing errors, including undersensing of true depolarizations and oversensing of T-waves, may also occur as a result of delivering pacing energy from the same electrodes that are used for sensing.

A rule-based tachycardia detection algorithm described herein employs simultaneous dual-vector EGM sensing for use in estimating a heart rate and for applying rules on a beat-by-beat basis to accumulate evidence of VT for the detection of treatable rhythms. One sensing vector is selected to provide an EGM signal having a relatively global EGM signal, also referred to herein as the far-field (FF) signal in that at least one of the sensing electrodes is placed away from the ventricular chambers to obtain a signal representing the spatial summation of action potential signals as they occur over a larger area of the ventricles. The second sensing vector is selected to provide an EGM signal having a relatively more local EGM signal, also referred to herein as the near-field (NF) signal in that both electrodes are located in or on a ventricular chamber to obtain a more local ventricular EGM signal.

In the illustrative embodiment shown in FIG. 1, a FF signal may be obtained by using any of the electrodes 20, 22, 24, 28, and 34 located within or on the ventricles paired with any electrode located away from the ventricles, such as SVC coil electrode 32 or the housing electrode 26. A near field signal may be obtained by selecting any two of the electrodes 20, 22, 24, 28 and 34 located within the ventricles in a bipolar pair. For example, a NF EGM signal may be sensed between the RV tip electrode 22 and the RV ring electrode 20. A FF EGM signal may be sensed simultaneously with the NF EGM signal using the RV coil electrode 34 and the housing electrode 26.

It is desirable to sense the FF and NF EGM signals using two distinct sensing vectors that do not share a common electrode. Depending on the electrode and lead configuration used, however, some embodiments may employ a common electrode between the two simultaneously sensed EGM signals. The tachycardia detection algorithm described herein refers to the use of a FF EGM signal and a NF EGM signal, however, in alternative embodiments any two distinct sensing vectors, with or without a common electrode, may be used, including any combination of at least two FF signals, at least two NF signals, or a combination including one FF and one NF signal.

Embodiments described herein are not limited to use with intracardiac or transvenous leads. Subcutaneously implanted electrodes or even external electrode systems may be used. In these cases, a "near-field" signal may be obtained by bipoles spaced more closely together than a second pair of electrodes separated by a relatively greater distance for obtaining a "far-field" signal.

Figure 2:
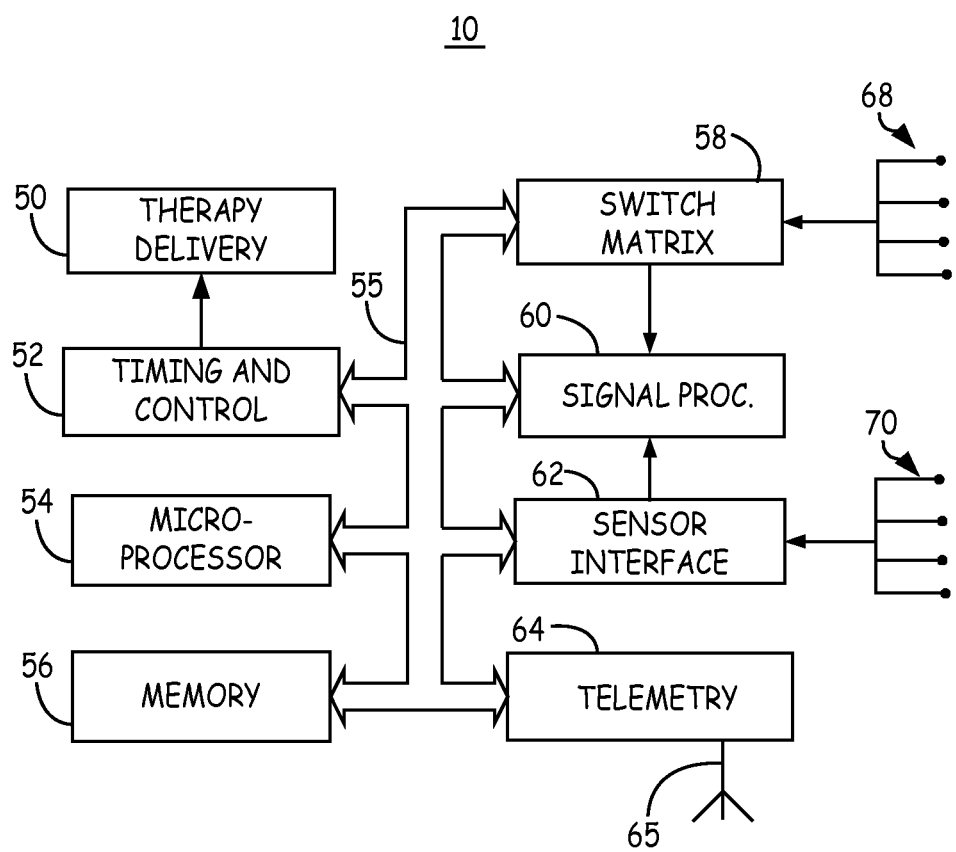
FIG. 2 is a functional block diagram of the IMD shown in FIG. 1 according to one embodiment.

FIG. 2 is a functional block diagram of the IMD 10 shown in FIG. 1 according to one embodiment. IMD 10 generally includes timing and control circuitry 52 and a controller that may be embodied as a microprocessor 54 or a digital state machine for timing sensing and therapy delivery functions in accordance with a programmed operating mode. Microprocessor 54 and associated memory 56 are coupled to the various components of IMD 10 via a data/address bus 55. IMD 10 includes therapy delivery module 50 for delivering electrical stimulation pulses to a patient's heart including cardiac pacing pulses, arrhythmia pacing therapies such as anti-tachycardia pacing (ATP) and cardioversion/defibrillation shocks, under the control of timing and control 52 and microprocessor 54. Therapy delivery module 50 is typically coupled to two or more electrodes 68 via an optional switch matrix 58. Electrodes 68 correspond to the various electrodes shown in FIG. 1. Switch matrix 58 is used for selecting which electrodes and corresponding polarities are used for delivering electrical stimulation pulses.

Cardiac electrical signals are sensed for determining when an electrical stimulation therapy is needed and in controlling the timing of stimulation pulses. Electrodes used for sensing and electrodes used for stimulation may be selected via switch matrix 58. When used for sensing, cardiac signals received by electrodes 68 are coupled to signal processing circuitry 60 via switch matrix 58. Signal processor 60 includes sense amplifiers and may include other signal conditioning circuitry such as filters and an analog-to-digital converter. Cardiac electrical signals may then be used by microprocessor 54 for detecting physiological events, such as detecting and discriminating cardiac arrhythmias. Signal processing circuitry 60 includes cardiac event sensing circuitry for sensing ventricular events, i.e. R-waves, for use in determining RRIs and QRS waveform morphology.

A tachycardia detection algorithm is implemented by the IMD controller for detecting and discriminating treatable and non-treatable rhythms. Sensed ventricular event intervals (RRIs) and R-wave morphology are used in detecting and discriminating VT from SVT. A determination as to whether the heart rhythm is a treatable rhythm can be made based on ventricular EGM signals without requiring the use of atrial signals.

In response to detecting a treatable rhythm, a therapy is delivered by therapy delivery module 50 under the control of timing and control 52. The therapy may be delivered according to a programmed menu of therapies. Arrhythmia therapies may include a menu of tiered therapies in which less aggressive ATP regimens are delivered first and, when not successful, a high voltage shock therapy is delivered.

IMD 10 may additionally be coupled to one or more physiological sensors 70 carried by leads extending from IMD 10 or incorporated in or on the IMD housing. Signals from sensors 70 are received by a sensor interface 62 which provides sensor signals to signal processing circuitry 60. Sensor signals may be used by microprocessor 54 for detecting physiological events or conditions.

The operating system includes associated memory 56 for storing a variety of programmed parameter values that are used by microprocessor 54. The memory 56 may also be used for storing data compiled from sensed EGM/ECG and other physiological signals and/or relating to device operating history for telemetry out on receipt of a retrieval or interrogation instruction. Parameters and tachycardia discrimination rules and algorithms may be stored in memory 56 and utilized by microprocessor 54.

IMD 10 further includes telemetry circuitry 64 and antenna 65. Programming commands or data are transmitted during uplink or downlink telemetry between ICD telemetry circuitry 64 and external telemetry circuitry included in a programmer or monitoring unit.

Figure 3:
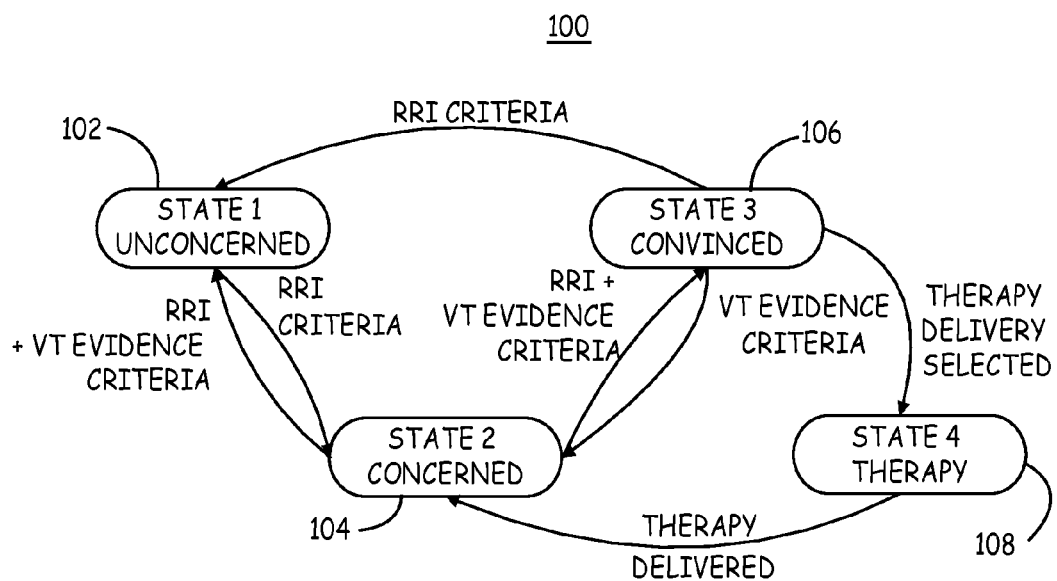
FIG. 3 is a state diagram of operating states included in a tachycardia detection and discrimination algorithm.

FIG. 3 is a state diagram 100 of operating states included in a tachycardia detection and discrimination algorithm. The tachycardia detection algorithm includes four operating states 102, 104, 106 and 108. State 1 102 is an unconcerned state in which RRI monitoring is occurring. An analysis of RRIs is performed to detect a sudden change in the heart rhythm. A sudden change may be a sudden change in heart rate (HR), i.e., a sudden change in the length of RRIs, or a sudden change in RRI variability, i.e., a sudden change in RRI differences. A HR change detector and a RRI variability change detector operate in State 1 102 and will be described in detail below.

A transition to State 2 104, the concerned state, occurs when either sudden change detection criteria or high heart rate criteria applied to measured RRIs are met in State 1 102. A transition to State 2 occurs based on RRI monitoring without performing additional morphology analysis. In order to enter State 2 104, an increase in HR has been detected in State 1 104 such that RRIs that are shorter than the detection lower limit interval have been measured. State 2 104 is a "concerned state" because the HR is increased but the heart chamber that the fast ventricular rate is originating in may be uncertain. Additional analysis is needed to discriminate between SVT and VT. During State 2, evidence of VT is accumulated on a beat-by-beat basis using morphology analysis of the ventricular EGM signals. The morphology analysis is used in addition to the RRI analysis to determine if the rhythm is a "treatable" VT rhythm or "non-treatable" SVT rhythm.

Transition out of State 2, either back to State 1 (unconcerned) or forward to State 3 (convinced) can occur based on RRI data alone or a combination of RRI data and EGM signal morphology data. As such, in State 2 104, RRI monitoring continues and additional monitoring of EGM signal morphology is performed to accumulate evidence of VT on a beat-by-beat basis as will be described in detail herein. If RRI criteria and VT evidence satisfies VT detection criteria, a transition to State 3 106 occurs. If RRI criteria and/or VT evidence no longer meet the criteria required to remain in State 2, a transition back to State 1 102 occurs.

Once State 3 106 is reached, VT is detected and a therapy selection process begins according to a programmed menu of therapies. However, since the onset of the therapy may be delayed due to capacitor charging, a programmed therapy delay, or other reasons, the IMD control system may remain in State 3 for an interval of time. RRI monitoring and morphology analysis performed in State 2 continues in State 3.

A transition from State 3 106 directly to State 1 102 can occur if the RRI data indicates that the HR falls below a concerning rate, i.e. below the detection lower rate limit. A transition to State 2 104 may occur if RRI data or morphology analysis no longer satisfy VT detection criteria but remain above a threshold for the concerned state.

A transition from State 3 106 to State 4 108 occurs when a pending therapy is ready. For example, a therapy delay, capacitor charging or other time interval leading up to actual therapy onset expires and a transition to State 4 is made. Therapy is delivered in State 4. After therapy delivery, a transition back to state 2 104 occurs to continue monitoring the heart rhythm. The detection and discrimination algorithm remains in State 2 104 until reaching a decision to return to State 1 102 or to State 3 106 based on RRI criteria and morphology analysis. The various state transitions and operations performed within each detection algorithm state will now be described in greater detail.

Figure 4:
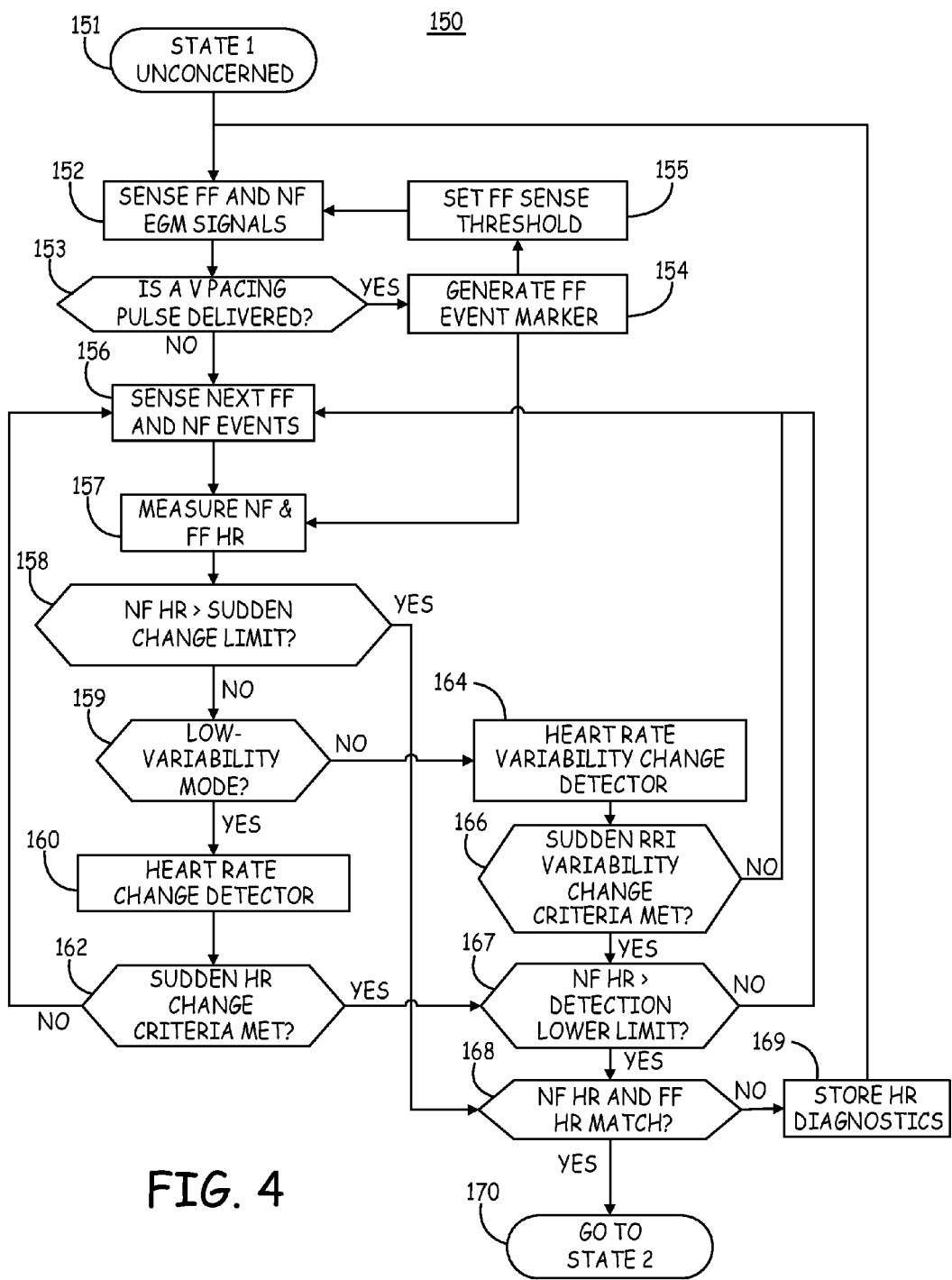
FIG. 4 is a flow chart of operations performed in State 1 of the tachycardia detection algorithm.

FIG. 4 is a flow chart 150 of operations performed in State 1 of the tachycardia detection algorithm. Flow chart 150 and other flow charts shown herein are intended to illustrate the functional operation of the device, and should not be construed as reflective of a specific form of software or hardware necessary to practice the methods described. It is believed that the particular form of software, firmware and/or hardware will be determined primarily by the particular system architecture employed in the device and by the particular detection and therapy delivery methodologies employed by the device. Providing software, firmware and/or hardware to accomplish the described functionality in the context of any modern medical device, given the disclosure herein, is within the abilities of one of skill in the art.

Methods described in conjunction with flow charts presented herein may be implemented in a computer-readable medium storing instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

State 1 is entered at block 151 either upon initialization of the IMD or after returning to State 1 from State 2 or State 3. Both FF and NF EGM signals are sensed at block 152. A dual vector sensing approach is used to allow confirmation of a detected heart rate using a second EGM signal before a state transition occurs. The dual vector sensing approach also allows for selective analysis of the overall signal morphology within an analysis window and/or analysis of specific features of the FF and NF signals within the analysis window, referred to herein as "beat features", to be performed in manner that provides the highest separation of SVT and VT when operating in States 2 and 3.

When sensing the NF and the FF EGM signals, the NF sensing electrode pair may also be used for delivering pacing pulses to the heart. If no ventricular pacing pulse is delivered (as determined at decision block 153), the next NF and FF events are sensed at block 156. A NF HR and a FF HR are determined at block 157 using the respective NF and FF RRIs measured between the currently NF or FF sensed event, respectively, and the previously NF or FF sensed event.

As will become apparent from the illustrative embodiment described in detail herein, the NF EGM signal can be considered the "primary" sensing signal because the NF signal is used for sensing cardiac events for measuring RRIs for estimating the HR, detecting a sudden change in the heart rhythm during State 1 operations, and for setting a morphology analysis window during State 2 operations. Analysis of the FF EGM signal is "secondary" in that the FF EGM signal is used to verify a NF heart rate and for morphology analysis in State 2 after a concerning rhythm is identified. As such, in some embodiments, identifying sensed events and measuring intervals between sensed events on the FF EGM signal may be delayed in time relative to NF event sensing. The cardiac events may be sensed and RRIs may be measured in real time on the NF EGM signal. The FF EGM signal may be analyzed in real-time simultaneously with the NF EGM signal or buffered for later analysis. Searching for FF sensed events using the buffered signal may be performed retrospectively upon determining a need to verify the outcome of the NF signal analysis. A retrospective analysis of a stored FF EGM signal for sensing R-waves may be more accurate than real-time sensing of cardiac events.

If a ventricular pacing pulse is delivered as determined at block 153, the FF EGM signal is "forced" to "sense" a cardiac event. A FF event marker is automatically generated at block 154 for use in measuring RRIs for estimating a FF HR at block 156 for the current heart beat. Additionally, the FF sense threshold is set at block 155 in preparation for sensing the next FF event. Normally, an auto-adjusting sensing threshold will track the amplitude of a sensed event and decay thereafter. Since a pacing pulse causes an automatically-generated "sense" event on the FF signal, an alternative method for setting an auto-adjusting sense threshold is used when a pacing pulse is delivered.

When a pacing pulse is delivered, the automatically-generated FF event marker is followed by a blanking period. The FF sensing threshold then tracks the amplitude of the evoked response throughout the FF EGM blanking period but no new events are sensed during the blanking period. When the blanking period expires, the FF sensing threshold is set to a percentage of the peak amplitude tracked during the blanking period at block 155. The FF sensing threshold thereafter decays over time until another pacing pulse is delivered or until an intrinsic event is sensed on the FF EGM signal.

A NF HR and a FF HR are measured at block 157 using respective NF and FF RRIs measured between sensed events. If the NF HR is greater than a sudden change limit, as determined at block 158, and the NF and FF HRs approximately match (block 168), a transition to State 2 occurs at block 170. The sudden change limit used at block 158 is a threshold heart rate or corresponding RRI falling between the detection lower rate limit and the SVT limit. A heart rate greater than the sudden change limit (or RRI shorter than the sudden change limit interval) is identified as a "concerning rhythm" without requiring a sudden change in the heart rhythm to be detected. Specifically, the detection algorithm does not require observation of a sudden change in HR or in RRI variability in order to identify a concerning rhythm. For example, a sudden change limit might be a HR of 190 beats per minute (bpm). Above 190 bpm, no sudden change detection requirements are needed to change from State 1 to State 2 because the very high HR itself is considered a concerning heart rhythm.

In order to compare the current HR to a HR threshold, such as the sudden change limit, a number of methods may be used. One method includes determining a median of the most recent "m" RRIs and comparing the median to a threshold heart rate. Another method requires a specific number "n" RRIs out of the most recent "m" RRIs to be shorter than an interval corresponding to the threshold HR.

In one embodiment, a predetermined number "m" consecutive RRIs are collected and the nth smallest RRI out of the "m" intervals is used as an estimate as the current HR for comparison to a HR threshold. For example, the ninth smallest RRI out of the most recent 12 RRIs may be used as an estimate of the current HR for comparisons to HR thresholds. At block 157, if the ninth smallest RRI is shorter than a sudden change limit interval, the detection algorithm proceeds to decision block 168.

The method of using the nth smallest RRI out a predetermined number of collected RRIs as a metric of HR can yield a different result than using a median RRI. When using a median value, an undersensed event corrupts one RRI (by creating one very long RRI). An oversensed event corrupts two RRIs (by creating two very short RRIs). Therefore, oversensing can result in a corrupted median value more quickly than undersensing. In practice, oversensing is typically a more common occurrence than undersensing in modern ICDs. Oversensing can result in an overestimate of the HR and could lead to unnecessary transitions to State 2. By selecting the nth shortest RRI out of a specified number of recent, consecutive RRIs, the likelihood of transitioning to State 2 due to oversensing is reduced as compared to the method of using median RRI values as a metric of HR.

When the NF HR estimate exceeds the sudden change rate limit, a comparison of the NF HR to the FF HR at block 168 may be included to confirm the detected NF HR. The comparison at block 168 may include a determination relating to the reliability of the FF EGM signal to ensure the FF signal is not noise or artifact corrupted and that the signal strength is reliable. Either of the NF and FF signals may be deemed unreliable for estimating heart rate if a predetermined percentage of sensed events have a peak amplitude at or near the minimum cardiac event sensing threshold or above the event sensing threshold but below a predefined reliable threshold amplitude. A high frequency of sensed events having amplitudes barely reaching the sensing threshold, or below reliable amplitude threshold set slightly higher than the event sensing threshold, may raise concern that these sensed events are oversensed or that other events may be occurring that are undersensed. An EGM signal may additionally or alternatively be determined to be unreliable if a sensed event has not occurred for an undersensing threshold interval. For example, if at least 2 seconds or more have passed between two sensed events, the EGM signal may be classified as unreliable for estimating HR.

The combined NF and FF RRI measurements may be used in a variety of ways to verify an accurately sensed heart rate, without significant error due to oversensing, undersensing, noise artifact or other factors. In one embodiment, a NF HR may be verified using the FF HR at block 168 by verifying that for every sensed event on the NF EGM signal, there is also a corresponding sensed event on the FF EGM signal occurring within a predefined interval of time from the NF sensed event, e.g. within approximately 20 ms.

A similar method for determining a metric of HR may be applied to the FF signal as was applied to the NF signal, such as the foregoing example of the nth smallest RRI out of a most recent number of consecutive RRIs. If the FF HR estimate does not approximately match the NF HR estimate, the detection algorithm remains in State 1. In particular, if the FF HR estimate is less than the sudden change limit, the lower estimate based on the FF HR is relied upon. The process returns to block 152 to sense the next FF and NF events and measure the next RRI on both the FF and NF EGM signals. While not shown explicitly in FIG. 4, if the FF HR estimate is significantly different but faster than the NF HR rather than slower, e.g. faster than the SVT limit, a transition to State 2 at block 170 may be made.

If the HR estimate from the FF EGM differs significantly from the heart rate estimate of the NF EGM, buffered RRIs used in making this determination and/or FF and NF EGM signal segments may be stored as diagnostic data at block 169 to record this occurrence of a mismatch between FF and NF HRs. Such diagnostics would be helpful for clinicians and technicians to determine when and why the dual vector EGM signal data is contradictory in terms of HR estimates and take corrective action as needed, e.g., when the contradictory results appear to be due to noise, undersensing, lead-related conditions, or other non-physiological causes.

As long as the HR remains below the sudden change limit (negative result at block 158), either a sudden HR change detector 160 or a sudden RRI variability change detector 164 will operate within State 1. At block 159, the IMD controller determines if the detection algorithm is operating in a low variability (LV) mode or a high variability (HV) mode as long as the NF HR remains below the sudden change rate limit. Control of switching between a LV mode and a HV mode at block 159 will be described in conjunction with FIG. 7.

In the LV mode, a HR change detector operates at block 160 for detecting a sudden change in HR based on sudden change detection criteria applied at decision block 162. Details regarding the operation of the sudden HR change detector at block 160 will be described in conjunction with FIG. 5 below.

If sudden HR change criteria are met at block 162, and the NF HR is greater than the detection lower limit (block 167), and if the NF and FF HRs approximately match (block 168), a transition to State 2 occurs at block 170. The detection lower limit applied at block 167 is the limit applied to the HR below which the heart rhythm is not a concerning rhythm even if a sudden change in HR or in RRI variability is detected. For example, the detection lower limit may nominally be set to 150 bpm. If the HR is less than the detection lower limit, at block 167, the detection algorithm remains in State 1 and returns to block 156 to advance to the next sensed event. The detection algorithm does not advance to State 2 unless the HR estimate obtained on the current beat at least meets the detection lower limit requirement.

If the detection algorithm is operating in the HV mode (a negative result at block 159), a RRI variability change detector operates at block 164. If the HR is highly variable from beat-to-beat, e.g. during atrial fibrillation (AF), frequent ectopy, unstable intrinsic activations, bigemeny, trigemeny, or other highly variable rhythms, a sudden change in HR marking the onset of VT may be masked by the highly variable RRIs.

As such, when the RRIs are highly variable beat-to-beat, the tachycardia discrimination algorithm operates in a HV mode during State 1 to enable detection of a sudden change in the RRI variability. Generally, if a VT arises from a rhythm characterized by highly variable RRIs, a sudden decrease in the RRI variability will occur. When criteria for detecting a sudden change in RRI variability are satisfied (block 166), the NF HR is greater than the detection lower limit (block 167), and the NF and FF HRs approximately match (block 168), a transition to State 2 occurs at block 170. Details regarding the operation of the sudden RRI variability change detector at block 164 will be described in conjunction with FIG. 8 below.

Figure 5:
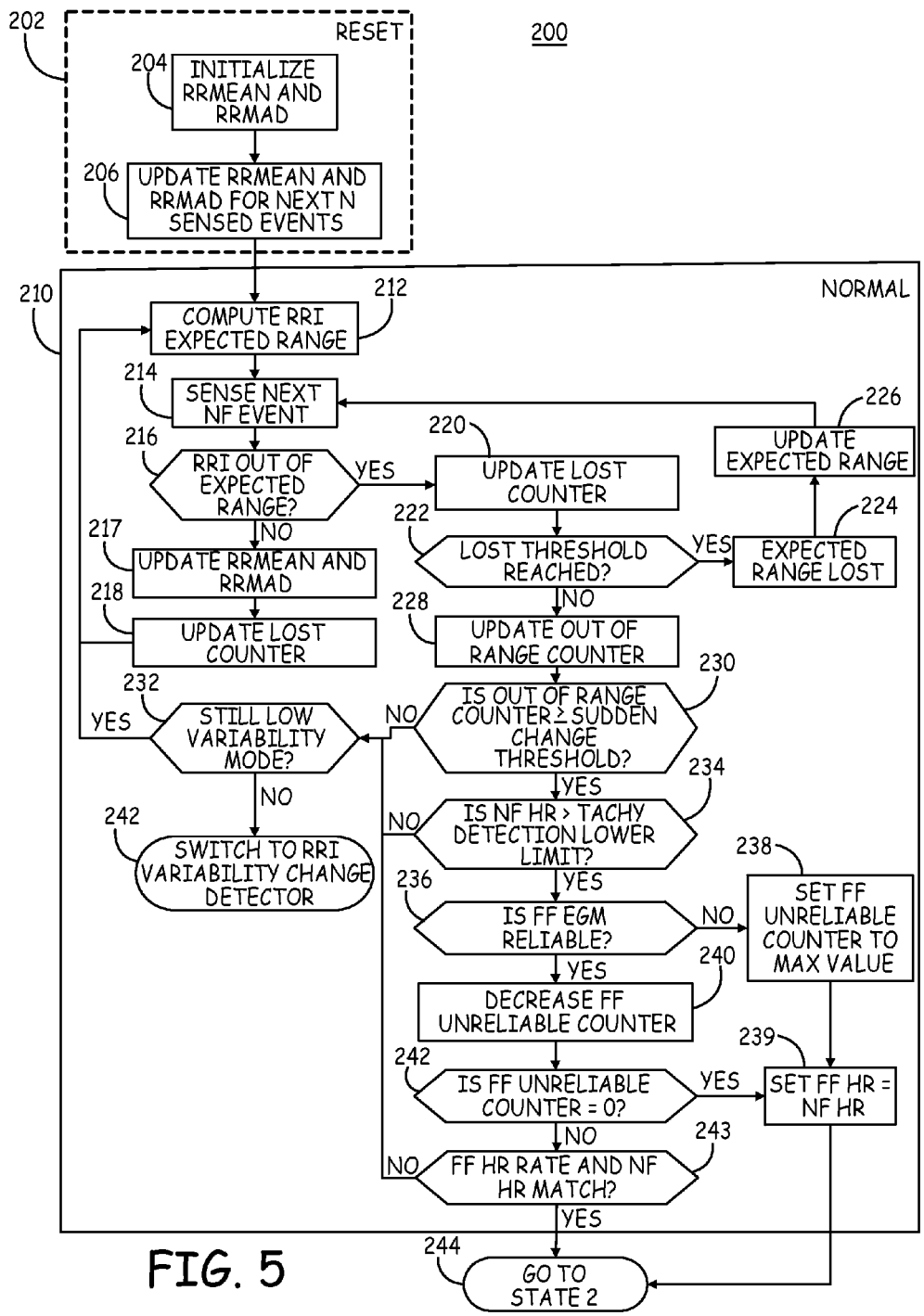
FIG. 5 is a flow chart of a sudden heart rate change detector that operates during a low RR interval variability mode of State 1.

FIG. 5 is a flow chart 200 of a sudden HR change detector that operates during the LV mode of State 1. The sudden HR change detector can operate in a reset mode 202 or a normal mode 210. The reset mode 202 operates upon device initialization or in response to a manual reset of the algorithm. During the reset mode 202, two metrics of RRIs from the NF EGM signal are initialized at block 204. A mean RRI (RRMEAN) is initialized to a nominal value, for example 900 ms. Additionally, an expected absolute difference between the next RRI and RRMEAN is initialized. This expected absolute difference, referred to as RRMAD, defines a range around RRMEAN within which the next RRI is expected to fall. A nominal initial value of RRMAD may be approximately 800 ms.

The next "n" RRIs are used to update RRMEAN and RRMAD to actual values based on actually measured RRIs. RRMEAN may be computed upon each new RRI as a weighted sum of the previous RRMEAN and the current RRI. For example, RRMEAN(updated)=0.5(RRMEAN)+0.5 ($RRI_{current}$). While equal weighting coefficients are used in the foregoing equation, it is recognized that other weighting coefficients may be used to rapidly approach an expected RRMEAN value during the reset mode 202.

RRMAD is updated with each new RRI as a weighted sum of the current value of RRMAD and the difference between the currently measured RRI and current value of RRMEAN. For example, RRMAD may be updated according to the following equation:

$$RRMAD(updated)=0.5(RRMAD)+0.5(|RRI_{current}-RRMEAN|+k*RRMEAN)$$

The "k*RRMEAN" term places a constraint on the minimum size of RRMAD wherein 'k' is a small fixed value or percentage, e.g. less than approximately 0.05. Alternatively, RRMAD may be constrained by a fixed minimum value.

After rapidly adapting RRMEAN and RRMAD from initial nominal values to actual expected values using the first "n" RRIs, the algorithm enters normal operation 210.

The number of RRIs, "n", used for adapting RRMEAN and RRMAD during reset mode 202 may be in the range of approximately 3 to 8, without limitation In one embodiment, the first five RRIs are used at block 206 to compute RRMEAN and RRMAD for defining an expected RRI range. If a current RRI does not fall within RRMEAN±RRMAD, that RRI is not used to update RRMEAN or RRMAD and is not counted as one of the "n" RRIs for adapting RRMEAN and RRMAD during the reset mode 202.

During normal operation 210, the expected RRI range is computed using the RRMEAN and RRMAD values at block 212:

$$RRI(expected)=RRMEAN\pm RRMAD$$

When the next NF event is sensed (block 214), the RRI is measured and compared to the expected RRI range at block 216. If the RRI is within the expected range, it is used to update RRMEAN and RRMAD at block 217. The formulas used to update RRMEAN and RRMAD at block 217 may be different than the formulas used during the reset mode of operation 202. For example, different weighting coefficients may be used and/or additional terms may be included. In one embodiment, RRMEAN is computed using a relatively lower weighting applied to the current RRI, such as:

$$RRMEAN(updated)=0.9(RRMEAN)+0.1\ (RRI_{current})$$

RRMAD may be computed as:

$$RRMAD(updated)=0.95(RRMAD)+0.05*(d)*\\(|RRI_{current}-RRMEAN|+k*RRMEAN)*\\\{1-((750-RRMEAN)/1000)\}$$

wherein the constant "d" is a selected factor to stabilize the expected range, the term "k*RRMEAN" is included to constrain the minimum size of RRMAD, and the factor {1−((750−RRMEAN)/1000)} forces the expected range to tighten as the HR increases and to expand as the HR decreases. In other words, the expected RRI range narrows at higher HRs and widens at lower HRs. A maximum size of RRMAD may be defined to constrain the maximum expected range. In one embodiment, RRMAD is limited to a maximum percentage of RRMEAN, for example approximately 20% of RRMEAN.

If an RRI is outside the expected range (RRMEAN±RRMAD), it is not used to compute updated values of RRMEAN and RRMAD. A lost counter is updated at block 220 to count the number of RRIs that are not used for updating the expected range metrics. If the current RRI is greater than RRMEAN+RRMAD, the lost counter is increased by one. If the current RRI is less than RRMEAN−RRMAD, the lost counter is decreased by one.

The lost counter may have a value ranging between the positive and negative values of a lost threshold. When the RRI falls within the expected range (block 216) and are used to update RRMEAN and RRMAD (block 217), the lost counter is updated at block 218 by moving its value one step closer to zero from whatever its current value is.

When the lost counter is increased or decreased in response to an out of range RRI (block 220), the lost counter is compared to a lost threshold at block 222. If the lost threshold has been reached before changing to State 2, the expected RRI range is declared lost at block 224. The expected RRI range is updated at block 226 by adjusting the value of RRMEAN up or down by a percentage of RRMAD, depending on the value of the lost counter.

In one embodiment, if the current RRI is greater than the expected range and the positive lost threshold is reached, RRMEAN is increased by 25% of RRMAD at block 226 to update the expected RRI range. If the current RRI is less than the expected range and the negative lost threshold is reached, RRMEAN is decreased by 25% of RRMAD at block 226. In this way, a shift in RRMEAN repositions the expected RRI range so that the repositioned range again represents the range of currently expected RRIs. This repositioning of the expected RRI range can occur when the HR remains less than the sudden change limit and other sudden change detection criteria for transitioning to State 2 have not been met. The algorithm remains in State 1 and returns to block 214 to sense the next NF event.

If the lost threshold has not been met at block 222, an Out of Range Counter is updated at block 228. If the RRI is unexpectedly short, i.e. less than RRMEAN−RRMAD, the Out of Range Counter is increased by one. Otherwise, if the RRI is within or greater than the expected range, the Out of Range Counter is decreased by two. The Out of Range counter is used to count the number of RRIs that are consistently shorter than the expected RRI range. If the count trends upward, consistently short RRIs are occurring indicating the possibility of a sudden change in HR. The Out of Range counter has a minimum limit of zero and a maximum limit, e.g. 20.

The Out of Range Counter is compared to a threshold count for detecting a sudden change in HR at block 230. If the sudden change detection threshold has not been reached, and the algorithm is still operating in the LV mode (as determined at block 232), the algorithm remains in State 1 and the process returns to block 212. The expected RRI range in this case will remain the same since the current RRI is out of range and will not be used to compute new RRMEAN and RRMAD values.

If the Out of Range Counter exceeds the sudden change detection threshold at block 230, e.g. a threshold of 10, indicating recent RRIs are consistently shorter than an expected range, the NF HR is compared to the detection lower limit at block 234. As described previously, a NF HR may be estimated as the nth smallest RRI out of a specified number of the most recent RRIs. If the NF HR estimate does not exceed a detection lower rate limit for detecting tachycardia, and the algorithm is still in the LV mode (block 232), the process returns to block 212. The expected RRI range will again remain the same because the current RRI is out of range. Even though a sudden HR change has been detected, the HR is too low to be considered a concerning heart rhythm for tachycardia detection purposes.

If the NF HR is faster than the detection lower limit as determined at block 234, the HR from the FF EGM signal is checked to verify the NF HR. At block 236, the FF EGM signal is first analyzed to determine if the signal is reliable. Since the FF EGM signal is more susceptible to noise or artifact, noise/artifact rejection criteria may be applied to the FF EGM signal to reject the FF HR data when it is determined to be unreliable. The FF EGM must also be of sufficient amplitude in order to be considered "reliable". In other words, if the FF R-wave signals are of very small amplitude, the HR estimate that comes from the FF EGM is considered unreliable and is not used to verify or disprove a NF HR.

Specific criteria relating to EGM signal amplitude and/or FF RRIs may be applied to the FF signal at block 236 to verify that it is a reliable signal for estimating the HR. For example, the FF EGM signal may be determined unreliable if an unacceptable number of R-waves out of a predetermined number of the most recent R-waves (sensed on the FF EGM signal) are less than a threshold amplitude and/or extremely short or extremely long RRIs are present. In one specific example, the FF EGM is determined to be an unreliable signal if the third shortest RRI out of the most recent 12 RRIs is less than 500 ms and at least 4 of the most recent 12 sensed R-waves have peak amplitudes less than 500 microvolts with at least one of those low amplitude R-waves being within the most recent three sensed R-waves. Additionally, the FF EGM signal can be determined unreliable if a sensed event has not occurred within some maximum time limit (indicating a low amplitude signal and possible undersensing). For example, if at least approximately 2,550 ms have passed since the most recent FF sensed event the FF EGM signal is determined to be unreliable.

If the FF EGM signal is determined to be unreliable, a FF unreliable counter is increased at block 238. The NF EGM signal evidence for a concerning rhythm is then relied upon for transitioning to State 2, the "concerned" state, at block 244. The FF EGM is not used to either verify or disprove the NF EGM result in detecting a concerning rhythm.

In one embodiment, if the unreliable signal criteria are met at block 236, the FF signal remains classified as unreliable for a period of time. To accomplish this, the FF unreliable counter is set to a maximum value, e.g. 12, at block 238 when the unreliable criteria are met. The FF HR estimate is set to the same value as the NF HR estimate at block 239. As a result, the NF and FF heart rates will certainly match at decision block 243, and a transition to State 2 occurs at bock 244.

When the FF EGM signal is found to be reliable at block 236, the FF unreliable counter is decreased by one at block 240. As long as the FF unreliable counter remains greater than zero, as determined at block 242, the FF EGM signal is considered unreliable. The FF HR estimate is set equal to the NF HR estimate at block 239, resulting in an automatic match of the NF and FF HRs at block 243, and a transition to State 2 at block 244.

While not explicitly shown in the flow charts provided, a similar analysis of the NF EGM signal may be performed to determine when the NF signal is unreliable. If the NF EGM signal is found to be unreliable, the FF EGM signal may be used as the primary sensing signal for sensing cardiac events and setting a morphology analysis window until the NF EGM signal is found to be reliable again.

If the FF unreliable counter has reached zero at block 242, the FF HR is estimated and compared to the NF HR at block 243. The FF HR may be estimated using a similar method as described above for estimating the NF HR (i.e. the nth RRI out of "m" most recent RRIs). When the FF HR estimate approximately matches the NF HR estimate (block 243), or when the FF HR estimate exceeds the sudden change limit, the determination of a concerning rhythm is confirmed by the FF signal. Transition to state 2 occurs at block 244. A HR match may be defined as a NF HR estimate and FF HR estimate being with a predefined range or percentage of each other.

On the other hand, if the FF EGM signal is reliable, the FF HR estimate does not approximately match the NF HR estimate, and is not greater than the sudden change limit at block 243, the transition to State 2 does not occur. The algorithm returns to block 232.

At block 232, if a switch from the LV mode to the HV mode has occurred, the method for detecting a sudden change in the heart rhythm switches from the sudden HR change detector to a sudden RRI variability detector at block 242. Otherwise the detection algorithm remains in the LV mode and returns to block 212. The expected RRI range will remain the same for the current beat and the process will advance to the next NF sensed event at block 214.

Figure 6:
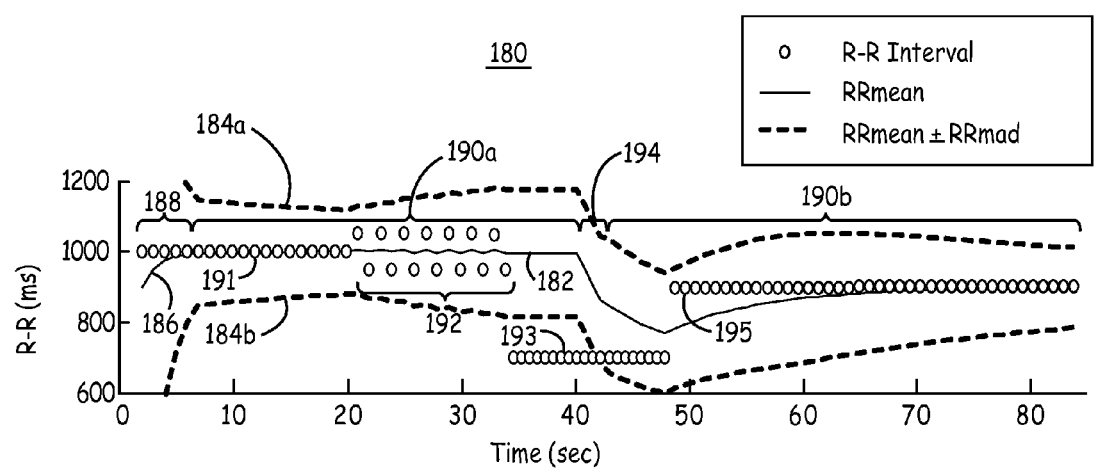
FIG. 6 is a plot of the expected RR interval range computed using RRMEAN and RRMAD metrics of RR intervals (RRI).

FIG. 6 is a plot of the expected RRI range computed using the RRMEAN and RRMAD metrics of RRIs as described above. Measured RRIs are represented by open circles and are plotted in ms along the y-axis over time in seconds along the x-axis. RRMEAN 182 is computed from the measured RRIs and is shown by a solid line. The positive boundary 184a and negative boundary 184b, collectively 184, are defined by ±RRMAD and are shown by the dashed lines above and below RRMEAN 182. The boundaries 184a and 184b define the RRI range in which the next RRI is predicted to fall based on past RRIs.

An initial value 186 of 900 ms is assigned to RRMEAN, and an initial value of 800 ms is assigned to RRMAD. During a reset mode of operation 188, the first five RRIs are used to rapidly converge on an actual RRMEAN value and an actual RRMAD value using the equations provided above. Normal operation 190a of State 1 of the detection algorithm begins after the reset mode 188. Initially, a string of consistent 1000 ms RRIs 191 occurs. RRMEAN 182 tracks the consistent RRIs. The ±RRMAD upper and lower boundaries 184 gradually tighten around RRMEAN to narrow the expected RRI range.

An interval of variable RRIs 192 causes the expected RRI range to expand as can be seen by a widening of the ±RRMAD boundaries 184. Following the variable RRIs 192, a series of high rate RRIs 193 occurs. These RRIs are suddenly shortened but remain longer than a nominal detection lower limit interval of 500 ms such that a state transition does not occur. When the sudden rate change occurs, the short RRIs are out of the expected RRI range. The RRMEAN and RRMAD metrics are not adjusted in response to the out-of-range RRIs and exhibit a flat response to the consistently out of range RRIs.

After ten RRIs that are consistently out of range, the lost counter reaches a threshold count for repositioning the expected RRI range. A lost mode 194 operates for repositioning the expected RRI range. In this example, the RRIs are consistently less than the expected range, but the HR is still lower than a detection lower rate limit so the algorithm remains in State 2. When current RRI is less than the expected RRI range, the expected RRI range is repositioned by adjusting RRMEAN by a predetermined decrement on a beat-by-beat basis until the current RRI falls within the expected range.

If RRIs are consistently greater than an expected RRI range, RRMEAN would be increased by a predetermined increment on each RRI to reposition the expected RRI range. In one embodiment, when a lost count threshold is reached, RRMEAN is decreased or increased as needed by a percentage of the current value of RRMAD, for example 25% of RRMAD. This adjustment of RRMEAN allows the expected RRI range to be quickly repositioned to include a current RRI. Thereafter, normal operation 190b resumes.

RRMEAN and RRMAD are updated according to the normal operation equations as each RRI falls within the expected range during normal operation 190b. At 195, the RRIs increase to 900 ms, which is still within the expected RRI range as defined by the ±RRMAD boundaries 184. RRMEAN and RRMAD continue to be adjusted on a beat-by-beat basis using the equations described above. A gradual tightening of the expected RRI range is observed.

Figure 7:
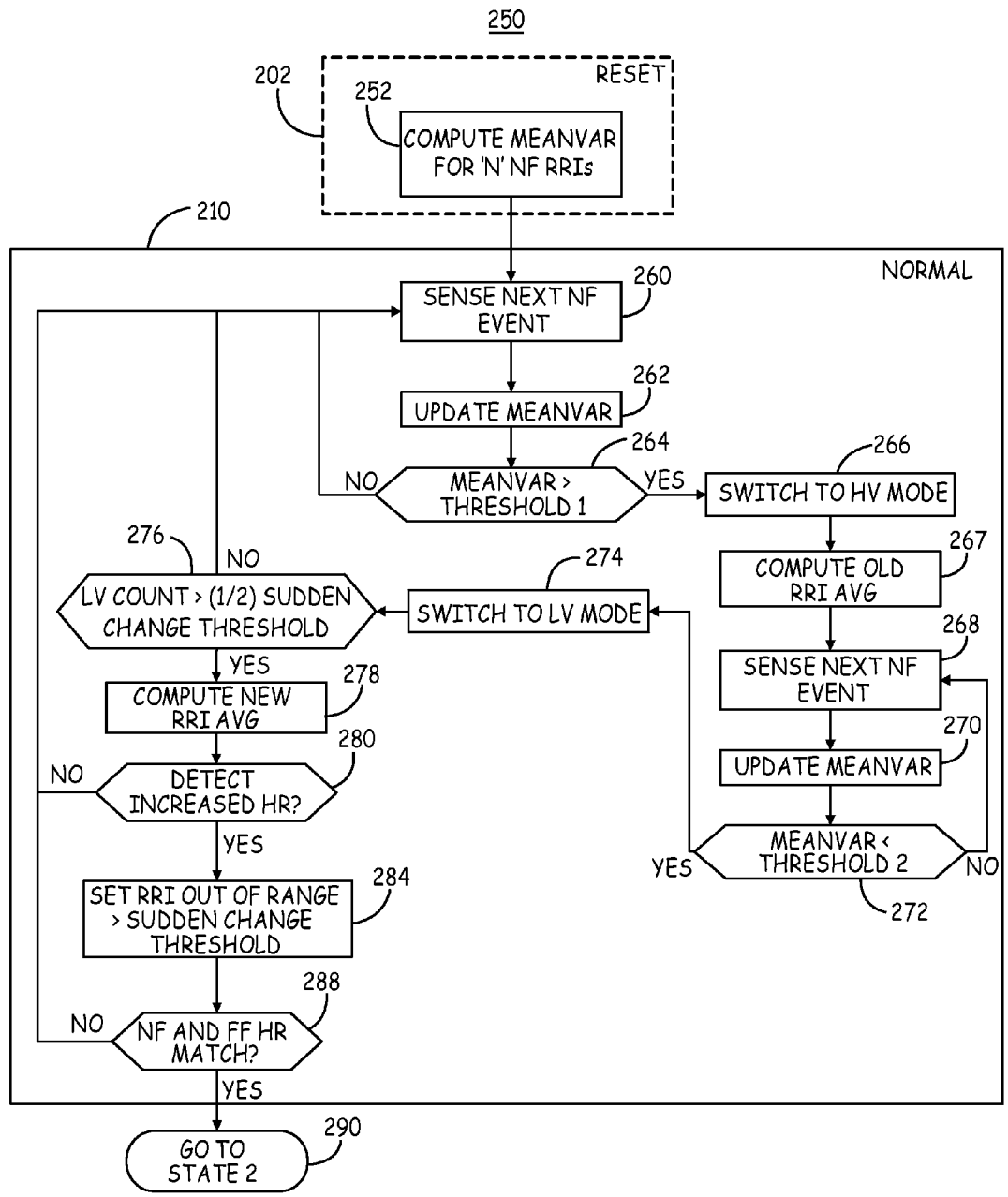
FIG. 7 is a flow chart of a method for controlling switching between low RRI variability and high RRI variability modes of operation during State 1.

FIG. 7 is a flow chart 250 of a method for controlling switching between LV and HV modes of operation during State 1. As described previously, during the LV mode, a sudden HR change detector operates. During the HV mode, a sudden RRI variability change detector operates. In order to control which of the LV and HV modes the detection algorithm is operating in, a metric of the variability of the RRIs, "MEANVAR", is monitored.

In flow chart 250, reset operation 202 and normal operation 210 correspond to the reset operation and normal operation shown in FIG. 5. Thus, processes shown in FIG. 7 that occur during reset operation 202 and during normal operation 210 are in addition to the processes described during reset and normal operation in conjunction with FIG. 5.

During reset operation 202, in addition to computing initial values for RRMEAN and RRMAD, an initial value for MEANVAR is computed for the first "n" RRIs measured on the NF EGM signal. MEANVAR is computed as a weighted sum of the current value of MEANVAR and the difference between the current RRI and the previous RRI. For example:

$$\text{MEANVAR(updated)} = W_1(\text{MEANVAR}) + W_2(|RRI_i - RRI_{i-1}|)$$

During the reset mode, MEANVAR may be assigned an initial nominal value then updated to an actual MEANVAR using the above equations. During reset, $W_1$ and $W_2$ may be set to equal values of 0.5.

During normal operation 210, the NF EGM signal is acquired at block 260 for sensing the next NF event. During normal operation, MEANVAR may be computed using a weighted sum of the current MEANVAR value and the difference between the current RRI and previous RRI. In one embodiment, the current MEANVAR may be multiplied by a weighting coefficient W1 of approximately 0.9 or higher and the current RRI difference may be multiplied by a weighting coefficient W2 of approximately 0.1 or lower. For example W1 may be approximately 0.96 and W2 may be approximately 0.04.

A maximum upper limit may be applied to MEANVAR, which may be defined as a percentage of RRMEAN, for example approximately 25% of RRMEAN. In order to limit the influence of outliers, a limit may also be applied to the current RRI difference used to compute MEANVAR. For example, if the current RRI difference is greater than the current value of MEANVAR, the current RRI difference is replaced by the sum of MEANVAR and the larger of MEANVAR and 20 ms.

MEANVAR is updated in response to the NF event at block 262. If the MEANVAR is greater than a first HV threshold, as determined at block 264, the detection algorithm is switched to the HV mode at block 266. Operations for detecting a sudden change during the HV mode will be described in conjunction with FIG. 8.

Upon entering the HV mode, a reference HR estimate, OLD RRI AVG, is computed at block 267. The OLD RRI AVG may be computed as the mean of the most recent RRIs, for example 12 to 16 of the most recent RRIs, and is a measure of the heart rate upon entering the HV mode. As will be described in greater detail below, the OLD RRI AVG is used for detecting an increasing trend in HR in the presence of a decrease in RRI variability. This combination of a sudden decrease in RRI variability accompanied by an increasing trend in HR is an indication of a concerning heart rhythm and can trigger a state transition of the detection algorithm as described below. The increasing trend in HR accompanying a sudden change in RRI variability does not necessarily need to meet criteria for detecting a "sudden" increase in HR, as required by the sudden HR change detector during the LV mode. In the HV mode, a more gradual increase in HR, in conjunction with a sudden decrease in RRI variability, may satisfy criteria for detecting a "sudden change" in the heart rhythm.

During the HV mode, the next NF event is sensed at block 268 and used to update MEANVAR at block 270. If MEANVAR falls below a second LV threshold, as determined at block 272, the detection algorithm switches to the LV mode at block 274. The first HV threshold, THRESHOLD1, used at decision block 264 for switching from a LV mode to a HV mode can be defined as a percentage of RRMEAN or a fixed value. In one embodiment, THRESHOLD1 is set to be in the range of approximately fifteen to twenty percent of RRMEAN. Additionally, a fixed maximum upper limit of MEANVAR during the LV mode may be defined, above which a switch to HV mode occurs. For example, if MEANVAR is greater than approximately 0.18*RRMEAN or greater than a fixed upper limit of 100 ms, the detection algorithm switches to HV mode.

The second LV threshold used at decision block 272 for switching back to the LV mode may be defined the same or differently than the first threshold. In one embodiment, the THRESHOLD2 applied to MEANVAR for switching back to the LV mode is set lower than the first threshold used for switching to the HV mode. For example, the threshold for switching back to LV mode may be defined to be between approximately ten and fifteen percent of RRMEAN. Additionally, a fixed lower limit of MEANVAR during the HV mode may be defined, below which a switch to LV mode occurs. In one embodiment, the detection algorithm switches from the HV mode to the LV mode if MEANVAR is less than 0.12*RRMEAN or less than a lower limit of approximately 70 ms. The hysteresis between switching into and out of the HV mode can reduce switching frequency. The upper and lower limits applied to MEANVAR allow switching to occur when the variability becomes very low or very high independent of the current value of RRMEAN.

After switching to the LV mode at block 274, a LV counter is compared to half of a sudden change threshold. As will be described in conjunction with FIG. 8, the LV counter is used to count the number of RRIs having a low beat-to-beat variability during the HV mode of operation. When the LV counter exceeds a sudden change threshold during the HV mode, a sudden change in RRI variability may be detected. The sudden change threshold applied to the LV count (during HV mode) and the sudden change threshold applied to the RRI out of range count (during LV mode) may be equal or set to distinct values during the different HV and LV operating modes.

The MEANVAR metric of RRI variability is used differently than the LV counter. The MEANVAR metric is used to control switching between the HV mode and the LV mode within State 1 while the LV counter is used to detect a sudden decrease in RRI variability and cause transition from State 1 to State 2 during the HV mode.

If the MEANVAR has decreased to cause a switch from the HV mode to the LV mode at block 274, the current value of the LV counter upon switching from the HV mode is compared to a percentage of the sudden change detection threshold at block 276, for example half of the sudden change detection threshold. If the current value of the LV counter is not greater than the selected percentage of the sudden change detection threshold, the LV mode of operation proceeds as described above in conjunction with FIG. 5. However, if the LV counter is moderately high (e.g. meeting at least half the sudden change detection), a NEW RRI AVG is computed at block 278 to determine if this decrease in RRI variability is also accompanied by an increase in HR. The NEW RRI AVG may be computed as the mean of a predetermined number of the most recent RRIs. For example the most recent eight RRIs (or another number) occurring consecutively up to and including the RRI which caused a switch to the LV mode may be used to compute the NEW RRI AVG.

At block 280, this NEW RRI AVG is compared to the reference HR estimate, OLD RRI AVG computed at block 267 upon entering the HV mode, to determine if the transition out of the HV mode to the LV mode is also accompanied by an increasing trend in HR. A ratio of or difference between the NEW RRI AVG and the OLD RRI AVG may be compared to a threshold for detecting evidence of an increasing HR at block 280. For example if the NEW RRI AVG is less than approximately eighty percent (or another percentage) of the OLD RRI AVG, an increasing HR is detected.

If the change to the LV mode occurs with a LV count greater than half the sudden change detection threshold but is not accompanied by an increasing HR (block 280), the detection algorithm proceeds to operate normally in the LV mode (return to block 260). If an increase in HR is detected, however, this increase in combination with transition to a LV mode with a moderately high LV count may be an indication of a sudden change in the heart rhythm warranting a change to the concerned State 2.

To meet state transition criteria, the Out of Range counter is set to a suprathreshold value for detecting a sudden change at block 284. For example, if the threshold count for detecting a sudden change is set to 10, the Out Range counter may be set to 16 at block 284. This high counter value immediately satisfies the state transition requirement applied to the Out of Range counter during the LV mode. Setting the Out of Range counter to a high value allows time for the FF EGM signal to be analyzed to verify a match between the FF and NF HR estimates, which may be an added requirement before transitioning to State 2.

A FF HR estimate is computed and compared to a NF HR estimate at block 288. The process performed at block 288 may correspond generally to blocks 236 through 243 of FIG. 5 wherein the FF EGM signal reliability is first determined and if found reliable a FF HR estimate is determined. If the NF and FF HR estimates match, or the FF HR estimate is greater than the sudden change limit, a transition to State 2 occurs at block 290. If the FF EGM signal is unreliable, the results of the NF signal analysis are relied on for effecting a state transition at block 290. Otherwise, when the FF signal is found reliable, but the FF HR does not match the NF heart rate estimate, the transition to State 2 does not occur. The process returns to block 210 and remains in the LV mode of State 1.

Figure 8:
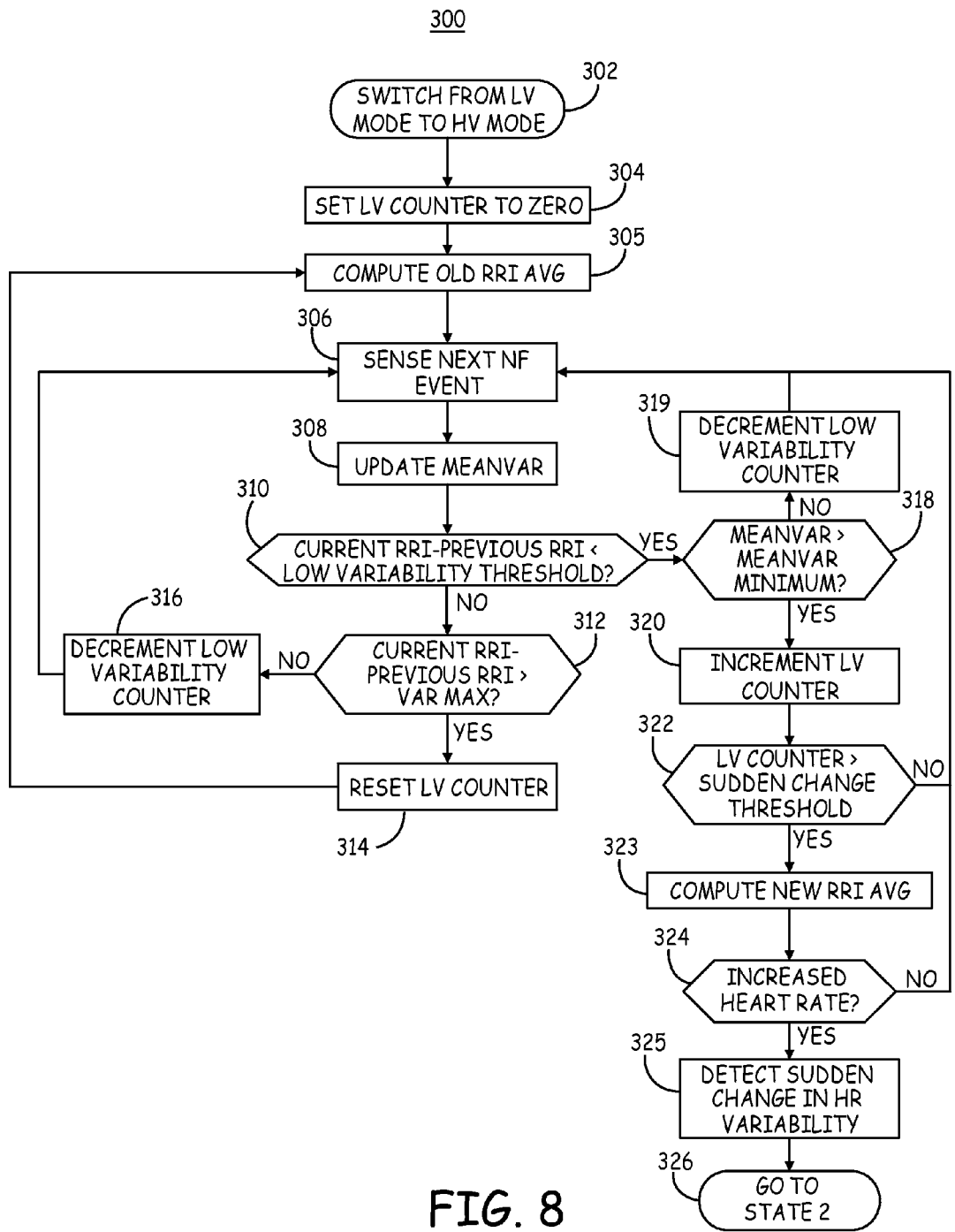
FIG. 8 is a flow chart of operations performed by the sudden RRI variability change detector during the high variability mode.

FIG. 8 is a flow chart 300 of operations performed by the sudden RRI variability change detector during the HV mode. Upon switching from the LV mode to the HV mode at block 302, the detection algorithm resets a LV counter to zero at block 304. The LV counter is used to count RRI differences that are smaller than expected during the HV mode of operation. A high count of less than expected RRI differences indicates consistently low RRI variability. A change in the heart rhythm from highly variable RRIs to small beat-to-beat RRI variation may be associated with VT and may therefore be identified as a concerning rhythm, particularly when accompanied by an increase in HR.

A metric of the average HR, OLD RRI AVG is computed (block 305), upon entering the HV mode. This metric OLD RRI AVG is used as a reference HR for determining if an increase in HR accompanies a decrease in RRI variability. The combination of a sudden change from high to low RRI variability and increased HR is used to detect a sudden change in the heart rhythm during the HV mode of operation in State 1. The OLD RRI AVG may be computed as the average of the most recent RRIs, for example the most recent sixteen consecutive RRIs.

At block 306, the next NF event is sensed and used to update MEANVAR at block 308. As described in conjunction with FIG. 7, MEANVAR is used to track RRI variability for controlling switching between the HV and LV modes and was initialized during the reset operation 202 shown in FIG. 7. MEANVAR is also used in conjunction with a LV counter for detecting a sudden change in RRI variability during the HV mode.

At block 310, the absolute difference between the current RRI and the previous RRI, i.e. the current RRI difference, is compared to a low variability threshold. The low variability threshold applied to the RRI differences may be defined as a percentage of MEANVAR such that the current RRI variability is compared to an expected variability metric. In one embodiment, the low variability threshold applied to the beat-to-beat RRI differences is 0.5*MEANVAR. The low variability threshold may include an absolute limit of the beat-to-beat variability. For example, if the current RRI difference is less than 0.5*MEANVAR or less than approximately 30 ms, the current RRI difference may be considered to be low.

If the difference is less than the low variability threshold (evidence of low RRI variability), the current value of MEANVAR is compared to a minimum MEANVAR threshold at block 318. If the current MEANVAR is greater than the minimum threshold, the LV counter is increased at block 320. The requirement that MEANVAR be greater than a minimum threshold is included such that the detection of a significant decrease in RRI variability can only occur only when the mean variability is already greater than some minimum level to begin with. If the MEANVAR is above a minimum level, the current RRI difference less than a LV threshold represents a potentially sudden decrease in RRI variability. The LV counter is increased at block 320 to maintain a count of the RRI differences that are less than the LV threshold (block 310) when MEANVAR is above the minimum threshold (block 318). RRI differences meeting these criteria provide evidence of a sudden change from high RRI variability to low RRI variability.

If the current RRI difference is low (i.e. less than the LV threshold at block 310), and MEANVAR is also less than a minimum threshold, e.g. less than approximately 20 ms, the LV counter may be decreased at block 319. MEANVAR computed as a running mean of RRI variability is not high enough to detect a decrease in RRI variability. The detection algorithm remains in the HV mode in State 1, and returns to block 306 to sense the next NF event.

When the LV counter is increased at block 320, it is compared to a sudden change threshold at block 322. If the LV count is greater than the sudden change threshold, a NEW RRI AVG is computed at block 323 as a metric of the current HR. The NEW RRI AVG may be computed as an average of the most recent RRIs, for example the most recent eight RRIs occurring consecutively up to and including the RRI which caused the LV counter to exceed the sudden change threshold.

The NEW RRI AVG is compared to the reference OLD RRI AVG to determine if the sudden change in RRI variability is accompanied by an increasing trend in HR. In one embodiment, a ratio of or difference between the NEW RRI AVG and the OLD RRI AVG is compared to a threshold. For example if the NEW RRI AVG is less than approximately ninety percent of the OLD RRI AVG, evidence of an increasing HR is detected at block 324. It is recognized that other methods of estimating a current HR and a reference HR and alternative threshold criteria can be used for detecting evidence of an increasing HR associated with a sudden change in RRI variability.

If evidence of an increasing HR accompanying the sudden change in RRI variability is detected at block 324, a sudden change in the heart rhythm is detected at block 325. A transition from the unconcerned State 1 to the concerned State 2 occurs at block 326. If the LV counter has not reached the sudden change threshold (block 322) or the HR has not increased to meet criteria for detecting an increase in HR (block 324), the algorithm returns to block 306 to sense the next NF event.

Referring again to block 310, if the difference between the current RRI and previous RRI is greater than the low variability threshold (evidence of sustained high RRI variability), the RRI difference is compared to a maximum variability threshold at block 312. If the RRI difference is greater than a maximum variability threshold, e.g. greater than approximately 90 ms, then the LV counter is reset to zero at block 314. The detection algorithm remains in the HV mode of operation in State 1 and returns to block 305 to compute an updated value of OLD RRI AVG.

In some embodiments, OLD RRI AVG is updated every time the LV counter is reset to zero. In other embodiments, additional criteria relating to the behavior of RRI differences may be required before updating the OLD RRI AVG value at block 305. For example, a predetermined number of consecutive RRI differences greater than the maximum variability threshold may be required before updating the OLD RRI AVG value. Another criterion that may be required before updating OLD RRI AVG is that MEANVAR is greater than the MEANVAR minimum.

In one embodiment, OLD RRI AVG is computed when the LV counter is reset to zero and at least four consecutive RRI differences have exceeded the maximum variability threshold (e.g. 90 ms). Alternatively, OLD RRI AVG is updated when the consecutive RRI differences at least meet another lower threshold (e.g. 30 ms or a percentage of MEANVAR) and MEANVAR is at least greater than the MEANVAR minimum value (e.g. 20 ms). Various criteria regarding the current LV counter value, behavior of the most recent RRI differences and/or MEANVAR may be used alone or in combination for determining when to compute an updated value of OLD RRI AVG.

When updating OLD RRI AVG, the formula for computing OLD RRI AVG may be the same or different than the formula used to compute an initial value of OLD RRI AVG upon entering the HV mode. For example, in both cases the most recent sixteen (or another number) RRIs may be averaged to compute OLD RRI AVG. In other embodiments, a different number of recent RRIs may be used when OLD RRI AVG is updated in response to resetting the LV counter during the HV mode of operation as compared to the number of RRIs used to compute OLD RRI AVG upon entering the HV mode.

If the current RRI difference at block 310 is greater than the low variability threshold but not greater than the maximum variability threshold (negative result at block 312), the LV counter is decreased at block 316. In summary, in response to moderate beat-to-beat variability, the LV counter is decreased (block 316). In response to high variability, the LV counter is reset to zero (block 314). In response to low variability, the LV counter is increased (block 320) as long as the current MEANVAR is greater than a predetermined minimum value. The LV counter will reach a sudden change threshold when the RRI differences are consistently small. This low variability in RRIs following a period of high variability (MEANVAR greater than a minimum threshold) and accompanying increase in HR is evidence of a concerning rhythm resulting in transition to State 2.

In summary, a transition from the unconcerned State 1 to the concerned State 2 may occur in response to at least four conditions. One condition that causes a transition to State 2 is the detection of a sudden increase in HR during the LV mode of operation as described in conjunction with FIG. 5. Another condition that causes a State 1 to State 2 transition is the detection of a sudden decrease in RRI variability accompanied by an increasing HR during the HV mode of operation as described in conjunction with FIG. 8. Still another condition that causes a transition to State 2 is a moderate decrease in RRI variability that results in a switch from the HV mode to the LV mode within State 1 accompanied by evidence of increasing HR as described in conjunction with FIG. 7. These conditions each relate to the detection of a sudden change in the rhythm when the estimated HR is less than a sudden change rate limit but greater than a detection lower rate limit. When the estimated HR is greater than the sudden change rate limit, a transition from State 1 to State 2 occurs independent of the sudden HR change detector and the sudden RRI variability change detector (as seen at step 157 of FIG. 4).

Any of the situations relating to a sudden change in HR, a sudden change in RRI variability, or a combination of decreasing RRI variability and increasing HR, when detected consistently enough from beat-to-beat to cause the various counters described herein to reach predefined threshold levels, are inclusively referred to herein as a "sudden change" in the heart rhythm. A sudden change warrants additional State 2 monitoring of the EGM signal for detecting and discriminating tachycardia. Thus various criteria can be defined relating to a sudden increase in HR, a sudden decrease in RRI variability, or a combination of consistently increasing HR and decreasing RRI variability, for use in effecting a transition from State 1 to State 2. These criteria are in addition to detecting a heart rate above the sudden change limit, above which sudden change criteria need not be met to advance to the concerned State 2.

Figure 9:
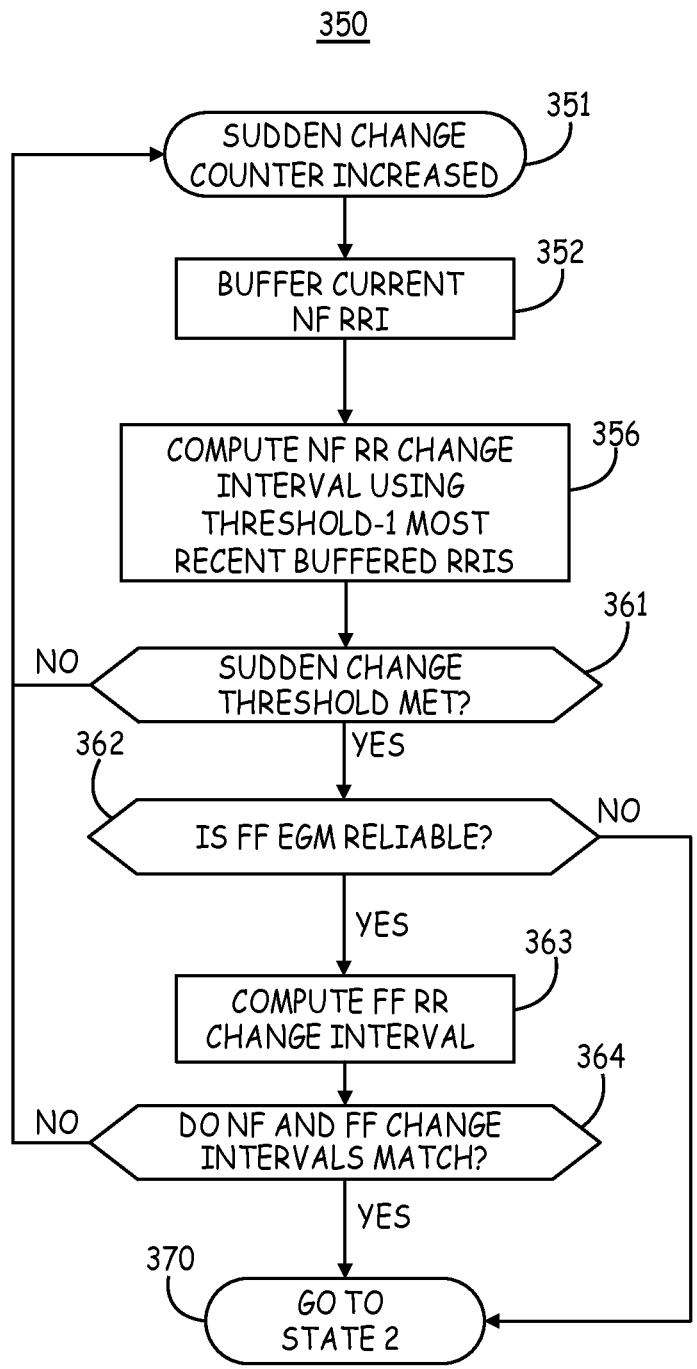
FIG. 9 is a flow chart of one method for comparing heart rate estimates obtained from two different sensing vectors for verifying a heart rate estimate when other sudden change detection criteria are met for transitioning from State 1 to State 2 of the detection algorithm.

FIG. 9 is a flow chart 350 of one method for comparing a NF HR and a FF HR for verifying a NF HR estimate when other sudden change detection criteria are met for transitioning from State 1 to State 2. The process shown in flow chart 350 may correspond to block 168 of FIG. 4, block 243 of FIG. 5, or block 288 in FIG. 7.

At block 351, a counter used for detecting a sudden change during State 1 is increased. The counter may be the Out of Range counter used to count RRIs falling outside an expected RRI range (LV mode) or the LV counter used to count RRI differences that are less than a LV threshold (HV mode). If a sudden change counter is increased, the current NF RRI which resulted in the increase is buffered at block 352. NF RRIs that contribute to a sudden change detection are buffered for use in determining a metric of the NF HR.

The method used to compute the metric of the NF HR from the buffered NF RRIs depends on the change detection threshold applied to the Out of Range counter or LV counter. If the sudden change detection threshold is X, X-1 buffered RRIs are used at block 356 to compute a NF HR estimate. The value X may be nominally 10 but may range, for example, between 6 and 16.

The NF HR estimate is referred to as the NF RR change interval in flow chart 350 and is measured as the average of two out of the X-1 buffered RRIs. For example, if the change detection threshold is set to 10, the sixth and seventh smallest RRIs out of the most recent 9 buffered RRIs may be averaged to compute the NF RR change interval.

If the sudden change threshold is met at block 361 (either the Out of Range counter or the LV counter reaches or exceeds the sudden change threshold), the FF EGM signal is used to verify the NF HR estimate computed as the NF RR change interval. As described previously, if the FF EGM signal is unreliable, as determined at block 362, the FF signal is not used to verify the NF HR estimate. A transition to State 2 may occur in response to the NF HR estimate and the sudden change detection.

If the FF EGM signal is reliable (block 362), the FF RR change interval is computed at block 363 as an estimate of HR. The FF RR change interval may be computed in a similar manner as the NF RR change interval, i.e. averaging selected RRIs out of the X-1 most recent FF RRIs. These intervals may be the X-1 most recent consecutive FF RRIs and not necessarily be FF RRIs that correspond in time to the buffered NF RRIs. When buffering the NF RRIs that cause an increase in a change counter, intervening RRIs that do not cause an increase in the change counter are not buffered and are not used for computing the NF RR change interval. As such, the NF RRIs used to compute the NF change interval may not be the most recent consecutive X-1 intervals. In an alternative embodiment, each time a NF RRI is buffered, the corresponding FF RRI may be buffered for use in computing the FF RR change interval.

At block 364, the NF and FF change intervals are compared to determine if the NF and FF heart rate estimates approximately match. If the NF and FF change intervals are within a predetermined threshold, e.g. approximately 20 ms of each other, the FF and NF heart rate estimates are determined to approximately match. The sudden change detection criteria are met, causing a transition to State 2 at block 370.

If the NF and FF change intervals do not approximately match at block 364, the detection algorithm remains in State 1. The process shown in FIG. 9 returns to block 351 to wait for the next increase in a sudden change counter.

Figure 10:
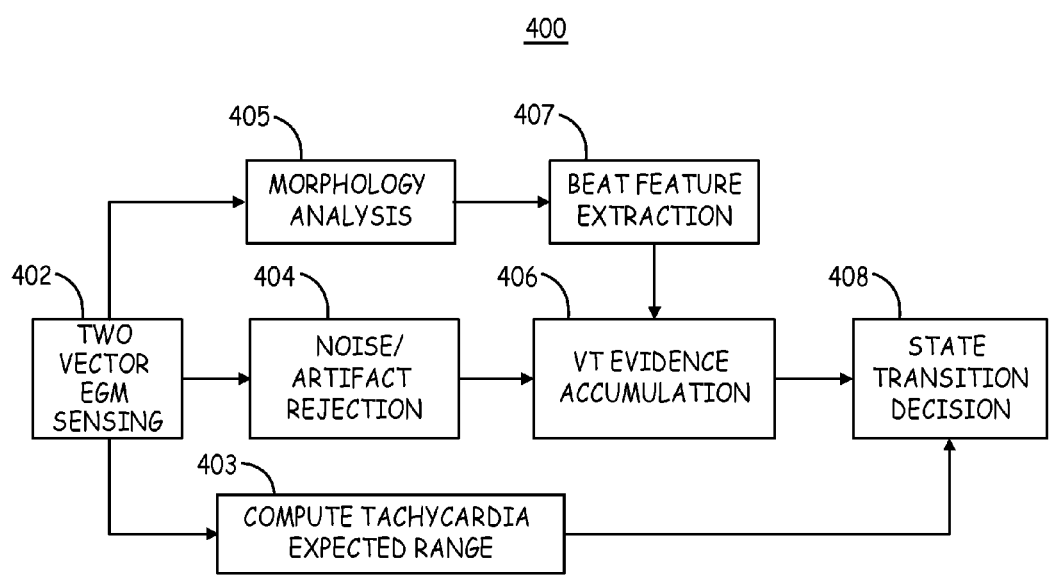
FIG. 10 is a flow chart providing an overview of operations performed during State 2 of the detection algorithm.

FIG. 10 is a flow chart 400 providing an overview of operations performed during the concerned State 2. The tachycardia detection algorithm continues to use simultaneously acquired EGM signals sensed from two different sensing vectors at block 402. The two sensing vectors are used for performing tachycardia detection operations including computing a tachycardia expected RRI range at block 403, rejecting noise/artifact at block 404, performing an overall signal morphology analysis at block 405, and for extracting specific beat features at block 407 for additional analysis when needed.

At block 403, a tachycardia expected range is computed from one of the EGM signals, e.g. the NF EGM signal. The tachycardia expected range is analogous to the expected RRI range used in State 1. The tachycardia expected range, however, represents an RRI range expected from the current, concerning rhythm, rather than in the preceding normal, unconcerning rhythm. Similar to the expected RRI range computed during State 1, the tachycardia expected range computation at block 403 may include computing RRMEAN and RRMAD values computed using a weighted sum of the current RRI and the previous RRMEAN and RRMAD values. The initial values of RRMEAN and RRMAD used to compute the tachycardia expected range may be set to nominal values, e.g. 500 ms, and quickly adjusted to actual values using the most recent five RRIs (or another number of RRIs).

The last expected RRI range computed in State 1 before transitioning to State 2 is stored and will not be updated during State 2. The State 1 expected RRI range is thus frozen during State 2 operations. The expected RRI range existing upon transition from State 1 to State 2 represents an expected HR upon return to a normal rhythm. As such, the expected RRI range value upon transitioning to State 2 is stored for use in controlling a transition back to State 1 as will be described in detail below.

At block 404, a noise/artifact rejection process is performed which analyzes each of the FF and NF EGM signals to determine the presence of noise or artifact that may corrupt the tachycardia discrimination algorithm. Each heart beat will be given a noise/artifact classification to exclude corrupted beats from contributing to the tachycardia discrimination methods. Various methods for detecting noise or artifact in the EGM signals may be used. One method for classifying a current beat as corrupted or non-corrupted is described below in conjunction with FIG. 18.

Each heart beat that is classified as a non-corrupted beat is analyzed morphologically at blocks 405 and 407 as needed. The results of an overall morphology analysis and specific beat feature analysis contribute in a cumulative manner on a beat-by-beat basis to a VT evidence metric at block 406. As will be described in detail herein, a VT evidence counter is adjusted beat-by-beat according to specific rules relating to an overall morphology analysis of the FF EGM signal and/or the NF EGM signal and/or specific beat features of the FF and/or NF EGM signals.

In some rhythms, changes in specific beat features as compared to a normal sinus rhythm beat, on either the FF or NF EGM signals, may have a higher tachycardia discrimination power than an overall morphology assessment of the same signal alone. As such, specific beat features are used to enhance the sensitivity and specificity of the tachycardia discrimination method.

At block 408, the tachycardia expected range and a VT evidence counter are used in a VT detection process to detect VT and advance to convinced State 3, or to make a determination to return to the unconcerned State 1. An expected RRI range stored from State 1 operations may be used in making a decision to return to State 1. If the VT evidence counter has reached a detection threshold, VT will be detected and a transition from the concerned State 2 to the convinced State 3 occurs. As will be described in detail below, criteria are defined to govern the transition between State 2 and State 3 and from State 2 back to State 1. The criteria may include requirements applied to results of the noise/artifact rejection analysis 404, VT evidence accumulation (block 406), the tachycardia expected range (block 403) and a stored expected RRI range from State 1.

Figure 11:
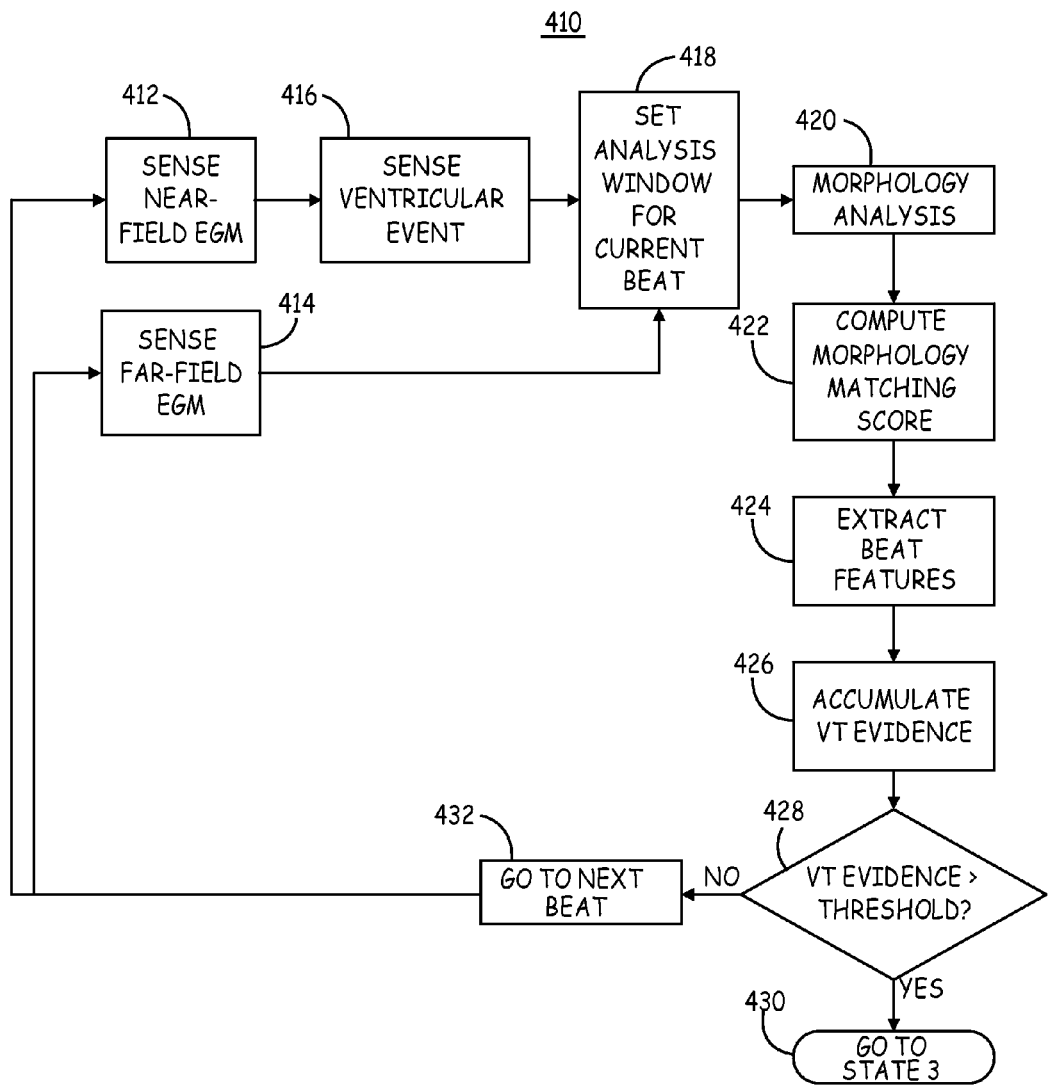
FIG. 11 is a flow chart of a method for discriminating between VT (treatable) and SVT (non-treatable) rhythms during State 2 operations.

FIG. 11 is a flow chart 410 of a method for discriminating between VT (treatable) and SVT (non-treatable) rhythms during State 2 operations. In general, when the estimated HR is greater than a tachycardia detection lower rate limit but less than an SVT detection upper rate limit, the current heart rhythm is classified as "non-treatable" unless proven otherwise by the accumulation of VT evidence on a beat-by-beat basis. At blocks 412 and 414, two different EGM sensing vectors are employed for simultaneously recording two different EGM signals, e.g. the FF and NF EGM signals described above.

In one embodiment, a NF signal sensed at block 412 is used at block 416 for sensing ventricular events, i.e. R-waves. Upon sensing a ventricular event at block 416, an analysis window is set at block 418 defining an interval for analyzing both the FF and NF EGM signal for the sensed heart beat. While the NF EGM signal may be used to set the analysis window based on NF sensed events, the analysis window may be applied to both the NF signal and the FF signal for purposes of waveform morphology analysis and extracting specific beat features. In other embodiments, separate analysis windows may be set and applied to the EGM signals based on events sensed from the respective EGM signal.

At block 420, morphology analysis of the FF EGM signal within the analysis window is performed. This analysis is referred to as an "overall" morphology analysis because the morphology of the entire EGM signal within the analysis window is compared to the morphology of an EGM template obtained over a similar time window. In other words a specific amplitude, slope, or other time point within the analysis window is not isolated for analysis when performing the overall morphology analysis. The morphology of the waveform as a whole during the analysis window is compared to a known template morphology as a whole to determine a degree of matching between the unknown beat and the known template. The analysis window generally encompasses at least the QRS complex but may include more or less of the EGM signal depending on the analysis window duration and accuracy of R-wave detection.

Numerous morphology analysis algorithms are available which may be applied at block 420. In general, a morphology analysis is performed to compare the overall morphology of a sensed EGM signal during the analysis window of an unknown beat to the morphology of a known heart beat for use in classifying the unknown beat. For example, in Wavelet analysis, the morphology of the FF EGM signal is compared to a known template for a normal sinus rhythm beat to determine if the R-wave signal matches the normal sinus rhythm template. Reference is made to U.S. Pat. No. 6,393,316 (Gillberg et al.), incorporated herein by reference in its entirety.

A morphology matching score is computed at block 422 as a measure of how closely the overall morphology of the sensed EGM signal of an unknown beat matches the overall morphology of a known template of a normally conducted beat. A high matching score generally indicates that the unknown sensed ventricular beat is a conducted beat arising from the atrial chambers. A low matching score generally indicates that the sensed ventricular beat is not a normally conducted beat and originates in the ventricular chambers.

In past practice, VT detection algorithms compared a morphology score to a threshold and the sensed heart beat was classified accordingly. For example, in a Wavelet morphology analysis, a VT beat threshold may be set such that if the wavelet matching score falls below the threshold, the unknown beat is classified as a VT beat. If the matching score exceeds the threshold, the unknown beat is classified as an SVT beat. VT or SVT is detected based on this threshold-based classification of the morphology matching score.

In some cases, however, the overall matching score may fall very close to a selected threshold value. An overall morphology matching score may not be sensitive enough to subtle changes in the EGM signal that occur during some types of VT beats. As a result, a beat may be classified as an SVT beat when it is actually a VT beat, or vice versa, when a fixed threshold boundary is used for separating VT and SVT beats based on an overall morphology matching score. In clinical practice, there can be significant overlap of the morphology scores for VT and SVT beats which can result in missed detection of VT or false detection of VT.

As such, during State 2 operations, additional analyses of specific beat features are used in addition to the overall morphology matching score for accumulating VT evidence. At block 424, additional beat features are extracted from the EGM signal for the given heart beat. Selected beat features are analyzed to improve the sensitivity and accuracy of SVT/VT discrimination. These beat features are referred to herein as "specific" beat features in that these features take a "closer look" at the EGM signal than the overall morphology score. Specific beat features may be isolated features of the EGM waveform, e.g., relating to amplitude, slope, or other waveform characteristics, occurring at a specific time point or a sub-interval within the analysis time window set at block 418. In some embodiments, if the FF EGM signal is used to obtain the overall morphology score, specific beat features may include features that are more spatially localized than the FF EGM signal. For example, an overall morphology score of the NF EGM signal, taken across the same analysis window as the FF overall morphology score, may be considered a more specific beat feature than the FF overall morphology score because the NF EGM signal is a more spatially localized signal than the FF EGM signal. As such, specific beat features are features of an EGM signal that are temporally or spatially more isolated or localized than an overall morphology score obtained from an EGM signal across the full duration of a selected analysis time window.

The specific beat features extracted at block 424 are selected based on the overall morphology matching score result computed at block 422. Specific beat features extracted at block 424 may correspond to beat morphology parameters generally described in commonly-assigned U.S. patent application Ser. No. 12/415,445, hereby incorporated herein by reference in its entirety. Beat features may be extracted from the NF EGM signal, the FF EGM signal, or a combination of both. Rules are applied to the overall morphology matching score and the specific beat features to accumulate evidence of VT on a beat-by-beat basis by increasing or decreasing a VT evidence counter at block 426 as will be described in detail below.

If the VT evidence counter exceeds a treatable rhythm detection threshold at block 428, a transition to the convinced State 3 occurs at block 430. In various embodiments, additional criteria applied to RRI data must be satisfied in order to make the State 3 transition at block 430. If the VT evidence count does not exceed a detection threshold, the process advances to the next heart beat at block 432 by returning to blocks 412 and 414 to continue sensing the NF and FF EGM signals.

Figure 12:
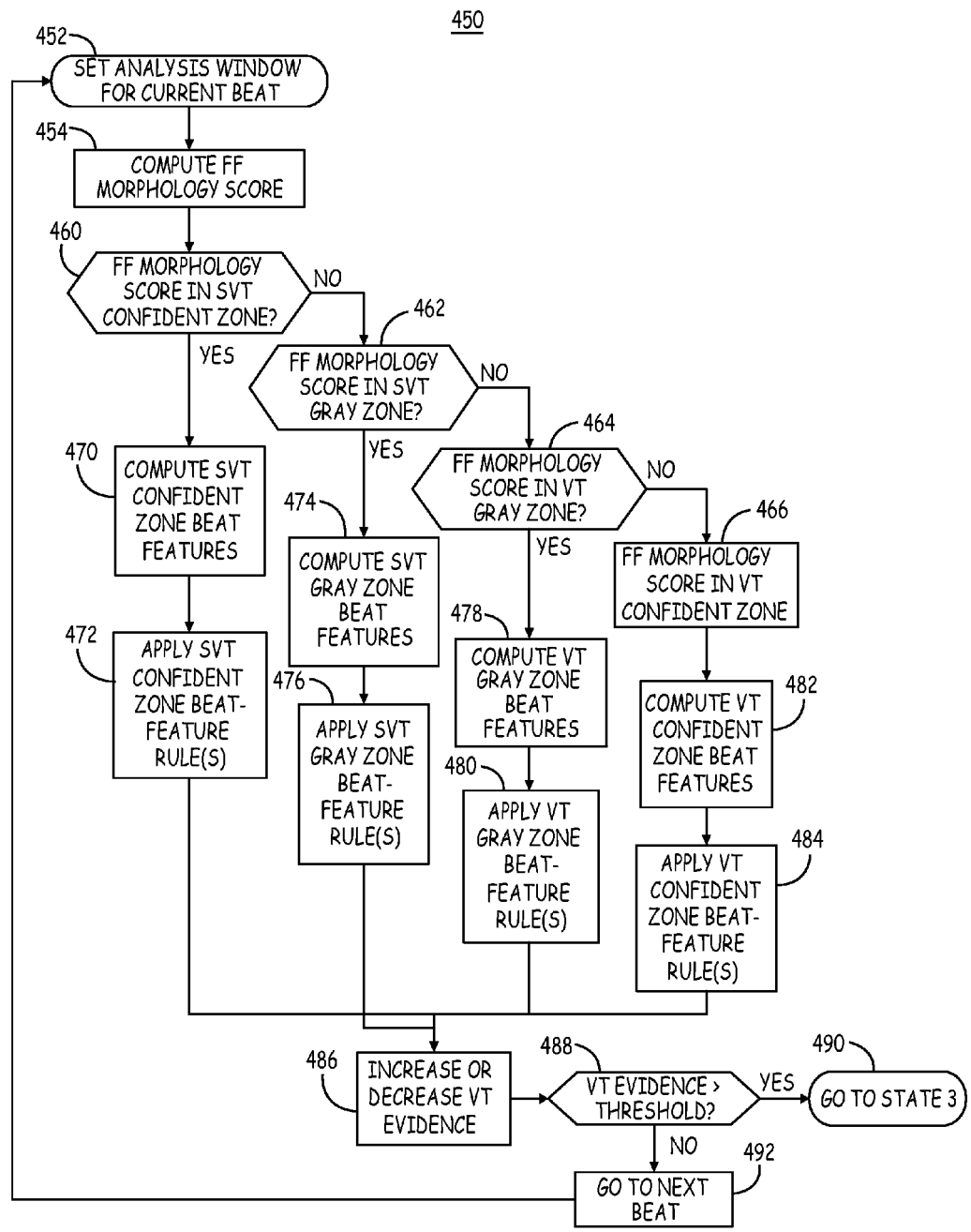
FIG. 12 is a flow chart of one method for extracting specific beat features and accumulating VT evidence on a beat-by-beat basis.

FIG. 12 is a flow chart 450 of one method for extracting specific beat features and accumulating VT evidence on a beat-by-beat basis. At block 452, the analysis window for the current heart beat is set based on a NF sensed event. At block 454, the FF EGM signal is analyzed using a desired morphology analysis method, such as Wavelet analysis. A morphology matching score may be computed as a measure of the overall match between the FF EGM signal during the analysis window to a morphology template for a normally conducted beat, i.e. a sinus beat. A FF overall morphology matching score (FFMS) is computed at block 454.

At blocks 460 through 466, the FFMS is compared to different confidence zones for tachycardia discrimination. Multiple zones may be defined including, as shown in flow chart 450, an SVT confident zone (block 460), an SVT gray zone (block 462), a VT gray zone (block 464) and a VT confident zone (block 466). Assuming a possible morphology matching score of 100, indicating an exact match within the resolution of the analysis method between an unknown beat and a stored template for a normally conducted beat, an SVT confident zone might be defined as any score greater than 85. An SVT gray zone might be defined as a score equal to or less than 85 but greater than or equal to 70. A VT gray zone might be defined as a score less than 70 but greater than or equal to 40, and a VT confident zone includes any score less than 40. Other thresholds may be defined for separating the FFMS zones depending on the morphology matching algorithm being used, clinical data relating to the confidence levels of morphology scores, clinician preference or other factors.

Depending on the zone that the FFMS score falls into, as determined at decision blocks 460 through 466, specific beat features may be measured or computed from the EGM signals at a respective blocks 470, 474, 478 and 482. The additional specific beat features that are computed are those needed for applying respective beat feature rules at subsequent blocks 472, 476, 480 or 484. The additional beat features extracted and the beat feature rules applied according to the morphology matching score zone of the current FFMS are selected to enhance the sensitivity and/or specificity of the tachycardia detection algorithm. The FFMS and/or specific beat features will be used to either increase or decrease a VT evidence counter at block 486 according to which rules are applied at blocks 472 through 484 and found to be true.

The VT evidence counter is increased or decreased at block 486 in response to the outcome of the applied beat feature rule(s). The influence of the FFMS on the accumulation of VT evidence on a beat-by-beat basis can be effectively increased or decreased based on which beat feature rule(s) "fire", i.e., are found true.

If the FFMS falls into an SVT confident due to a high match between the unknown beat and a normal beat template, additional SVT confident zone beat features are extracted at block 470. The specific beat features extracted are those that will be needed for applying the SVT confident zone beat feature rule(s) at block 472.

The SVT confident zone beat feature(s) may be any feature extracted from the FF and/or NF EGM signal during the analysis window and may include a morphology matching score determined from a comparison of the NF EGM signal of the current unknown beat to a known NF EGM template.

The SVT confident zone beat feature rule applied at block 472 may include threshold comparisons or other criteria which associate the extracted beat feature(s) to either an SVT beat or a VT beat. In one embodiment, the SVT confident zone beat feature rule(s) are defined to identify evidence of VT that would contradict the finding of the FFMS being in the SVT confident zone. If the rule is satisfied, the VT evidence counter is adjusted accordingly at block 486.

Figure 13A:
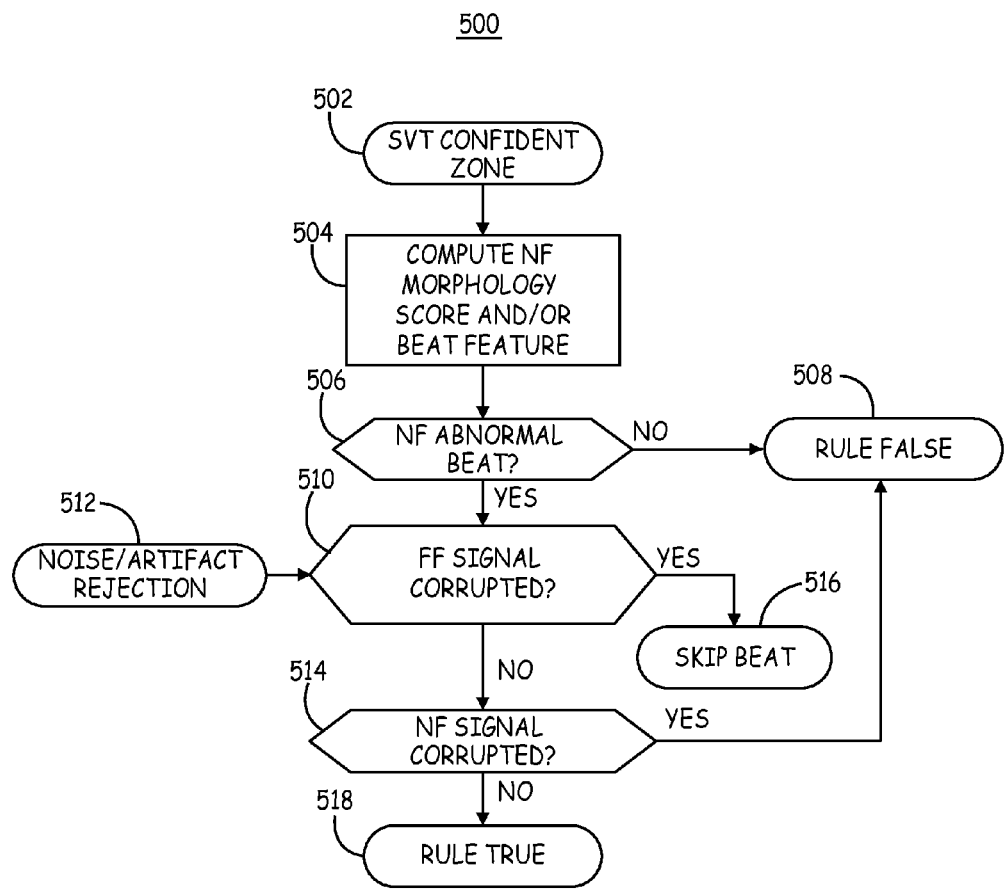
FIG. 13A is a flow chart of the application of an SVT confident zone beat-feature rule.

FIG. 13A is a flow chart 500 of the application of an SVT confident zone beat-feature rule. In one embodiment, a rule for detecting evidence of an abnormal (VT) beat using the NF EGM signal is applied whenever the FFMS falls into the SVT confident zone. As such, when the FFMS falls into the SVT confident zone (block 502), a NF morphology matching score (NFMS) is computed at block 504 for the NF EGM signal within the analysis window. Additionally or alternatively, specific beat features of the EGM signals may be computed or measured at block 504. Any examples of specific beat features described herein may be used in applying a NF abnormal beat rule in the SVT confident zone.

At block 506, the NFMS is compared to VT and SVT detection zones, which may be defined the same or similarly to the FFMS detection zones. If the NFMS falls into a zone corresponding to VT, this finding is evidence of an abnormal beat. This finding based on a "closer look" at the cardiac signals contradicts the result of the overall FFMS falling into the SVT confident zone. In other embodiments, specific beat features of the FF and/or NF signals may be extracted and compared to normal template values of the respective features for detecting evidence of a VT beat.

Before declaring the NF Abnormal beat rule to be true at block 518, the FF and/or the NF EGM signals may be examined for noise/artifact corruption. The results of the noise/artifact rejection process (block 512) are used to determine if the FF and NF EGM signals are non-corrupted signals at decision blocks 510 and 514, respectively. Numerous noise/artifact detection algorithms may be employed for classifying a heart beat or an EGM strip as noise or artifact contaminated. In one embodiment, if the FF signal is found to be corrupted at block 510, the current beat is skipped at block 516. The VT evidence counter is not adjusted for the current beat.

If the FF signal is not corrupted, but the NF signal is found to be corrupted (block 514), the NF abnormal beat rule is declared false at block 508. The NF signal is not used to corroborate or contradict the FFMS result. If the FF and NF EGM signals are not corrupted by noise or artifact, the rule is found true at block 518. This result in combination with the FFMS result is used to adjust the VT evidence counter.

Referring again to FIG. 12, the VT evidence counter is adjusted at block 486 based on the outcome of the NF abnormal beat rule and the FFMS. Generally, the VT evidence counter will be decreased in response to the strong evidence of an SVT beat based on the FFMS alone. However, the size of the decrement of the VT evidence counter may be smaller when the NF abnormal beat rule is true. Evidence of an abnormal beat in the NF EGM signal reduces the confidence of the unknown beat being an SVT beat based on the FFMS alone.

In an illustrative embodiment, the VT evidence counter may be decreased at block 486 according to the following process when the FF EGM morphology score falls into the SVT confident zone:

IF NF abnormal beat rule is true, VT evidence is decreased by 0.5
      ELSE VT evidence is decreased by 2.0
      END The VT evidence counter is decreased because the FF EGM score was high enough to fall into the SVT confident zone. The VT evidence counter is decreased by a smaller amount, however, when a NF Abnormal Beat rule is found to be true and neither of the FF and NF signals is noise contaminated.

If a NFMS or other specific beat feature(s) are found to be "normal", i.e. corresponding to a beat that is supraventricular in origin, the NF EGM analysis corroborates the FFMS result. The NF Abnormal beat rule would be found false, and the VT evidence counter would be reduced from a current value (or remain at a zero value) based on this evidence. If, however, a specific beat feature is "abnormal", i.e. possibly indicating a beat that is ventricular in origin, this evidence contradicts the FFMS and effectively reduces the confidence that the beat is an SVT beat. In this case, the VT evidence counter may still be reduced but by a smaller decrement than when both the specific beat feature result and the overall morphology score support a common finding that the current beat is an SVT beat.

If the FFMS falls in the SVT gray zone (as determined at block 462), SVT gray zone beat features are computed at block 474. In this case, specific beat features are extracted that might provide evidence of a VT beat, contradictory to the FFMS result that the beat is an SVT beat. Such contradictory evidence may include a very low NFMS, large differences in specific NF beat features as compared to a corresponding normal template feature, and/or large differences in specific FF beat features relative to a normal template feature.

SVT gray zone beat features may include specific features of NF and/or FF signals. In one embodiment, the SVT gray zone beat features extracted at block 474 include a maximum slope, an R-wave width, an R-wave symmetry index (ratio of the upslope to the downslope of the R-wave), and a QR index (ratio of the Q-wave amplitude to the R-wave amplitude). Other features that could be included in various embodiments include R-wave polarity consistency between the FF and NF signals and/or template R-wave polarity, time difference between NF and FF peak amplitudes, and time difference between NF and FF maximum slopes. It is recognized that numerous specific beat features could be selected. The beat features found to have the highest discriminatory power between SVT and VT beats will be selected for use in applying rules for increasing and decreasing the VT evidence counter on a beat-by-beat basis. Features that are not found to improve the sensitivity or specificity of the tachycardia discrimination algorithm may be ignored.

Rules are applied at block 476 to improve the sensitivity of the discrimination algorithm to VT. The rules examine specific beat features for evidence of a VT beat that would increase the VT evidence counter at block 486, rather than decreasing it based on the FFMS result falling into the SVT gray zone.

Figure 13B:
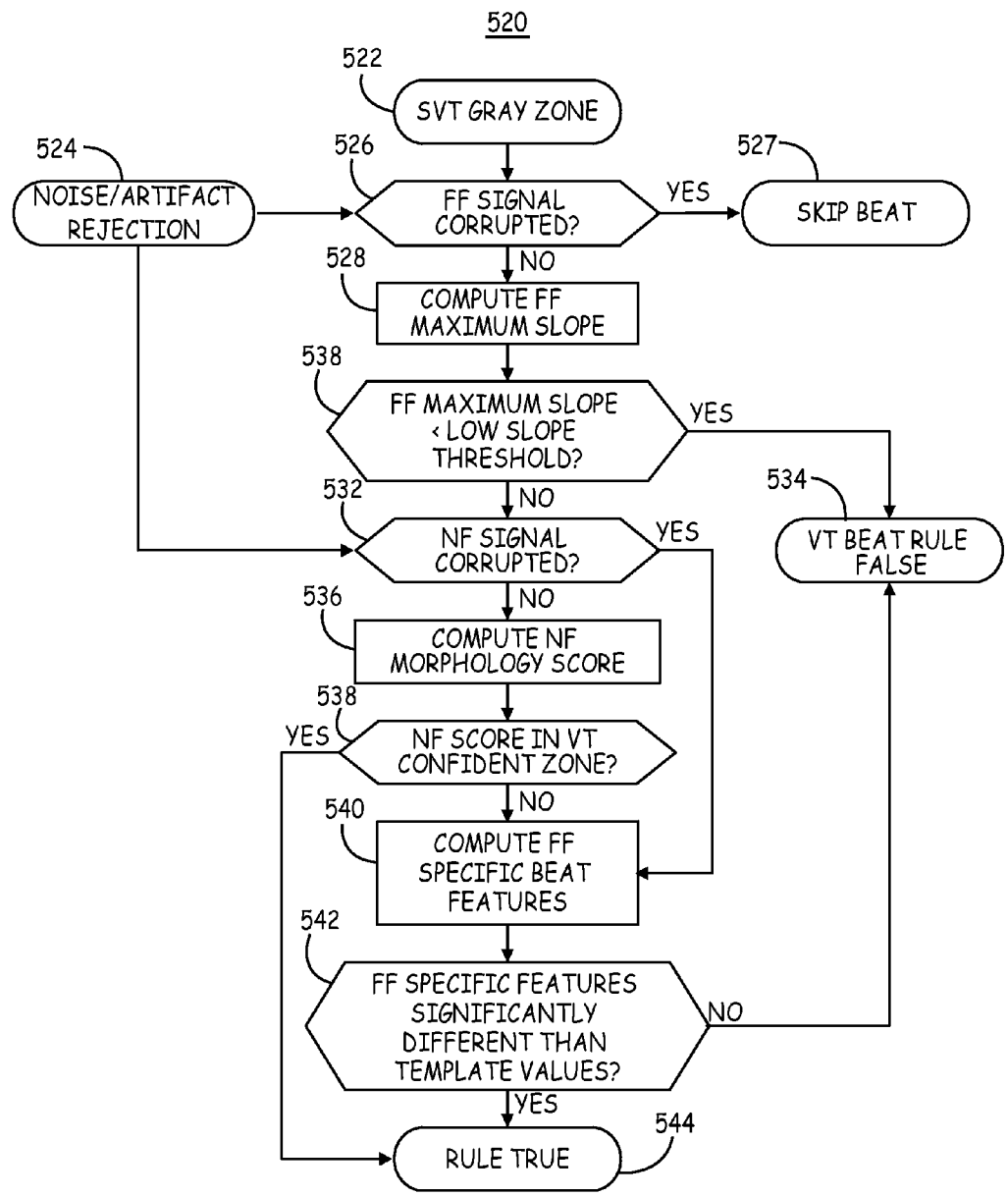
FIG. 13B is a flow chart of one method for applying a VT beat rule when an overall morphology score falls into the SVT gray zone.

FIG. 13B is a flow chart 520 of one method for applying a VT beat rule when the FFMS falls into the SVT gray zone. If the FFMS falls into the SVT gray zone (block 522), the noise/artifact rejection result (block 524) for the FF signal is checked at block 526. Additional analysis of specific beat features is not performed if the FF signal is corrupted. The entire beat is skipped at block 527, and no adjustment to the VT evidence counter will be made.

If the FF signal is not corrupted, a FF maximum slope is computed at block 528. If the absolute value of the maximum slope of the FF EGM signal during the analysis window is less than a low slope threshold (decision block 538), additional analysis is not performed. FF EGM signal may not be of adequate signal strength to assess specific beat features when the maximum slope of the FF EGM signal is below a threshold value. The VT beat rule is false (block 534).

If the FF signal is not corrupted and meets a minimum slope requirement, additional specific beat features are analyzed to detect evidence of VT within the current beat. Either or both of the NF and FF signals may be used for performing additional analysis for detecting evidence of VT.

For example, if the NF signal is determined to be non-corrupted (block 532) based on input from the noise/artifact rejection algorithm (block 524), the NFMS may be computed at block 536. If the NFMS falls in the VT confident zone, i.e. a very low match between the NF EGM signal and a known normal beat template, the VT beat rule fires true at block 544. This evidence of VT in the current beat will be used in adjusting the VT evidence counter.

If the NF EGM signal is corrupted (block 532), or if the NF overall morphology score is greater than the VT confident zone (block 538), additional analysis of specific beat features extracted from the FF signal may be performed to detect possible evidence of VT in the current beat. FF specific beat features are measured or computed at block 540 and compared to respective specific beat features measured or computed from a FF normal beat template at block 542. If any FF specific beat features are significantly different than the template beat features, evidence of VT is detected in the current beat.

In one embodiment, the FF R-wave width, FF R-wave symmetry, and FF ratio of Q-wave amplitude to R-wave amplitude, also referred to herein as QR index, are each compared to the respective feature of a FF normal beat template. A threshold difference between any one of the FF specific beat features and the FF normal beat template will cause the VT beat rule to fire at block 544.

In summary, if the FF signal is corrupted, the entire beat is skipped for VT evidence adjustment. If the FF signal is not corrupted but does not meet a minimum slope requirement, no additional analysis for detecting evidence of VT is performed. The VT evidence metric is adjusted based on the FFMS at block 486 of FIG. 12. However, if the FF signal is not corrupted and does meet a minimum slope requirement, specific beat features are examined. The selected beat features may be any features that are known to be altered during a VT beat but perhaps not enough to cause the overall FFMS to fall into a VT zone. If the FF beat features are not found to meet VT evidence criteria, the NF EGM signal may still be used to detect evidence of VT in the current beat. If the NF signal is not corrupted and results in a NFMS in the VT confident zone, this evidence of VT will be used against the FFMS result in adjusting the VT evidence counter.

In the illustrative embodiment, specific beat features are not extracted from the NF EGM signal for examining for evidence of VT when the overall NFMS is very low. However, it is to be understood that in alternative embodiments, specific beat features from the NF EGM signal may be examined for evidence of VT. For example, if the NFMS is higher than the VT confident zone, but still within a gray zone, specific NF beat features may be examined for identifying features indicative of VT. Furthermore, if the NFMS falls into an SVT zone (gray or confident), corroborating the FFMS result, the process shown in FIG. 13B may advance directly to block 534 to adjust the VT evidence counter based on the FFMS without further analysis of specific FF beat features.

Referring again to block 486 of FIG. 12, the VT evidence counter is adjusted according to whether the VT beat rule is satisfied or not at block 476. If the VT beat rule is true, then the VT evidence counter is increased at block 486 by a predetermined increment. If the VT evidence rule is not true, i.e. no evidence of an abnormal beat is found based on the additional examination of the FF and/or NF signals, the VT evidence count is decreased due to the FFMS falling into the SVT gray zone. In this case, the VT evidence count is decreased by a decrement that is less than the decrement used to decrease the VT evidence metric when the FFMS falls into the SVT confident zone and there is no evidence of an abnormal beat in the NF signal.

The following process may be used to adjust the VT evidence count when the FF overall morphology score falls into the SVT gray zone:
IF VT beat rule is TRUE, increase VT evidence by 0.625
ELSE decrease VT evidence by 0.5
END The specific values for the increments and decrements applied to the VT evidence count provided herein are illustrative and may be adjusted to provide optimal sensitivity and specificity of the discrimination algorithm. Furthermore, it is recognized that numerous variations and substitutions of the specific beat features and combinations thereof may be employed for use in detecting evidence of VT when a FFMS falls into the SVT gray zone.

If the FFMS falls into the VT gray zone (block 464), specific beat features are computed at block 478, which are needed for applying VT gray zone beat feature rules at block 480. Additional specific beat features are extracted that provide evidence that the current beat is more likely to be a normally conducted (SVT) beat than a VT beat, in contradiction to the FFMS result. Additionally or alternatively, analysis may be performed to detect supporting evidence that the current beat is highly likely to be a VT beat to support the FFMS result.

The specific beat features may be computed from the FF and/or NF EGM signals and compared to respective template features for a normal beat. In one embodiment, a FF normal beat rule is applied at block 480 for detecting evidence of normal beat features in the FF signal that would contradict the FF overall morphology score in the VT gray zone. A second rule, a NF normal beat rule, may also be applied at block 480 for detecting evidence of normal beat features or overall morphology in the NF signal, which would contradict the FF overall morphology matching score and impact the subsequent adjustment of the VT evidence counter.

Beat features computed at block 478 needed for applying a normal beat rule at block 480 may include any features listed herein, including but not limited to the maximum slope, R-wave polarity, R-wave width, R-wave symmetry index, ratio of the Q-wave to the R-wave amplitudes, amplitude peak shift measured as the time difference between the absolute maximum amplitudes of the FF signal and the NF signal, and slope peak shift measured as the time difference between the absolute maximum slope of the FF signal and the absolute maximum slope of the NF signal.

Figure 13C:
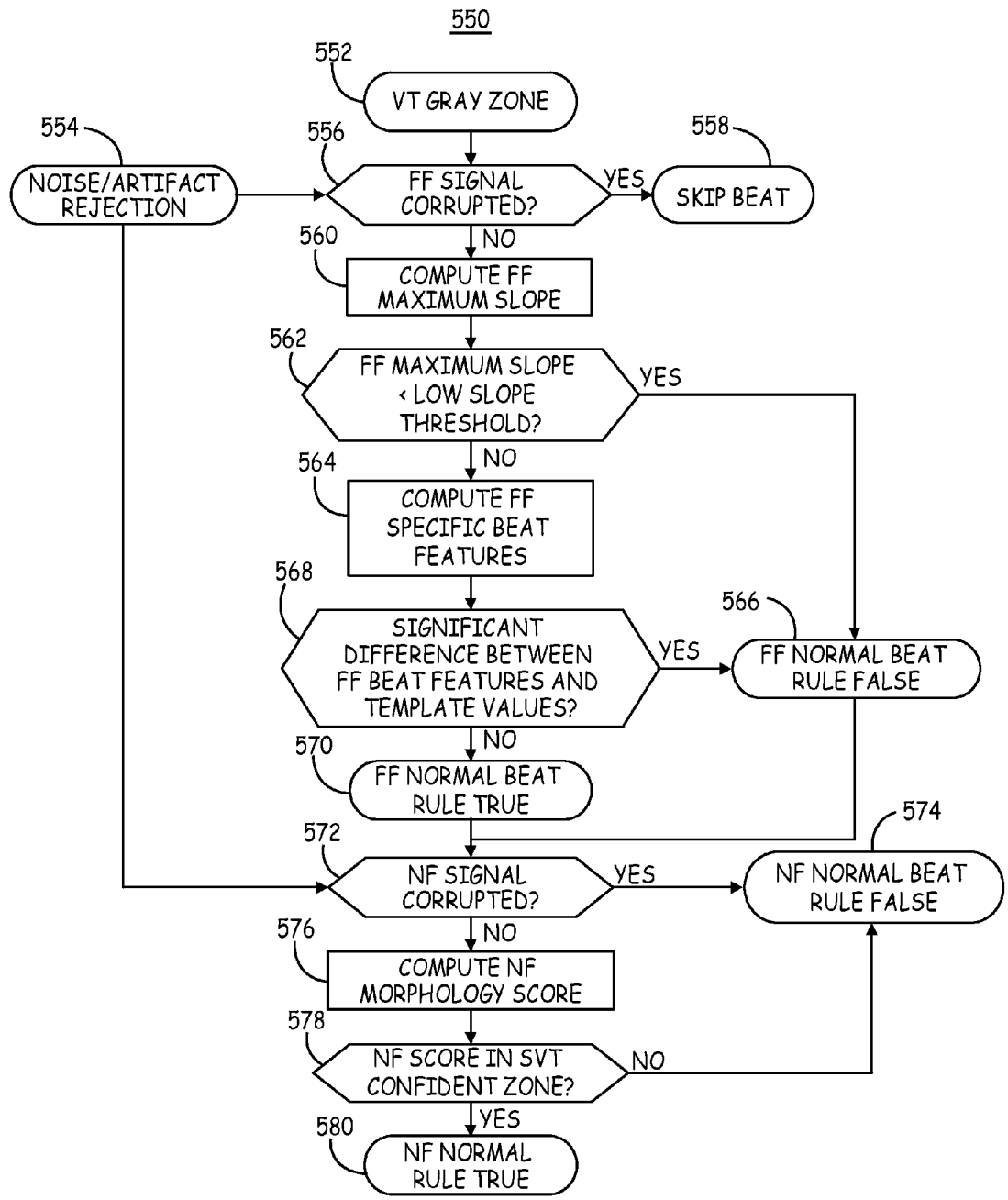
FIG. 13C is a flow chart of one method for applying VT gray zone rules.

FIG. 13C is a flow chart of one method for applying VT gray zone rules. When the FFMS falls in the VT gray zone (block 552), the results of the noise/artifact rejection algorithm (block 554) are checked to determine if the FF signal is corrupted (at block 556). If the FF signal is corrupted, the entire beat is skipped with no adjustment to the VT evidence counter as indicated at block 558.

If the FF signal is not corrupted, the FF maximum slope during the analysis window is computed at block 560 and compared to a low slope threshold at block 562. If the FF maximum slope is less than the low slope threshold, no further analysis of FF specific beat features will be performed. The FF normal beat rule is false (block 566). The process of applying VT gray zone rules proceeds to block 572 to apply a NF normal beat rule as will be described further below.

If the FF maximum slope exceeds a low slope threshold (block 562), FF specific beat features are computed at block 564. FF specific beat features may include any beat features listed previously herein. The specific beat features used by the FF normal beat rule are selected as those that may provide evidence that the current beat is likely to be an SVT beat, rather than a VT beat as suggested by the FFMS. The specific beat features are compared to respective beat features of a FF normal beat template at block 568.

The FF normal beat rule may require that one or a combination of two or more specific beat features be within a predefined threshold or range of the respective FF normal template feature in order to declare evidence of an SVT beat. In one embodiment, the FF normal beat rule is declared true at block 570 if the FF QR index, FF R-wave width, and FF R-wave symmetry index are all within a respective range of the corresponding FF normal template feature. If any one FF specific beat feature does not meet a normal beat requirement, the FF normal beat rule is false (block 566). In other embodiments, the FF normal beat rule may include "OR" operators that allow the rule to be satisfied if at least one or some specific beat features are found to approximately match a normal beat template.

When the FF normal beat rule is satisfied, there is conflicting evidence from the FF overall morphology score, which fell into the VT gray zone, and the specific beat features which provide evidence of SVT. This contradictory evidence will influence the adjustment of the VT evidence counter at block 486 of FIG. 12, as will be described below.

In addition to the FF normal beat rule, a NF normal beat rule may be applied to further examine the NF EGM signal for evidence of SVT. As such, after determining if the FF normal beat rule is true or false (block 566 or 570), the NF signal is checked to determine if the signal is corrupted at block 572, using the results of the noise/artifact rejection algorithm (block 554). If corrupted, no further analysis of the NF signal is performed. The NF normal beat rule is false (block 574). The NF signal is not considered reliable for detecting evidence of an SVT beat that would contradict the FFMS.

If the NF signal is not corrupted, the NFMS is computed at block 576. If the NFMS is very high, e.g. within an SVT confident zone as determined at block 578, the NF normal beat rule fires true (block 580). The high NFMS is detected as evidence of a normally conducted beat originating in a supraventricular region of the heart. In other embodiments, the NF normal beat rule may include comparisons of NF specific beat features to respective features of a NF normal template.

Referring again to FIG. 12, the VT evidence counter is adjusted at block 486 according to the results of applying the VT gray zone rules. If neither of the FF normal beat rule nor the NF normal beat rule is true, then the VT evidence counter is increased by a predetermined increment in response to the FFMS falling within the VT gray zone. If the FF signal is corrupted, the entire beat is skipped for VT evidence adjustment.

If one or both of the FF normal beat rule or the NF normal beat rule are found to be true, the VT evidence counter may be increased by a smaller increment or decreased depending on the strength of the evidence of an SVT beat. One example of the process used at block 486 to adjust the VT evidence counter after applying VT gray zone rules is:
IF FF normal beat rule TRUE, decrease VT evidence by 0.375

ELSEIF NF normal beat rule TRUE, decrease VT evidence by 0.5

ELSE increase VT evidence by 0.75.

In this example, the VT evidence is increased only if the FF and NF normal beat rules are false. If the FF normal beat rule is true, the VT evidence counter is decreased by a relatively small decrement due to the evidence of an SVT beat found in the FF specific beat features. The FF specific beat features evidencing an SVT beat are given greater weight than the FFMS falling in the VT gray zone in accumulating VT evidence for the current beat.

If the NF normal beat rule is true, the VT evidence counter is decreased by a somewhat larger decrement than if the FF normal beat rule is true. The NF signal evidence for an SVT beat is considered to be stronger evidence of an SVT beat than the FF specific beat feature evidence for an SVT beat and stronger evidence of the correct beat classification than the FFMS being in the VT gray zone. It is recognized that the specific increments and decrements may be given different values in various embodiments.

The VT evidence metric is adjusted only once for the current beat. In some embodiments, multiple rules may be applied and the adjustment may be made based on a single rule considered to have the greatest confidence in correctly identifying the origin of the current beat. In other embodiments, the rules may be applied in a hierarchical manner. The first rule that fires is used to determine the increment or decrement applied to the VT evidence counter. The highest rule that fires is considered to have the greatest confidence in discriminating VT and SVT. In still other embodiments, a net adjustment to the VT evidence counter may be determined as a summation of the respective increments or decrements associated with multiple rules firing for a given beat.

If the FFMS falls into the VT confident zone, as determined at block 466, VT confident zone beat features may be computed at block 482 as needed for applying VT confident zone rules at block 484. In this case, any rules being applied at block 484 may be defined for detecting possible evidence of an SVT beat that might contradict the finding based on the FFMS. For example, FF and/or NF specific beat features may be computed for applying a normal beat rule in the VT confident zone for detecting evidence indicating that the beat is a normally-conducted SVT beat. The VT evidence counter may be increased in response to the FFMS falling into the SVT confident zone. The increment applied to the VT evidence counter, however, may be reduced if a normal beat rule fires true based on one or more specific beat features, including a NFMS or any other features described herein.

In other embodiments, the VT evidence counter may be adjusted directly at block 486 when a FFMS falls into a confident zone, either the SVT confident zone or the VT confident zone. For example, if the FFMS is very low, i.e. in a VT confident zone, the VT evidence counter may be immediately increased by one (or another increment) at block 486 without extraction of specific beat features and application of beat feature rules. The increment applied to the VT evidence counter in this case is larger than when the FFMS falls into the VT gray zone due to the higher confidence of a VT beat. Likewise, when the FFMS is very high and falling into an SVT confident zone, the VT evidence counter may be immediately decreased without further analysis of beat features. Rules involving specific beat features to improve the sensitivity and specificity may be applied in "gray" zones only that encompass mid-ranges of the possible range of an overall morphology score.

At block 488, the VT evidence count is compared to a threshold value for detecting VT. If the VT evidence count reaches a detection threshold, a transition to the convinced State 3 occurs at block 490. If the detection threshold has not been reached, the algorithm advances to the next beat at block 492 and returns to block 452 to continue accumulating VT evidence as long as other criteria for remaining in State 2 are satisfied.

Figure 14:
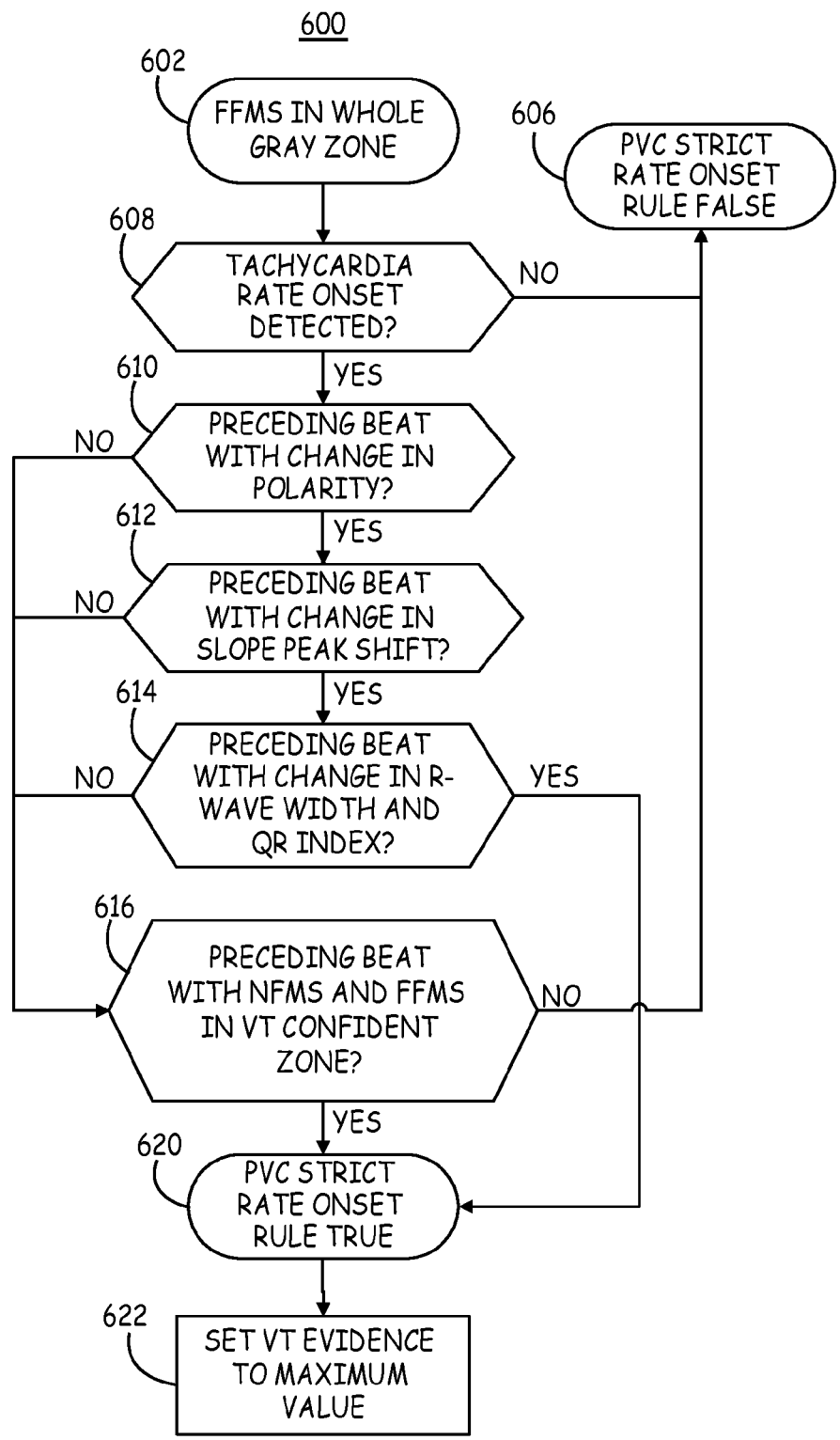
FIG. 14 is a flow chart of a method for applying rules across multiple overall morphology score gray zones.

FIG. 14 is a flow chart 600 of a method for applying rules across multiple FFMS gray zones. In addition or alternatively to the zone-specific rules applied at blocks 472, 476, 480 and 484 of FIG. 12, other rules may be applied across multiple morphology score zones. For example, rules may be defined which are applied across the entire gray zone, i.e. the SVT gray zone and the VT gray zone, or across the entire VT zone, i.e. the VT gray zone and the VT confident zone, or across the entire SVT zone, i.e. the SVT gray zone and the SVT confident zone. These rules may examine specific beat features that are considered strong evidence of either SVT or VT beat characteristics. If these rules are found to be true, these rules may override any single zone rules in adjusting the VT evidence counter.

If the FFMS falls into either of the SVT or VT gray zones (whole gray zone), as indicated at block 602, additional EGM signal analysis is performed to detect the particular situation of VT being initiated by a premature ventricular contraction (PVC) resulting in the onset of the tachycardia rate. Details regarding detection of rate onset are described in U.S. patent application Ser. No. 12/430,301, hereby incorporated herein by reference in its entirety. Briefly, the variability of n most recent RRIs and the relative change between the sum of those n most recent RRIs and the preceding n RRIs are examined to detect tachycardia rate onset. When the variability is less than a variability threshold and the relative change is greater than a relative change threshold, the current beat is detected as the tachycardia rate onset beat.

An initiating beat may be several beats earlier, for example approximately 4 to 6 beats earlier, than the tachycardia rate onset beat. If an earlier beat preceding the tachycardia rate onset beat is a PVC, the tachycardia is highly likely to be a VT initiated by a PVC. As such, for any FFMS falling into the whole gray zone, a PVC strict rate onset rule is applied to enhance sensitivity of the algorithm for detecting VT.

If tachycardia rate onset is detected for a current beat at block 608, e.g. according to the methods described in the commonly assigned '301 U.S. patent application, a preceding beat is checked for characteristics that would indicate that the preceding beat that is ventricular in origin. A single preceding beat may be examined, such as the fourth beat earlier than the current RRI. In alternative embodiments, one or more preceding beats may be examined for evidence that an initiating PVC has occurred within several beats prior to the tachycardia rate onset detection.

At blocks 610 through 614, multiple specific beat features of a preceding beat are compared to the respective beat features of a normal template. In the illustrative embodiment, all of these beat features are required to be significantly different than the normal beat template in order to determine that the beat has a high likelihood of being a PVC, initiating the tachycardia rate.

The specific beat features examined at blocks 610 through 614 may vary between embodiments. In the flow chart 600, the R-wave polarity, slope peak shift, R-wave width, and QR index are compared to the normal template at blocks 610, 612 and 614. If all of these features represent a change from the normal template, the PVC strict rate onset rule fires true at block 620. If any one of the FF specific beat features is not significantly different than the normal template, the FF specific beat feature evidence of a PVC-initiated VT is not strong enough to override other VT or SVT evidence provided by the overall FFMS result and zone-specific rules.

If the FF specific beat features do not provide evidence of VT at blocks 610 through 614, however, the NFMS may additionally be checked at block 616 to detect evidence of an initiating PVC. When both the NFMS and the FFMS of a preceding beat fall within the VT confident zone, the PVC strict rate onset rule will be satisfied (block 620). If neither the FF specific beat features (blocks 610 through 614) nor the NFMS and FFMS (block 616) meet the rule criteria, the PVC strict rate onset rule is false at block 606.

If the PVC strict rate onset rule fires true at block 620, this result may override other rules applied to single FFMS zones in adjusting the VT evidence counter. In one embodiment, the VT evidence counter is increased to a maximum value (e.g. 8) at block 622 in response to the PVC strict rate onset rule being true. If the PVC strict rate onset rule is false, the FFMS and corresponding zone-specific rule(s) are used to determine the adjustment to the VT evidence counter for the current beat.

Figure 15:
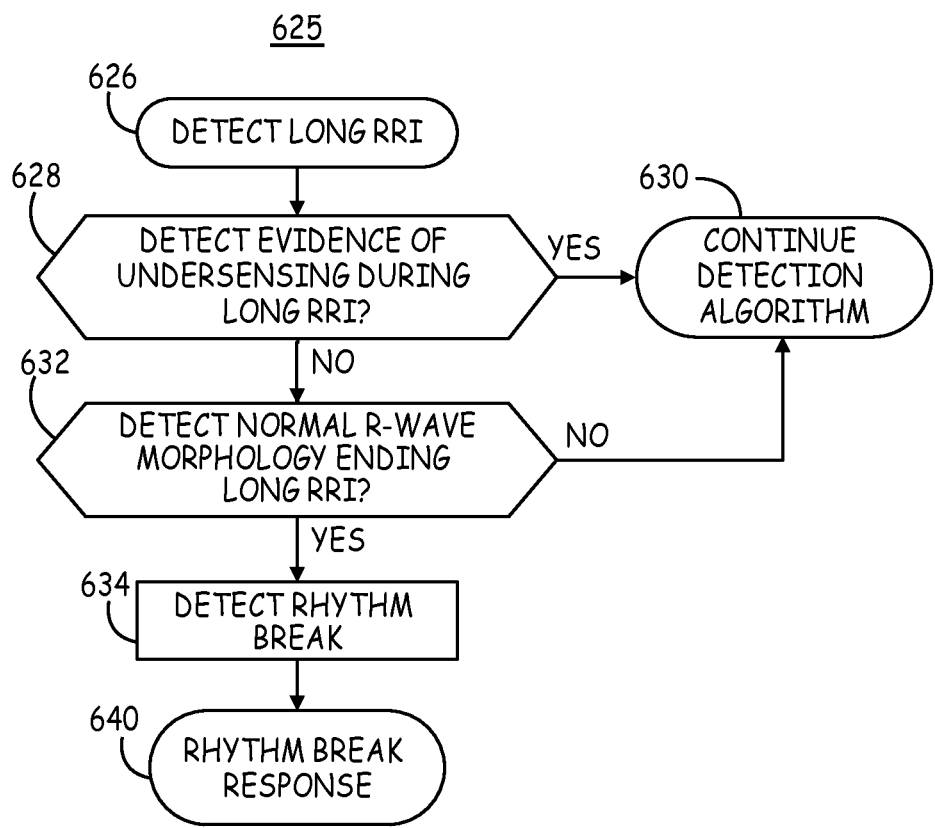
FIG. 15 is a flow chart of a process for applying a rule for detecting a rhythm breaking point.

FIG. 15 is a flow chart 625 of a process for applying a rule for detecting a rhythm breaking point, which may be applied across multiple FFMS zones. Interval-based tachycardia detection methods often require a specified number of RRIs out of a previous number of most recent RRIs, e.g. 18 out of 24 intervals, to be shorter than a tachycardia detection interval in order to detect tachycardia. This allows a small number of the most recent RRIs to be longer than the tachycardia detection interval and still appropriately detect tachycardia in the presence of undersensing. In some cases, however, a long RRI may be an actual pause in the rhythm rather than the result of undersensing. Detection of an actual long pause is useful information in detecting a break or spontaneous termination of a tachycardia rhythm.

A long pause or two consecutive normal beats marking a break in the tachycardia rhythm may occur during atrial fibrillation, recurrent non-sustained VT, or other non-treatable rhythms. Two consecutive normal beats or a long pause may also be detected when a concerning rhythm is the result of T-wave oversensing. As such, it is desirable to detect an actual long RRI and normal R-wave morphology such that a rhythm breaking point can be identified and used to avoid progression to detection of a treatable tachycardia and therapy delivery when the rhythm is non-sustained or a non-treatable rhythm.

Generally, at any time during a detection algorithm, a long RRI may be detected at block 626. Criteria for detecting a long RRI may be based on a percentage of the previous RRI and/or an average of a specified number of the most recent RRIs. For example, if the current RRI is at least 25% longer than the previous RRI and is longer than the average, maximum, or another metric of the most recent 8 RRIs (or another number of most recent RRIs), a long RRI is detected. An additional or alternative requirement may be that the RRI is longer than a minimum threshold interval. Various criteria may be applied for detecting a long RRI but will typically include a comparison to the previous RRI and/or a metric of the most recent RRIs.

At blocks 628 and 632, additional analysis of the EGM signal(s) is performed to detect evidence supporting the detection of an actual long RRI or evidence of undersensing that would indicate the long RRI is due to undersensing. At block 628, the EGM signal(s) are examined for evidence of an undersensed R-wave occurring during the long RRI. Evidence of an undersensed R-wave may include a maximum slew rate exceeding a threshold, a maximum amplitude exceeding a threshold, and/or other signal features occurring during the long RRI that may correspond to a QRS complex. For example, if the signal amplitude exceeds a predetermined percentage of the most recent sensed R-wave amplitude, an intervening R-wave may have been undersensed resulting in a false detection of a long RRI. In a specific example, if an amplitude greater than approximately 25% of the current R-wave amplitude is found during the detected long RRI, an undersensed R-wave may be present. Amplitude, slew rate or other signal morphology evidence of an undersensed event may be detected or obtained from the same EGM signal or a different EGM signal than the one used to detect the long RRI.

Additionally or alternatively, another EGM sensing vector may be checked at block 628 to verify that a sensed event did not occur on another sensing vector during the detected long RRI. For example, if the long RRI is detected on the NF EGM signal, the FF EGM signal is checked to verify that a sensed event did not occur on the FF EGM signal during the long RRI on the NF signal. A FF sensed event occurring within a short interval of time with respect to a NF sensed event may correspond to the same beat. Thus the interval examined on the FF EGM signal for detecting evidence of an undersensed R-wave on the NF EGM signal may be defined to be a truncated or narrower interval within the NF long RRI. For example, an interval beginning approximately 50 to 80 ms after the previous NF sensed event and ending approximately 50 to 80 ms earlier than the current NF sensed event may be examined for FF sensed events. If a FF sensed event does not occur during the interval, the long RRI is likely to be an actual long pause that may be detected as a rhythm breaking point.

In a similar manner, a long RRI measured on the FF EGM signal may be verified by checking whether a sensed event occurs within a corresponding truncated interval on the NF EGM signal. A variation of the method of searching for a sensed event during a truncated interval is to determine if sensed events occur on two different EGM signals in a 1:1 ratio of an interval encompassing one or more RRIs on the first EGM signal. For example, if three events occur on the FF signal during an interval eencompassing a single RRI on the NF signal, undersensing on the NF signal may be suspected.

If there is evidence of an undersensed R-wave during the long RRI, e.g., based on a high slew rate, high amplitude, sensed event on another sensing vector or other signal features during the long RRI, a rhythm breaking point is not detected and the tachycardia detection algorithm continues at block 630. Any pending therapies may proceed. If there is no evidence of an undersensed R-wave, the sensed event morphology maybe analyzed at block 632 to verify that the R-wave ending the long RRI represents a normal R-wave morphology. A morphology matching score may be computed, and a high matching score of the R-wave ending the long RRI is detected as a rhythm breaking point at block 634.

The morphology matching score required to detect the rhythm breaking point may be dependent on the length of the long RRI. A threshold morphology matching score required for detecting a rhythm breaking point for different ranges of RRIs may be stored in a look-up table or may be defined as an exponential or other relationship between the matching score and the RRI. To illustrate, if the RRI is only slightly longer than the previous RRI or an average of recent RRIs, for example up to approximately 25% longer, a very high morphology matching score may be required to detect a rhythm breaking point, e.g. within an SVT confident zone. If the long RRI is much longer than the previous RRI or an average of recent RRIs, for example more than approximately 50% longer, a lower matching score, e.g. a score in the SVT gray zone, may be accepted as evidence of a rhythm breaking point.

In one specific embodiment, if the current RRI is at least approximately 25% greater than the previous RRI and the average of the most recent 8 RRIs and is at least 350 ms long, a rhythm breaking point is detected when the morphology matching score of the QRS signal that ends the long RRI is greater than 35/RRI, wherein RRI is the current RRI in seconds and the morphology matching score ranges from 0 to 100.

It is contemplated that one or both of blocks 628 and 632 may be performed when a long RRI is detected for verifying a rhythm breaking point. At block 640, a response to the rhythm breaking point is provided. The response to detecting a rhythm breaking point may include aborting a therapy, delaying a therapy, resetting an initiated menu of therapies to an earlier therapy in the menu sequence, clearing counts or other evidence of VT, augmenting evidence of SVT, changing a classification of the current rhythm, or ending a measurement of the rhythm episode duration and resetting an episode timer.

The detection of a long pause may occur during any state of the detection algorithm, including the convinced State 3, and the response to detecting the long pause as a rhythm breaking point may vary between states as appropriate.

With regard to the tachycardia detection algorithm State 2 operations, the VT evidence counter may be set to zero in response to a pause detection. If any therapies have been delivered during the current tachycardia episode, the next scheduled therapy will be reset to the first therapy of a programmed menu of therapies. As a result, the next therapy delivered upon reaching State 4 again will be the first therapy of a selected menu of therapies rather than a progression to a more aggressive therapy.

The method for detecting a rhythm break may be implemented in any tachycardia detection algorithm and is not limited to use in the rule-based detection algorithm described herein. The process of monitoring for a long RRI and analyzing the long RRI for evidence of undersensing and/or for evidence of a normal beat concluding the long RRI may be performed for detecting a rhythm breaking point in any tachycardia detection algorithm.

Figure 16:
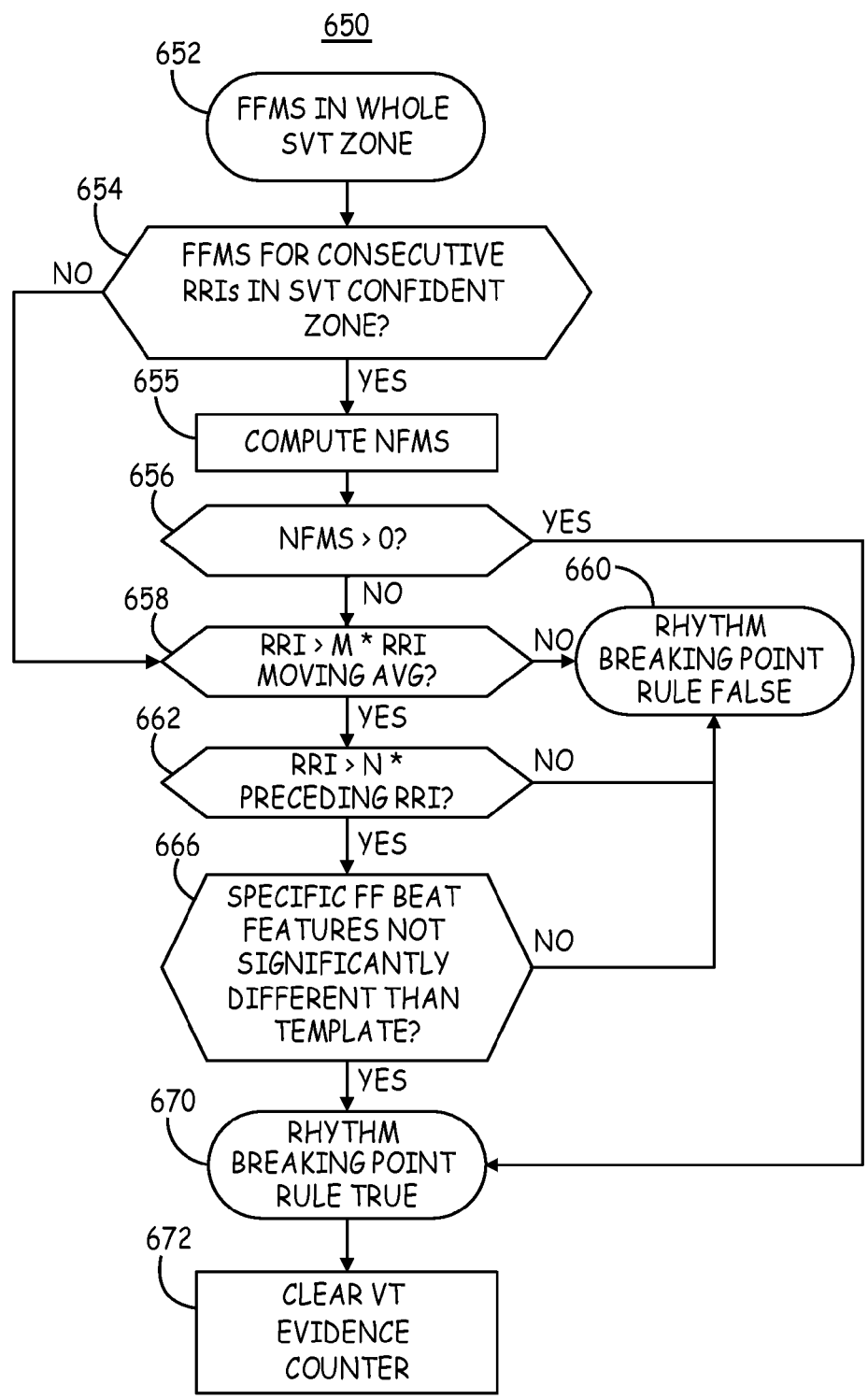
FIG. 16 is a flow chart of one method for applying a rule for detecting a rhythm breaking point across the whole SVT morphology score zone.

FIG. 16 is a flow chart 650 of one method for applying a rule for detecting a rhythm breaking point across the whole SVT zone. In this example, a Rhythm breaking point rule is applied when the FFMS falls into either the SVT confident zone or the SVT gray zone. The Rhythm breaking point rule is applied to detect any beat that is normal with a high degree of confidence. A normally conducted beat associated with a long pause or two consecutive normal beats may be an indicator of a break in a tachycardia rhythm.

If the FFMS for the current beat falls into the whole SVT zone (block 652), the previous FFMS zone is checked at block 654. If the FFMS for both the current and previous consecutive sensed events are within the SVT confident zone, the NFMS is computed at block 655. As long as the NFMS for the current beat is greater than zero (or another predetermined threshold) at block 656, the two consecutive FFMS in the SVT confident zone provide evidence of a rhythm break. The Rhythm breaking point rule fires true at block 670.

If the current and previous FFMS do not both fall into the SVT confident zone (i.e., one or both falls into SVT gray zone or lower), the current RRI is analyzed to detect a long pause in the tachycardia rhythm. In general, if the current RRI is determined to be longer than previous RRIs, the current RRI may represent a long pause and a rhythm breaking point. In one embodiment, the current RRI is compared to a moving average of recent RRIs, for example the most recent eight RRIs, at block 658. The current RRI may be required to be longer than RRI moving average or any factor of the RRI moving average. For example the weighting factor "M" in block 658 may be equal to 1 or a higher value.

If the current RRI is longer than the moving average, or a required percentage longer than the moving average, the current RRI may also be compared to the most recent preceding RRI at block 662 to verify a long pause. The current RRI is required to be longer than the preceding RRI by a predetermined factor or percentage. The weighting factor "N" in block 662 may be equal to approximately 1.3, for example, or another selected value greater than 1. If the current RRI is not likely to be a long pause based on a negative result of either of the comparisons at blocks 658 and 662, the Rhythm breaking point rule is not satisfied and declared false at block 660.

If the current RRI is longer than the preceding RRI, for example at least approximately 30% longer than the preceding RRI, FF specific beat features are examined at block 666 to determine if the beat concluding the long RRI is a normal beat. Various FF specific beat features may be examined to determine if the specific beat features closely match corresponding specific beat features of a normal beat template at block 666. In one embodiment the FF R-wave symmetry index, FF R-wave width, and FF QR Index are each compared to the respective features of a FF normal beat template. If each of these features falls within an acceptable threshold range of the normal beat template, the Rhythm breaking point rule is satisfied and declared true at block 670. The combined evidence of a long RRI, FFMS in the whole SVT zone, and specific FF beat feature evidence of a normally conducted R-wave suggests that the current beat is a rhythm breaking point. It is to be understood that in various embodiments, the FFMS, FF specific beat features, the NFMS and/or NF specific beat features may be used alone or in any combination for determining that the ending R-wave of the long RRI is highly likely to be a normal beat.

If the Rhythm breaking point rule is true, this result may override other single zone rules and the FFMS in adjusting the VT evidence counter. In one embodiment, the VT evidence counter is cleared to a zero value at block 672 in response to the Rhythm breaking point rule being true.

If more than one multiple zone rules are included in the tachycardia detection algorithm, the multiple zone rules may be performed in a hierarchical order such that a highest level rule that fires true overrides the results of lower level rules in causing adjustment to the VT evidence counter. Multiple zone rules may be written such that they are mutually exclusive, i.e. there is no possibility of more than one multiple zone rule firing simultaneously. For example, a whole gray zone rule and a whole SVT zone rule may be written such that both rules cannot be satisfied for a current RRI. In other embodiments, an adjustment to the VT evidence counter in response to a multiple zone rule firing true may be made only when a single multiple zone rule fires true and all others are false. In this case, if more than one multiple zone rule fires true, the multiple zone rules may be considered inconclusive, and the results of the single zone rules and FFMS are relied upon for adjusting the VT evidence counter.

Alternatively, if multiple rules apply to a particular FFMS zone, which may include single zone and/or multiple zone rules, the rules may be applied in a predefined sequence such that a lower level rule is only applied if all higher level rules are false. The VT evidence counter is adjusted as soon as a rule fires for a given FFMS zone.

Figure 17:
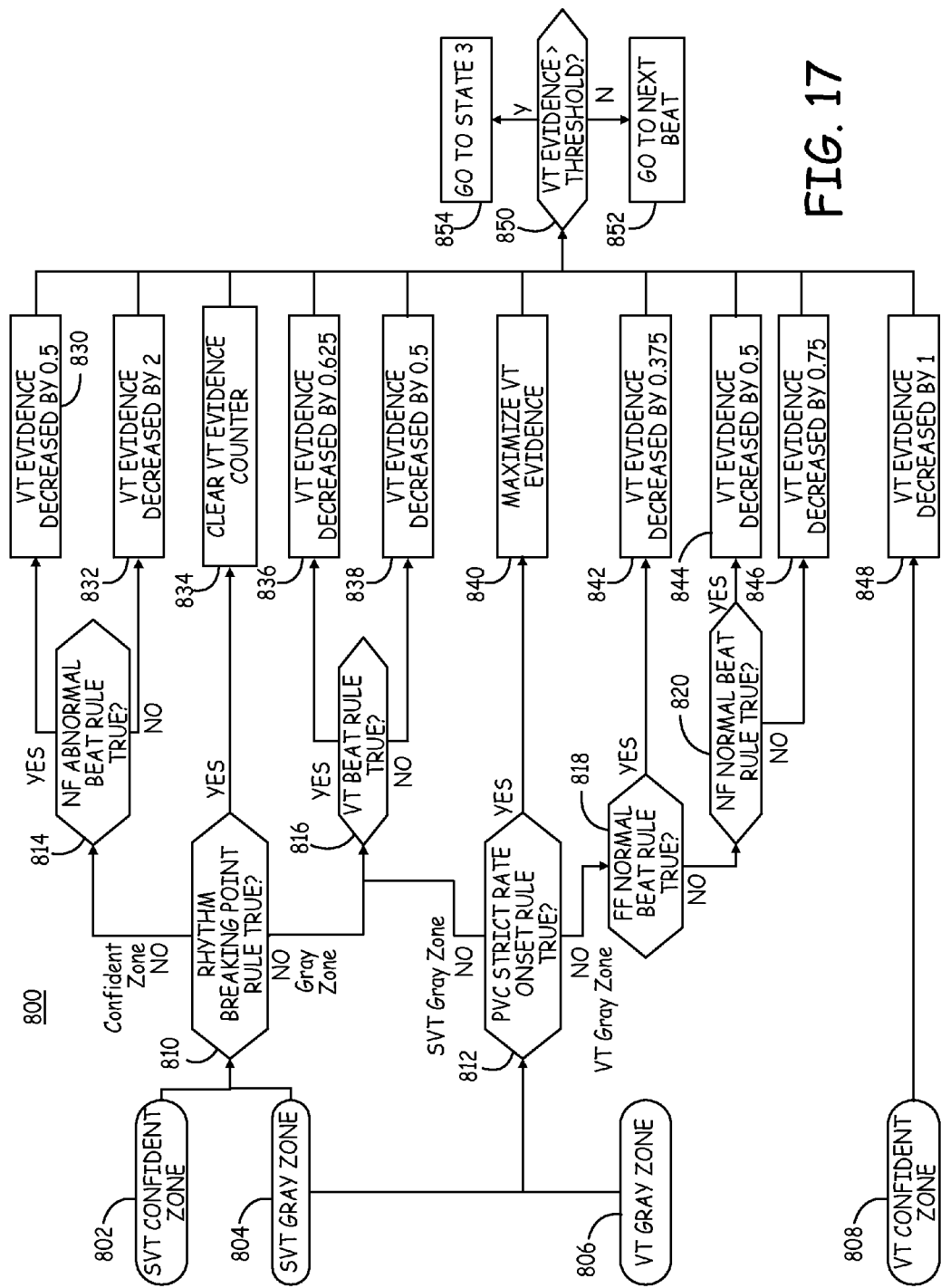
FIG. 17 is a flow chart of a process for adjusting a VT evidence counter on a beat-by-beat basis in response to morphology score zone rules.

FIG. 17 is a flow chart 800 of a process for adjusting a VT evidence counter on a beat-by-beat basis in response to FFMS zone rules for accumulating evidence for detecting a treatable tachycardia. The process shown in flow chart 800 determines the appropriate increment or decrement applied to a VT evidence counter for a given beat in response to applied beat feature rule(s). Other criteria that may be applied for deciding if the VT evidence counter should be adjusted and by how much, such as verifying that the FF EGM signal is not corrupted, are not shown in FIG. 17. It is recognized, however, that other criteria may be applied before making any adjustment to the VT evidence counter. If, for example, the FF EGM signal is corrupted, the beat may be skipped entirely with no adjustment to the VT evidence counter.

In the process shown, the rhythm breaking point rule is applied when the FFMS falls into the whole SVT zone, i.e. the SVT confident zone 802 or the SVT gray zone 804. Application of one embodiment of a rhythm breaking point rule is described above in conjunction with FIG. 16. The rhythm breaking point rule is a higher level rule than zone-specific rules. As such, if the rhythm breaking point rule is found true at decision block 810, The VT evidence counter is adjusted at block 834 without applying additional zone-specific rules. In the illustrative example, the VT evidence counter is cleared to a zero value in response to the evidence of a rhythm breaking point, i.e. a non-sustained tachycardia.

When the rhythm breaking point rule is false and the FFMS falls into the SVT confident zone (upper branch of block 810), the process proceeds to block 814 to apply beat feature rules specific to the SVT confident zone. In the illustrated embodiment, the NF abnormal beat rule is applied at block 814, as described above in conjunction with FIG. 13A. When the NF Abnormal beat rule is false, the VT evidence counter is decreased at block 832. The strong evidence of an SVT beat based on the FFMS and the lack of evidence of a VT beat based on the NF abnormal beat rule result justifies a relatively large decrement of the VT evidence accumulation. In this example, the VT evidence counter is decreased by 2 at block 832.

If the NF abnormal beat rule is true at block 814, evidence that contradicts the result of the overall FFMS has been found in specific beat features. The VT evidence may still be decreased in response to the FFMS falling into the SVT confident zone, but by a smaller decrement than when the NF abnormal beat rule is false. At block 830, VT evidence counter is decreased, for example, by 0.5.

When the rhythm breaking point rule is false (block 810) and the FFMS falls into the SVT gray zone (lower branch of block 810), the process moves to block 816 to apply zone specific rules for the SVT gray zone. In one embodiment, the VT beat rule is applied at block 816 as described above in conjunction with FIG. 13B. When the VT beat rule is false, the VT evidence counter is decreased by 0.5 at block 838 in response to the FFMS falling into the SVT gray zone and the lack of specific beat feature evidence for a VT beat. The VT evidence accumulation is decreased at block 838 by a smaller decrement than when the FFMS falls into the VT confident zone with no evidence of an abnormal beat.

When the VT beat rule is true at block 816, the combination of the FFMS being in the SVT gray zone and the contradictory evidence of a VT beat based on the specific beat features results in an increase in VT evidence at block 836. In the illustrated example, the increment applied at block 836 is 0.625.

In addition to applying the rhythm breaking point rule when the FFMS falls into the SVT gray zone, the PVC strict rate onset rule is applied at block 812 whenever the FFMS falls into the SVT gray zone (block 804). The PVC strict rate onset rule is also a multiple zone rule and is applied across the entire gray zone, including both the SVT gray zone (block 804) and the VT gray zone (block 806). If the PVC strict rate onset rule is true at block 812, VT evidence is immediately adjusted at block 840 without applying any single zone rules. The VT evidence counter is maximized in one embodiment in response to the PVC strict rate onset rule being true.

As mentioned previously, the multiple-zone rules applied at blocks 810 and 812 may either be written in an exclusive manner such that only a single rule can be true for a given beat, or the multiple-zone rules may be applied in a hierarchical manner such that only the VT evidence counter is immediately adjusted in response to the first rule firing. Alternatively, an additional step may be included in the flowchart 800 for verifying that other multi-zone rules are false before adjusting the VT evidence in response to a multi-zone rule being true. These various options are not shown in FIG. 17 for the sake of clarity. In general, the VT evidence metric is adjusted in response to a single rule firing and is not adjusted more than once for a current heart beat.

If the PVC strict rate onset rule is false when the FFMS falls into the SVT gray zone at block 812 (upper branch), the zone-specific rule for the SVT gray zone is applied at block 816 as described above. If the FFMS falls into the VT gray zone and PVC strict rate onset rule is false at block 812 (lower branch), the single zone rule for the VT gray zone is applied at block 818. In this example, the FF normal beat rule is applied as described above in conjunction with FIG. 13C. If the FF normal beat rule is true, this evidence of an SVT beat overrides the influence of the FFMS falling into the VT gray zone in adjusting the VT evidence counter. The VT evidence is decreased by a relatively small decrement at block 842 in response to the FF normal beat rule being true in contradiction to the FFMS falling into the VT gray zone.

In this example, more than one zone-specific rule may be applied for a given FFMS zone. For the VT gray zone, if the FF normal beat rule is not true at block 818, the NF normal beat rule as described in conjunction with FIG. 13C above is also applied at block 820. When evidence of a normal beat is found in the NF signal, this result overrides the influence of the FFMS falling into the VT gray zone on VT evidence accumulation. VT evidence is decreased at block 844 in response to the NF normal beat rule being true rather than being increased in response to the FFMS being in the VT gray zone. It is recognized that the FF normal beat rule (block 818) and the NF normal beat rule (block 820) may be applied in a different hierarchical order such that the VT evidence is adjusted based on the first rule to fire true.

In this example, the NF normal beat evidence is considered stronger evidence of an SVT beat than the FF normal beat evidence. As such, the VT evidence is decreased by a larger decrement in response to the NF normal beat rule being true than the FF normal beat rule being true.

If the whole gray zone PVC strict rate onset rule (block 812) is false and the single zone rules (blocks 818 and 820) applied to the VT gray zone are all false, the VT evidence counter is increased at block 846. Because the FFMS is in a VT gray zone rather than the VT confident zone, the increment applied to the VT evidence counter is relatively small, e.g. 0.75.

When the FFMS falls into the VT confident zone (block 808), the VT evidence counter is immediately increased by 1 at block 848. In other embodiments, zone-specific rules may be applied for the VT confident zone. However, in the illustrated embodiment, the FFMS being very low is considered strong evidence of a VT beat warranting a relatively large increase in the VT evidence accumulation.

It is contemplated that differently sized increments/decrements may be selected for use at the various blocks 830 through 848 based on the degree of confidence provided by the application of a given rule. The degree of confidence in separating VT and SVT beats for a given rule may be determined through clinical evaluation.

After adjusting the VT evidence counter at one of blocks 830 through 848, the VT evidence counter is compared to a detection threshold at block 850. If the VT evidence counter meets or exceeds the detection threshold, e.g. a threshold of 6 in one embodiment, a transition to the convinced State 3 occurs at block 854. If the VT evidence metric has not reached the detection threshold at block 850, the detection algorithm remains in State 2 and advances to the next beat at block 852 to continue accumulating VT evidence. The detection threshold applied to the VT evidence counter may vary between embodiments and may be tailored for a specific patient. The threshold will also depend in part on the size of the various increments/decrements applied in response to the various beat feature rules and FFMS zones.

Figure 18:
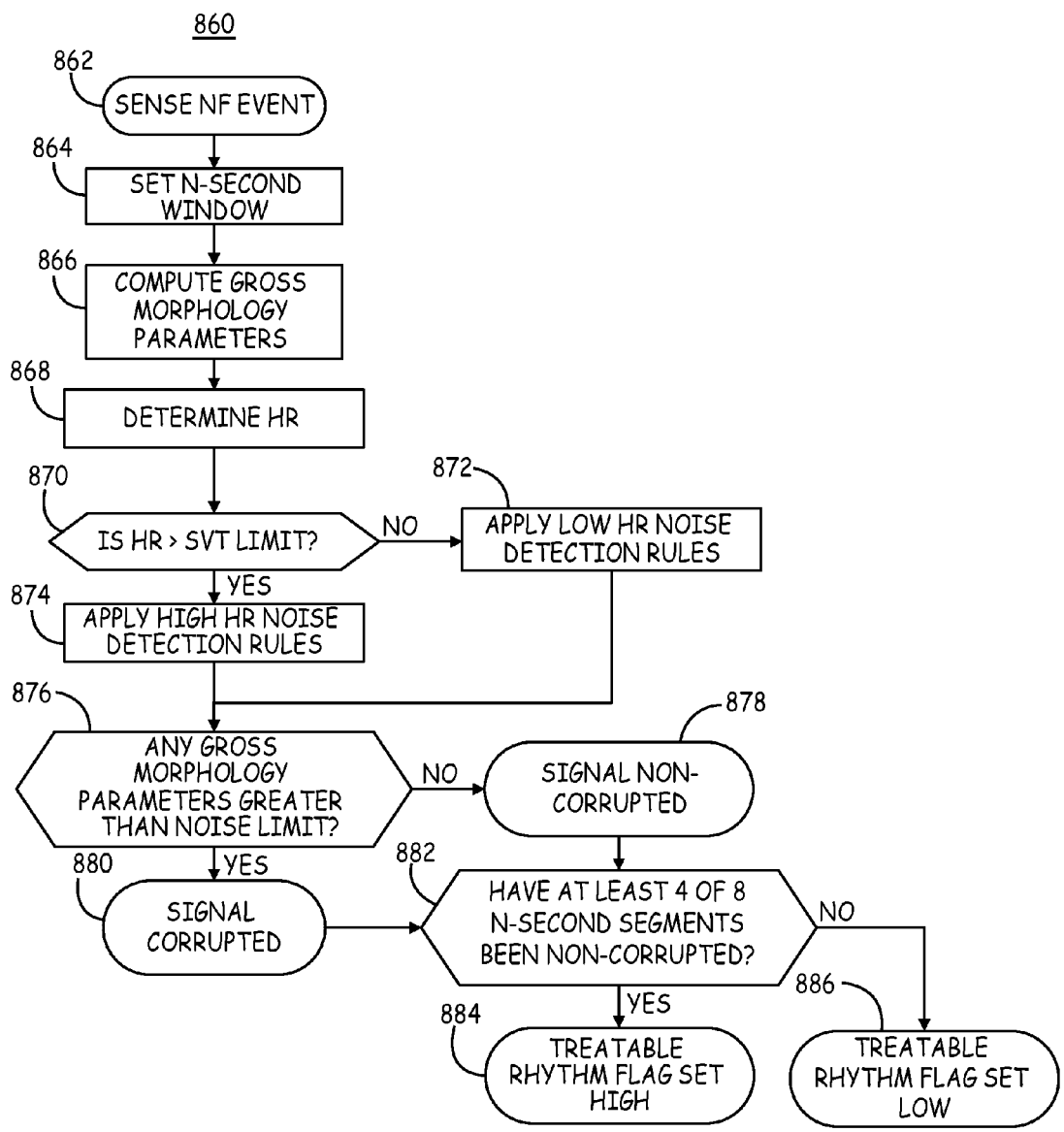
FIG. 18 is a flow chart of a method for classifying a current beat as a corrupted or non-corrupted signal in a noise/artifact rejection process.

FIG. 18 is a flow chart 860 of a method for classifying a current beat as a corrupted or non-corrupted signal in a noise/artifact rejection process. The process shown in FIG. 18 is performed to exclude non-physiological signals from interfering with correct rhythm classification. The method shown in flow chart 860 may correspond to the noise/artifact rejection process represented by blocks 512, 524, and 554 in FIGS. 13A-C, respectively. As described above, a current beat may be skipped and not used in updating the VT evidence counter when the FF EGM signal is identified as a corrupted beat (see for example, block 510 of FIG. 13A, block 526 of FIG. 13B and block 556 of FIG. 13C). A beat feature rule that utilizes a NFMS or features extracted from the NF EGM signal may be false if the NF EGM signal is corrupted (see for example block 514 of FIG. 13A, block 532 of FIG. 13B and block 572 of FIG. 13C).

In order to classify a current beat as a corrupted signal for rejecting the current beat in accumulating VT evidence or deciding a specific beat feature rule is false, one or more cardiac cycles or an n-second segment of the EGM signal may be examined to detect the presence of non-physiological signals. In other words, classification of the current beat as being noise corrupted is not limited to examining a current RRI of the EGM signal of interest but may include examining a longer EGM signal interval to detect presence of noise that may interfere with correct rhythm classification.

The process shown in flow chart 860 may be applied to the FF EGM signal or the NF EGM signal or both signals. At block 862 a cardiac event is sensed for use in setting a noise corruption analysis window at block 864. In one embodiment, a NF event is sensed for setting a one-second window applied to both the FF and NF EGM signals for detecting noise corruption. The n-second window is set to extend n-seconds earlier than the currently sensed event and end upon the NF event. The predefined noise corruption analysis window duration is typically set to be longer than RRIs, for example at least one second in duration, such that there will be overlap between the n-second noise analysis windows from one beat to the next.

At block 866, gross morphology parameters are computed for the FF and/or NF EGM signal during the n-second window. The parameters computed for detecting noise corruption can be referred to as "gross morphology" parameters in that these parameters can be computed over the entirety of an n-second signal segment without limiting the analysis primarily to the morphology of an R-wave signal. EGM signal baseline, T-wave or other signal segments may be included in the n-second window used for measuring gross morphology parameters. The "gross" morphology of the EGM signal is used to detect noise/artifact corruption since noise artifact may appear at any time in the EGM signal and is not limited to a window of time corresponding to a QRS waveform. Even though there may be considerable overlap between consecutive n-second segments, only the current RRI that ends with the sensed event that triggered the current n-second noise analysis window is classified as being corrupted or non-corrupted based on the noise information contained in the current n-second segment. The classification of other previous RRIs falling within the n-second segment is not affected by the current n-second segment.

Gross morphology parameters used to detect the presence of non-physiological noise may include a noise-to-signal ratio (NSR) (or conversely a signal-to-noise ratio), a mean period (MP), and metrics related to muscle noise content and signal characteristics associated with lead-related conditions. These parameters are used to reject signals contaminated by high frequency noise, significant muscle noise, and characteristic lead-related artifact. The noise/artifact rejection process may include methods generally disclosed in commonly-assigned U.S. Publication No. 2007/0239048, hereby incorporated herein by reference in its entirety.

At block 868, the current HR is determined using at least the current RRI, all of the RRIs occurring during the n-second strip or a current HR estimate as described above based on the nth shorted RRI out of the most recent m RRIs. If the HR is greater than an SVT limit (block 870), noise detection rules for use during a high heart rate are applied at block 874. If the HR is less than an SVT limit, a different set of noise detection rules may be applied for heart rates slower than the SVT limit at block 872.

The gross morphology parameters used for detecting a corrupted signal and/or the thresholds applied to those gross morphology parameters may be dependent on an estimate of the current heart rate. Different noise detection criteria may be applied for detecting noise corruption during heart rates above the SVT limit than during heart rates below the SVT limit. Generally, during HRs greater than the SVT limit, more stringent noise corruption criteria are applied. For example, higher thresholds may be applied to the gross morphology parameters for detecting noise corruption.

If any of the gross morphology parameters exceed a noise corruption threshold, as determined at block 876, the signal is classified as a corrupted signal at block 880. If none of the parameters exceed the noise corruption thresholds applied based on heart rate, the signal is non-corrupted as indicated at block 878. Noise detection parameters including a mean period, metrics of muscle noise, and/or a NSR as generally disclosed in the above referenced '048 published application may be compared to noise detection thresholds at block 876. Different criteria may be applied to FF and NF signals for classifying the signal as corrupted or non-corrupted.

As described in conjunction with FIG. 13A through 13C, if the FF signal is found to be corrupted for the current RRI interval (using the n-second segment), the VT evidence counter will not be adjusted for the current beat. If the FF signal is found to be non-corrupted the VT evidence counter may be adjusted according to the FFMS zone and the results of any beat feature rules applied for the zone. If the beat feature rule involves analysis of the NF EGM signal, the rule may be found false if the NF EGM signal is classified as corrupted at block 880 for the current heart beat.

At block 882, a count of the number of n-second segments that have been classified as non-corrupted out of a specified number of the most recent segment is maintained. In one embodiment, if at least half of the n-second segments are classified as non-corrupted, e.g. at least four out of the most recent eight n-second segments, a treatable rhythm flag is set high at block 884. This treatable rhythm flag may be required to be high in order to allow a transition from State 2 to the convinced State 3. The treatable rhythm flag is an indication that the EGM signal being analyzed is considered to be a clean enough signal for the purposes of reliably classifying the rhythm as a treatable rhythm when other state transition criteria are also satisfied. For example, in one embodiment, if both the NF and the FF HR estimates exceed the SVT limit and a NF treatable rhythm flag and a FF treatable rhythm flag are set high, a transition to the convinced State 3 may occur. This transition based on both the NF and FF HRs exceeding the SVT limit may occur even if the VT evidence counter has not crossed a detection threshold.

If more than half (or another percentage) of the most recent n-second segments are classified as corrupted, the treatable rhythm flag for the corresponding EGM signal is set low at block 886. In this case, even if other criteria are met for transitioning from the concerned State 2 to the convinced State 3, a state transition may not occur due to the corruption of the EGM signal. For example, if the NF and FF HR estimates exceed an SVT limit for advancing to the convinced State 3, but one of the NF or the FF EGM signal treatable rhythm flag is set low, the state transition will not occur. The treatable rhythm flag must be set high for at least one or both the FF and NF EGM signals based on the respective signal being classified as non-corrupted before the detection algorithm will advance to the convinced State 3.

In some embodiments, reliance on a "primary" EGM signal may be switched between the NF and FF EGM signals based upon the status of the treatable rhythm flag. For example, if the NF EGM signal is found noise-corrupted and the NF treatable rhythm flag is set low, the FF EGM signal may become the primary signal for sensing cardiac events, setting a morphology analysis, and computing an overall morphology matching score. When the NF EGM signal is found to be non-corrupted again, i.e. the NF treatable rhythm flag is set high, its role as primary sensing signal for sensing cardiac events and setting a morphology analysis window is restored again.

If the FF EGM signal is found noise-corrupted, and the FF treatable rhythm flag is set low, the NF signal may be used for computing an overall morphology matching score until the FF treatable rhythm flag is again set high. Likewise, specific beat feature rules may be applied using beat features derived from only an EGM signal having a treatable rhythm flag set high. For example, FF signal features may be substituted in a specific beat feature rule that normally relies on NF signal features and vice versa.

In one embodiment, if the FF EGM signal is corrupted, instead of skipping the beat for the purposes of VT evidence accumulation as described above in conjunction with FIGS. 13A-13C, the NFMS may be computed. If the NFMS is in a confident zone, the VT evidence counter is adjusted in response to the NFMS zone. If the NFMS is in a gray zone, the VT evidence counter is not adjusted and the beat is skipped. The VT evidence counter may be adjusted by a relatively smaller increment or decrement in response to a NFMS confident zone (when FF EGM is corrupted) than the increment or decrement applied in response to a FFMS confident zone (when FF EGM is non-corrupted). In an illustrative example, the VT evidence counter may be increased by 0.75 instead of by 1 when the NFMS is in the VT confident zone and the FF EGM signal is found to be corrupted. The VT evidence counter may be decreased by 1.5 instead of by 2 when the NFMS is in the SVT confident zone and the FF EGM signal is corrupted.

Figure 19:
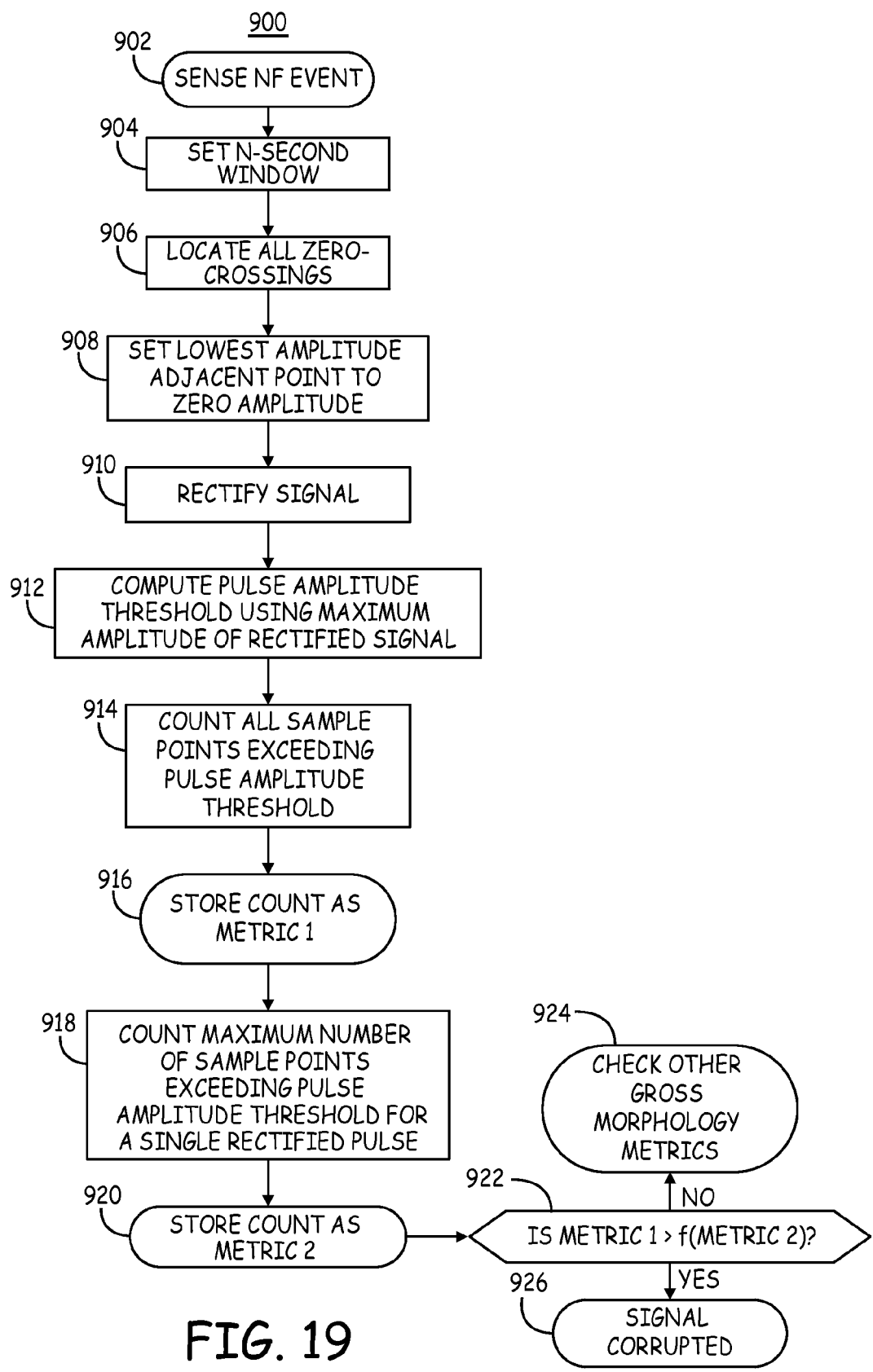
FIG. 19 is a flowchart of one method for computing metrics of lead artifact for use in classifying an EGM signal as corrupted or non-corrupted.

FIG. 19 is a flowchart 900 of one method for computing metrics of lead artifact for use in classifying an EGM signal as corrupted or non-corrupted. The process shown in flowchart 900 may be performed on either of the FF or the NF EGM signals or both for use in classifying the respective signal as corrupted or non-corrupted as part of the noise/artifact rejection process shown in FIG. 18. At block 902, a cardiac event (R-wave) is sensed on the NF EGM signal for setting the n-second noise analysis window at block 904.

At block 906, all of the zero crossings during the n-second segment are located. Sample points immediately adjacent to each zero crossing are identified. The amplitude of the adjacent sample point before a zero crossing and the amplitude of the adjacent sample point after the same zero crossing are compared. The sample point adjacent to each zero crossing having the smallest absolute amplitude is set to a zero amplitude at block 908 in order to anchor the point to a zero value for demarcating the positive- and negative-going pulses in the n-second noise analysis window.

The n-second signal segment is then rectified at block 910. The maximum amplitude of the rectified signal is determined, and a predetermined percentage or portion of the maximum rectified signal amplitude, for example half the maximum rectified signal amplitude, is computed at block 912 as a pulse amplitude threshold. All rectified signal sample points having an amplitude greater than half (or another percentage) of the maximum rectified signal amplitude are counted at block 914. This count is stored as a noise artifact metric 1 at block 916. In one embodiment, the noise artifact metric is used as a measure of lead-related artifact. The percentage or portion of the maximum rectified signal amplitude used as a pulse amplitude threshold may be defined based on the HR, which may be estimated using any methods described herein. When the HR is greater than the SVT limit, more stringent noise detection criteria may be applied by selecting a larger portion of the maximum rectified signal amplitude as a pulse amplitude threshold for computing the noise artifact metric 1.

At block 918, a single pulse within the rectified signal having the maximum number of sample points exceeding half (or another percentage) of the maximum rectified signal amplitude is identified. To identify this single pulse, the sample points in each individual pulse during the n-second segment that exceed half of the maximum rectified signal amplitude are counted. The count for each individual pulse is then compared to the count for every other pulse. The pulse having the maximum number of sample points exceeding half of the maximum rectified signal amplitude is identified as the pulse having a maximum pulse width. The number of points exceeding half of the maximum rectified signal in the maximum pulse width pulse is stored at block 920 as a second lead artifact metric.

At block 922, the lead artifact metric is compared to a corrupted signal threshold defined as a function of the second lead artifact metric, "metric 2". For example, the lead artifact metric 1 may be compared to a threshold defined as W*(metric 2−x). The terms "W" and "x" used here are not necessarily equal to or related to other equation terms identified herein by the same letter. The weighting factor "W" and/or term "x" may be set based on heart rate, e.g. based on whether the current HR estimate exceeds the SVT limit as described in conjunction with FIG. 18. The noise threshold may be set to a higher value by increasing "W" and or "x" when the HR is greater than the SVT limit to create more stringent noise detection criteria.

In one embodiment, if the total number of sample points in the rectified signal exceeding half of the maximum amplitude is more than ten times greater than the number of sample points in a single pulse that exceed half of the maximum amplitude, the signal is classified as corrupted for the current beat at block 926. If the lead artifact metric does not exceed a corrupted signal threshold at block 922, other gross morphology metrics may be analyzed at block 924 before classifying the EGM signal as corrupted or non-corrupted for the current beat. Other gross morphology metrics may include a NSR, a mean period, and a metric related to muscle noise as mentioned previously.

Figure 20:
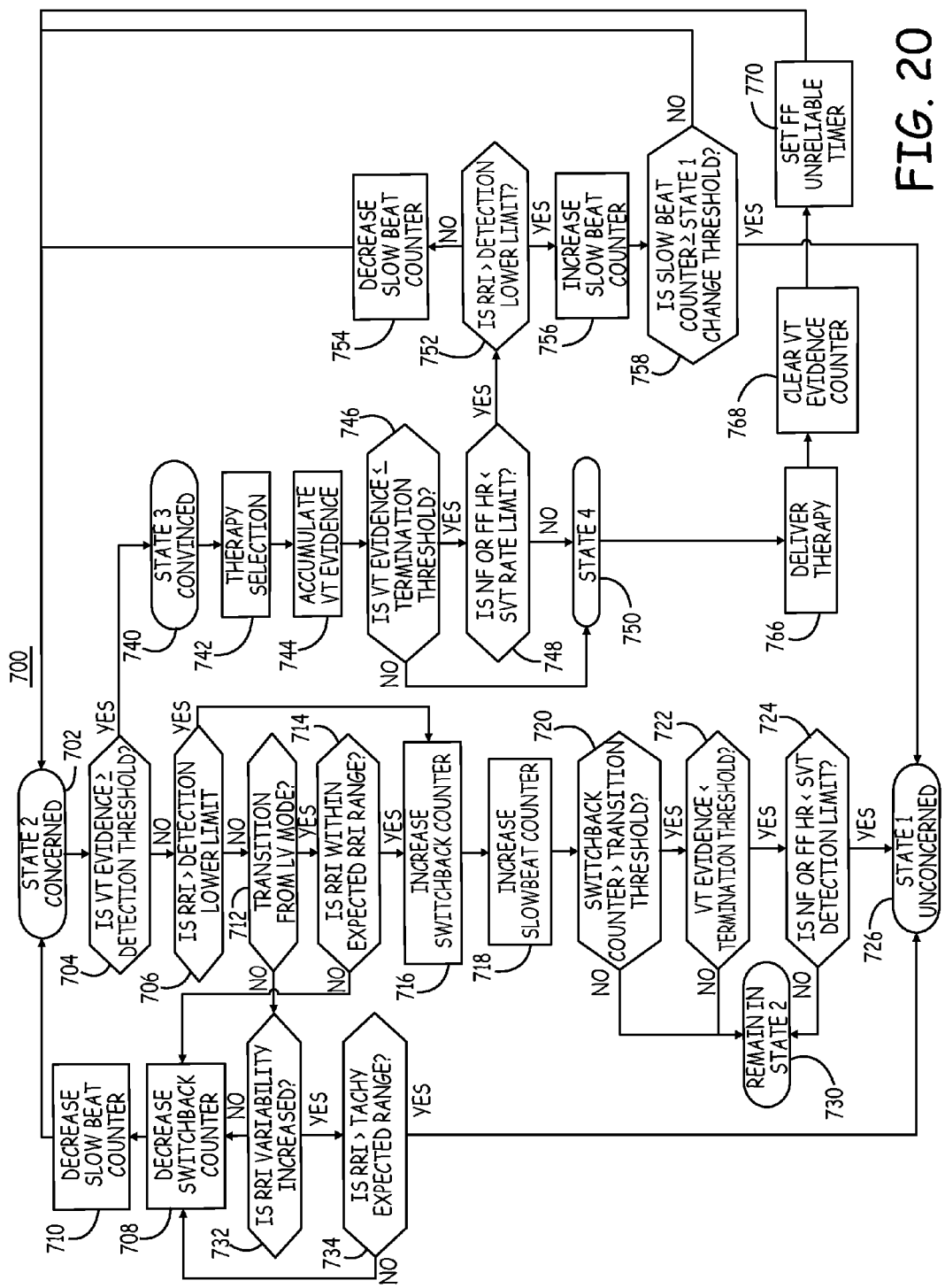
FIG. 20 is a flowchart of a method for transitioning between detection algorithm states.

FIG. 20 is a flowchart 700 of a method for transitioning between detection states. The method for transitioning from State 1, the unconcerned state, to concerned State 2 has been discussed previously. Once State 2 is entered at block 702, VT evidence is accumulated on a beat-by-beat basis. If the VT evidence counter does not reach the detection threshold, as determined at block 704, conditions for transitioning back into State 1 are examined beginning at block 706. In general, if the HR decreases and the VT evidence has fallen below a termination threshold, the detection algorithm may transition back into the unconcerned State 1. The transition criteria may be dependent on whether the transition into State 2 from State 1 occurred during the LV mode of operation or the HV mode of operation in State 1. The flow chart 700 provides one illustrative method that may be used to control the transition from State 2 back to State 1.

At block 706, the current RRI is compared to a detection lower limit interval. If the RRI is longer than a detection lower limit interval, a switchback counter is increased at block 716. The switchback counter is used to track consistently long RRIs (i.e. greater than the detection lower limit interval) for controlling transition back to State 1.

If the RRI is not greater than the detection lower limit interval, and State 2 was entered from State 1 during the LV mode of operation (as determined at block 712), the current RRI is compared to the stored expected RRI range at block 714. As described previously, the expected RRI range at the time of transitioning from State 1 to State 2 is frozen at its current value and stored for use in controlling transition back to State 1. If the current RRI is not within the expected RRI range at block 714, the switchback counter is decreased at block 708.

Additionally, a slow beat counter is decreased at block 710. The slow beat counter is a separate counter from the switchback counter and is also used to count "slow" heart beats. The slow beat counter is used to track consistently slow beats during States 2 and 3 and used to control transition from State 3 directly back to State 1 as will be described further below. The switchback counter and slow beat counter may be decreased by one, two or another selected decrement in response to an RRI that is shorter than the detection lower limit and not within the expected RRI range for a normal heart rhythm.

An RRI that is shorter than the detection lower limit and still outside a normal expected RRI range is evidence that the current rhythm is still a concerning rhythm and no state change is warranted. After decreasing the slow beat counter, the detection algorithm remains in State 2 by returning to block 702. The rhythm is still considered a concerning rhythm.

Returning to block 714, if the current RRI is within the stored expected RRI range for a normal heart rhythm, the switchback counter is increased at block 716. At block 718, the slow beat counter is also increased in response to an RRI longer than the detection lower limit (block 706) or an RRI within the expected RRI range when the transition to State 2 occurred during the LV mode of State 1 operation.

The switchback counter is compared to a transition threshold at block 720. If the switchback counter reaches the transition threshold, the VT evidence is compared to a termination threshold (block 722). The termination threshold is defined as a value less than the detection threshold and is used to determine when the accumulated VT evidence no longer meets a level indicating a concerning heart rhythm. If the VT evidence counter is below the termination threshold, a VT episode may have never occurred or a non-sustained VT episode may have occurred and spontaneously terminated.

If either of the NF or the FF HRs are currently less than an SVT detection limit (block 724), the combined evidence of the switchback count of consistently slow beats, low accumulation of VT evidence, and a HR estimate below an SVT detection limit results in a transition back to the unconcerned State 1 at block 726. If any one of these transition criteria is not met, the detection algorithm remains in State 2 (block 730).

Returning to block 712, if State 2 was not entered from the LV mode of operation in State 1 (i.e., State 2 was entered from the HV mode), the RRI variability is analyzed at block 732. In order to enter State 2 from the HV mode of operation, a sudden decrease in variability accompanied by an increase in HR was detected. If the RRI variability has again increased, the current heart rhythm may no longer be a concerning rhythm. An expected RRI range may not be stored when State 2 was entered from the HV mode of State 1. The expected RRI range may not be updated during the HV mode due to the high variability of RRIs causing a wide expected range. As such, RRI variability is examined for controlling transition from State 2 back to State 1 when State 2 was entered from the HV mode of State 1.

An increase in RRI variability may be detected at block 732 by comparing one or more of the most recent RRI differences between two consecutive beats to a mean of the most recent RRIs. If an average or other metric of the most recent RRI differences is greater than a predetermined percentage (e.g. approximately 20%) of the mean of the RRIs, an increase in RRI variability is detected at block 732.

If the RRI variability is increased, the current RRI is compared to the tachycardia expected RRI range at block 734. As described above, upon entering State 2, a tachycardia expected RRI range is initiated and updated on a beat by beat basis using the current RRI and a previous RRMEAN and RRMAD. If the current RRI is longer than the tachycardia expected RRI range (block 734), the detection algorithm transitions to the unconcerned State 1 (block 726) in response to the increased RRI variability and RRI outside (slower than) the tachycardia expected range.

If the criteria for switching back to State 1 when State 2 was entered from the HV mode are not met at blocks 732 and 734, the switchback counter is decreased at block 708. The slow beat counter is decreased at block 710. The switchback and slow beat counters are decreased in response to the current RRI being equal to or shorter than the detection lower limit interval, indicating the current rhythm remains a concerning rhythm.

In summary, evidence of RRIs that are consistently longer than the detection lower limit, within or longer than an expected RRI range for a normal rhythm, longer than a tachycardia expected range, low accumulated VT evidence, and/or increased RRI variability during State 2, or any combination thereof may be used to control the transition from the concerned State 2 to the unconcerned State 1.

Referring again to block 704, if the VT evidence reaches a detection threshold, for example if the VT evidence count reaches 6 or another predefined detection threshold, a transition to the convinced State 3 (block 740) occurs. Additionally, when both the FF and NF HR estimates exceed an SVT rate limit and both the FF and NF EGM signals are classified as treatable based on the noise/artifact rejection analysis, a transition to State 3 at block 740 may occur regardless of the VT evidence count.

During State 3, a therapy selection process is executed at block 742 to determine what therapy, if any, should be delivered in response to the detected VT. VT evidence accumulation continues at block 744 in the same manner as in State 2. Depending on the therapy decision process and therapy selected, there may be a time delay between entering State 3 and the onset of therapy delivery. During that time, VT evidence accumulation continues so that a spontaneous termination of the detected VT or a pause in the rhythm may be recognized.

The VT evidence counter is compared to a termination threshold at block 746, which is defined to be a value less than the detection threshold. In one embodiment, the detection threshold is 6 and the termination threshold is 2. If the VT evidence counter reaches the termination threshold, and either the NF or FF HR falls below a SVT rate limit (block 748), the detection algorithm may transition from State 3 back to State 2. The termination threshold is not to be interpreted as a threshold for detecting a tachycardia episode termination but rather a threshold for detecting a need to transition to a lower detection state.

Before transitioning to State 2 from State 3, the slow beat counter may be adjusted and examined to determine if a transition directly from State 3 back to State 1 is warranted. If the current RRI is longer than the detection lower limit interval (block 752), the slow beat counter is increased at block 756. The slow beat count is compared to a state change threshold at block 758. If the slow beat counter reaches a State 1 change threshold, a transition directly to State 1 occurs (block 726). The combined information of low VT evidence (block 746), the current RRI longer than the detection lower limit interval (block 752), and consistent slow beats based on the slow beat count (block 758) warrants a transition to the unconcerned State 1.

If the State 1 change threshold has not been reached at block 758, the rhythm is still considered a concerning. The detection algorithm transitions back to State 2 at block 702.

On the other hand, if the current RRI is shorter than or equal to the detection lower limit at block 752, the slow beat counter is decreased at block 754. A transition back to the concerned State 2 is made based on the low VT evidence and the NF or FF HR being below an SVT rate limit but the current RRI still shorter than the detection lower limit interval. Additional monitoring is performed in State 2 before returning to State 1, or progressing again into State 3.

After a therapy decision has been made at block 742, the detection algorithm advances to State 4 (block 750) if the accumulated VT evidence remains above the termination threshold (negative result at block 746). In State 4, the therapy is delivered as scheduled at block 766. Upon therapy delivery, the VT evidence counter is cleared to a zero value at block 768.

When the therapy being delivered is a shock therapy, the FF EGM signal may be unreliable for several seconds. A FF unreliable timer may be set at block 770 to an interval of time to allow post-shock polarization artifact to diminish before the FF EGM signal is used again for tachycardia detection. Similarly, any time a shock pulse or any other therapy is delivered for therapeutic of diagnostic purposes, such as T-wave shocks for inducing VF, a FF unreliable timer may be set. The FF unreliable timer may be set, for example, to an interval of approximately 2 to 5 seconds. Similarly, if electrodes used in sensing the NF signal are used in delivering a therapy, such as a pacing therapy, an NF unreliable timer may be set to allow polarization artifact and/or any NF EGM morphology changes to dissipate before using the NF signal again for tachycardia detection.

A transition back to State 2 (block 702) immediately occurs following therapy delivery. The detection algorithm transitions to State 2 to allow continued monitoring of the rhythm. The rhythm immediately after therapy delivery is still considered a concerning rhythm since the therapy may have not been successful or a VT episode may be recurring. As such, monitoring of the heart rhythm in State 2 occurs after delivering a therapy before returning to State 1 (or State 3 in the case of a redetected, recurring or worsening VT).

Figure 21:
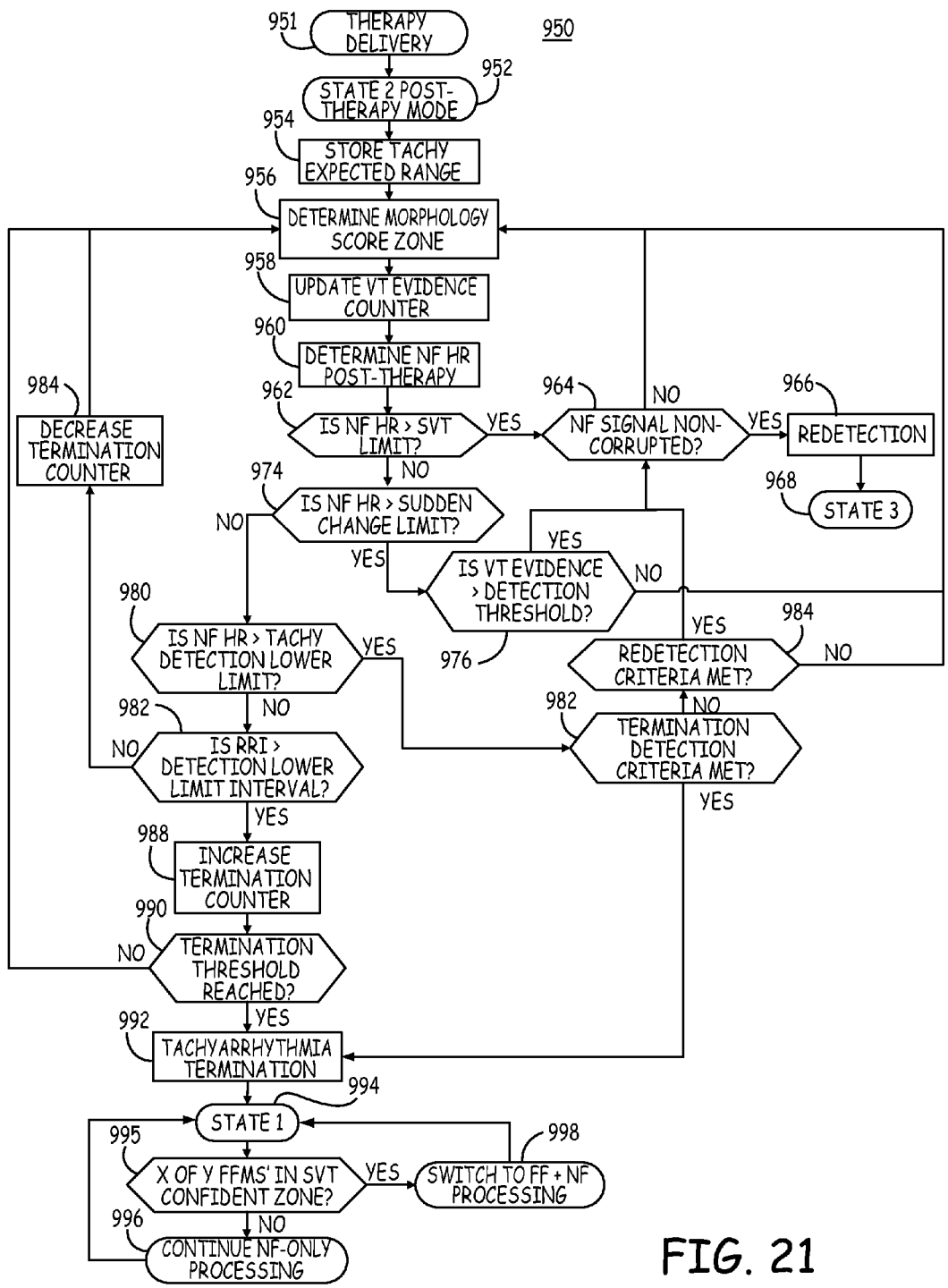
FIG. 21 is a flow chart of a post-therapy mode of operation performed upon re-entering State 2 after delivering a tachycardia therapy.

FIG. 21 is a flow chart 950 of a post-therapy mode of operation performed upon re-entering State 2 after delivering a therapy. In some embodiments, after delivering a therapy, the detection algorithm may operate differently than the pre-therapy State 2 and State 3 operations. Unique criteria for redetection of the VT episode and criteria for detecting termination of the VT episode after delivering a therapy may be applied during a post-therapy mode of operation in State 2.

At block 951, a therapy is delivered in State 4 and a transition is made back to State 2 into a post-therapy mode of operation (block 952). Upon entering State 4, the tachycardia expected range is no longer updated. The last computed tachycardia expected range prior to therapy delivery is stored at block 954 for use in applying criteria for redetecting the tachycardia as will be further described below. In some embodiments, only the mean RRI used in setting the tachycardia expected range is stored at block 954 as threshold RRI for use in redetecting tachycardia.

As described in conjunction with FIG. 20, a FF EGM unreliable timer may be set when the delivered therapy is a shock therapy such that the FF EGM signal is not used, at least initially, during the post-therapy mode of operation. Instead, the NF EGM signal is used for sensing cardiac events for determining RRIs, setting a morphology analysis window and for determining an overall morphology score and corresponding morphology score zone for adjusting the VT evidence counter post-therapy. If the delivered therapy is a pacing therapy, i.e. anti-tachycardia pacing (ATP) therapy, the FF EGM signal may continue to be used for determining an overall morphology score. As such, during the post-therapy mode, different signal processing methods may be used depending on the type of therapy that was delivered.

At block 956, an overall morphology score is determined from the FF EGM signal (post-ATP) or the NF EGM signal (post-shock) based on an analysis window set for the current NF sensed event on a beat-by-beat basis. Each morphology score is classified according to the morphology matching zones as described previously. The VT evidence counter is updated at block 958 based on the morphology score zone.

In some embodiments, specific beat feature rules are not applied during the post-therapy mode when the delivered therapy is a shock therapy. In particular, any rules relying on features determined from the FF EGM are not applied post-shock, at least not until the FF unreliable timer is expired or until a normal "pre-therapy" operating mode is re-entered after detecting termination. The VT evidence counter is adjusted based only on the NFMS zone post-shock.

Alternatively, a limited number of beat feature rules are applied post-shock. In one embodiment, a normal beat rule, analogous to the FF normal beat rule described in conjunction with FIG. 13C above, is the only zone-specific rule that is applied post-shock before adjusting the VT evidence counter. The normal beat rule may be applied using only specific NF beat features, or using FF beat features after a FF unreliable timer expires, when the overall morphology score falls into the VT gray zone. If the normal beat rule is true, the VT evidence counter may be decreased instead of being increased in response to the overall morphology score being in the VT gray zone (or increased but by a smaller increment than when the normal beat rule is false).

Additionally or alternatively, a rule analogous to the rhythm breaking point rule described previously may be applied across one or more morphology zones during the post-therapy mode of operation. For example, if a long NF RRI is detected, and the morphology score ending the long RRI falls into the SVT confident zone, or is greater than another rhythm breaking point detection threshold, a rhythm breaking point may be detected. If a rhythm breaking point is detected, the VT evidence counter is cleared at block 958. Similarly, if two consecutive morphology scores are in the SVT confident zone, the VT evidence counter may be cleared at block 958.

After adjusting the VT evidence counter, the post therapy NF HR is estimated at block 960. The NF HR may be estimated, as described above, based on the nth shortest RRI out of a predetermined number of most recent RRIs occurring after the therapy delivery. The earliest post-therapy NF HR estimate can be determined starting with the nth available beat. For example, if the ninth shortest RRI out of the most recent 12 RRIs is to be used as a HR estimate, the shortest RRI identified after 9 RRIs following the therapy is the first NF HR estimate. Updating of the VT evidence counter can begin on a beat-by-beat basis prior to the nth post-therapy RRI.

The criteria for redetection and/or termination detection applied during the post-therapy mode of operation are dependent on the NF HR estimate. As such, the NF HR estimate is compared to an SVT rate limit at block 962. If the NF HR is faster than the SVT limit, and the NF signal is not corrupted (block 964), the tachycardia episode is redetected at block 966 in response to the high HR. A transition to the convinced State 3 occurs at block 968. If the post-therapy mode was entered after ATP therapy, the FF EGM signal may be used for verifying a NF HR estimate as described above. If the FF EGM signal is being used during the post-therapy mode, e.g., post-ATP, the FF signal may also be verified as being non-corrupted at block 964 before transitioning to State 3.

The detection algorithm continues to update the VT evidence counter on a beat-by-beat basis during State 3 at block 968 according to the post-therapy operation mode while making a therapy selection. The NF HR estimate is also updated during State 3 for detecting termination of the tachycardia episode during State 3. Thus, during the post-therapy operation of State 3, a transition directly back to State 1 may occur if termination criteria e.g. consistent RRIs longer than the detection lower limit interval, are met before a therapy decision is made and therapy delivery is ready.

Referring again to block 962, if the NF HR estimate is less than the SVT limit, but is greater than the sudden change limit, as determined at block 974, the VT evidence counter is compared to the detection threshold at block 976. The tachycardia episode is redetected at block 966 if the VT evidence counter is greater than the detection threshold (block 976) and the NF signal (and FF signal post-ATP) is not corrupted (block 964).

Termination of the tachycardia episode cannot be detected if the NF HR is greater than the sudden change limit. The detection algorithm will remain in the concerned State 2 (or State 3). As such, when the NF HR is greater than the SVT limit (block 962), or less than the SVT limit but greater than the sudden change limit (block 974), redetection criteria are applied at blocks 976 and/or 964, but termination detection criteria are not applied. If redetection criteria are not met (negative branches of blocks 976 and 964), the process returns to block 956 to sense the next cardiac event and determine the next overall morphology score zone, update the VT evidence counter and update the estimated NF HR.

In order for the redetection criteria to be met when the NF HR is greater than the SVT limit or greater than the sudden change limit, the NF signal (and FF signal when being relied upon for adjusting VT evidence) should be non-corrupted. The NF and FF signals may be determined to be corrupted or non-corrupted at block 964 according to the status of a "treatable rhythm" flag as described in conjunction with FIG. 19.

If the NF HR estimate is less than the sudden change limit (negative result at block 974), but greater than the tachycardia detection lower limit (block 980), both termination detection criteria and redetection criteria are applied. At block 982, termination detection criteria may include a comparison of the current RRI to a detection lower limit interval. Termination detection may also require that the detection algorithm has been operating in State 2 or State 3 for a total of at least n seconds, for example approximately 3 seconds, to avoid frequent state transitions. In response to termination detection criteria being satisfied at block 982 for the current RRI, a termination counter is increased at block 988.

Figure 22:
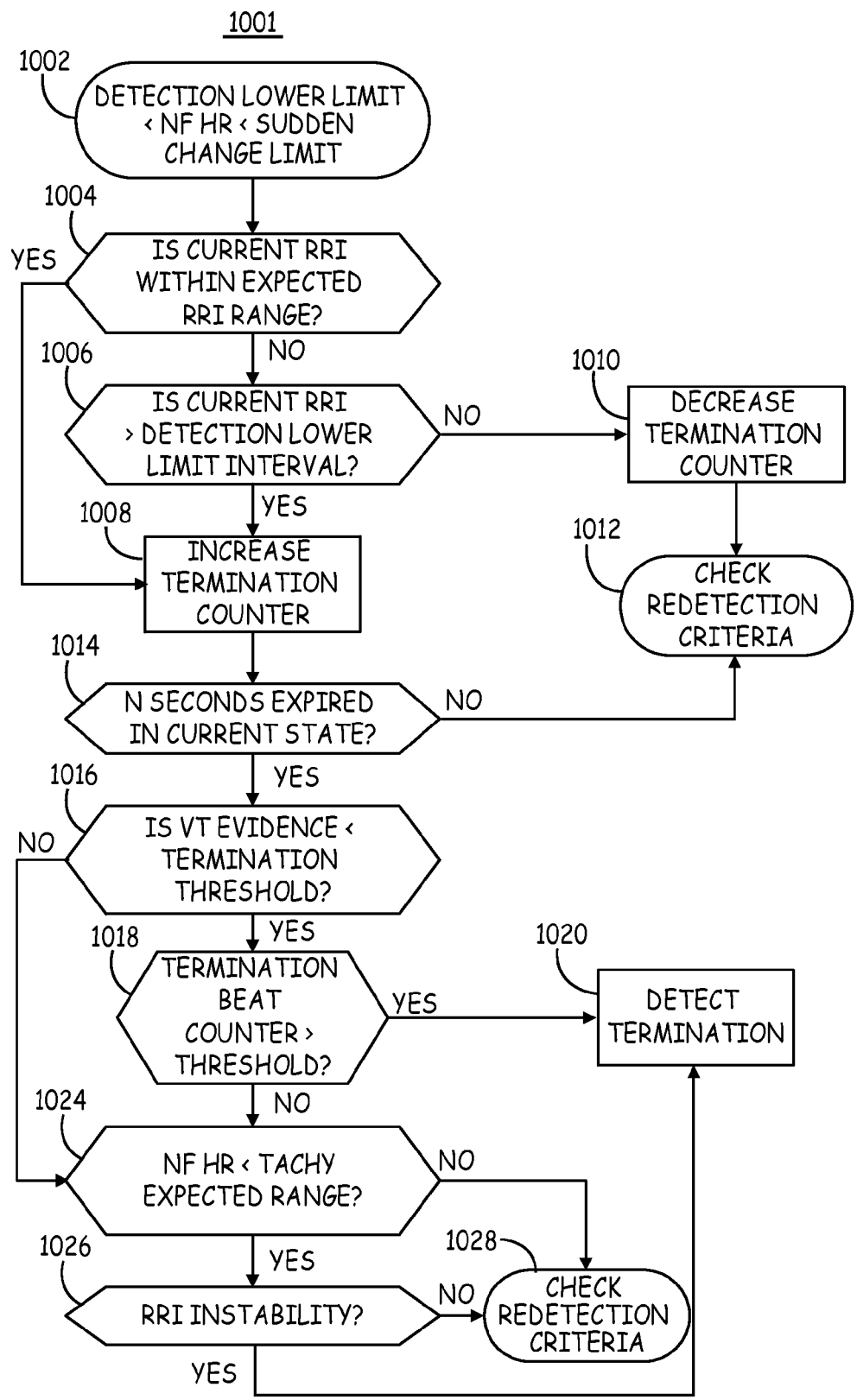
FIG. 22 is a flow chart of one method for detecting post-therapy VT termination according to one embodiment.

FIG. 22 is a flow chart 1001 of one method for detecting post-therapy VT termination according to one embodiment. The method shown in FIG. 22 may correspond to operations performed at block 982 of FIG. 21 for applying termination detection criteria. When the NF HR estimate is less than the sudden change limit (block 1002), but greater than the detection lower limit, termination criteria are applied by comparing the current RRI to the normal expected RRI range at block 1004. The normal expected RRI range is the final expected RRI range stored upon transitioning from the unconcerned State 1 to concerned State 2 prior to the VT episode detection. If the current RRI is within (or longer than) the normal expected range at block 1004, a termination beat counter is increased at block 1008.

If the current RRI is not within or longer than the normal RRI range, the current RRI may alternatively be compared to the detection lower limit interval at block 1006. If State 1 was exited during the HV mode of operation, a normal expected RRI range may not be stored. In this case, the threshold of the detection lower limit interval may be used at block 1006 instead of a comparison to the expected RRI range at block 1004.

If the current RRI is greater than at least one of the last stored expected RRI range or the detection lower limit interval, the termination beat counter is increased at block 1008. If neither of the conditions tested at blocks 1004 and 1006 are met, the termination beat counter is decreased at block 1010.

The termination beat counter may be increased by one or another increment each time the current RRI is in or longer than the last stored expected RRI range or longer than the detection lower limit interval. The termination beat counter may be decreased by two or another decrement each time the current RRI is shorter than the normal expected RRI range or the detection lower limit interval.

If the termination counter is increased at block 1008, and at least n seconds have expired while operating in the current detection algorithm state (State 2 or State 3), as determined at block 1014, additional termination criteria are applied. If the detection algorithm has not been operating in the current state for at least n seconds, for example approximately 3 seconds, termination will not be detected. The required time interval for operating within the current state may be applied at block 1014 to prevent frequent state transitions. The algorithm may proceed to apply redetection criteria at block 1012 when termination criteria are not met. Referring briefly to FIG. 21, when termination criteria are not met at block 982, the process advances to block 984 of FIG. 21 to apply redetection criteria.

In FIG. 22, if the required time interval in the current state has expired at block 1014, the VT evidence counter is compared to a termination threshold at block 1016. If the VT evidence counter has fallen below a selected threshold for VT evidence, the termination beat counter is compared to termination beat threshold at block 1018. If the termination beat counter has reached a threshold count, termination is detected at block 1020. Termination is detected in response to the low VT evidence and the RRIs being consistently within or longer than the expected RRI range or longer than the detection lower limit interval.

If the VT evidence counter or the termination beat counter does not meet a respective termination detection threshold, additional termination criteria may be applied at blocks 1024 and 1026. The current NF HR estimate is compared to the HR corresponding to the last stored tachycardia expected range at block 1024. In one embodiment, if the nth shortest RRI out of the most recent m post-therapy RRIs is at least 50 ms longer than the tachycardia expected range at block 1024, termination may still be detected if a pattern of variable RRIs is detected at block 1026. A serious VT can be characterized by RRIs that are highly regular or stable in length. As such, termination detection criteria can include a criterion related to detecting instable RRIs as an indication of a return to a non-pathological rhythm.

In one embodiment, the cumulative sum of consecutive RRI differences for a selected number of the most recent post-therapy RRIs is compared to a percentage of the mean of the same RRIs. For example, if the cumulative sum of the RRI differences is greater than at least approximately 10% of the mean RRI, the RRIs are considered instable, an indication of a non-treatable rhythm.

This RRI instability combined with a HR less than the tachycardia expected range is considered evidence that the VT has been terminated successfully by the delivered therapy. Termination is detected at block 1020. If the criteria applied at blocks 1024 and 1026 for detecting VT termination are not met, the algorithm applies redetection criteria at block 1028.

Referring to FIG. 21, when the termination detection criteria are met at block 982, termination is detected at block 992, and a transition to unconcerned State 1 occurs at block 994. If termination detection criteria are not met at block 982, the detection algorithm advances to block 984 to apply redetection criteria.

Figure 23:
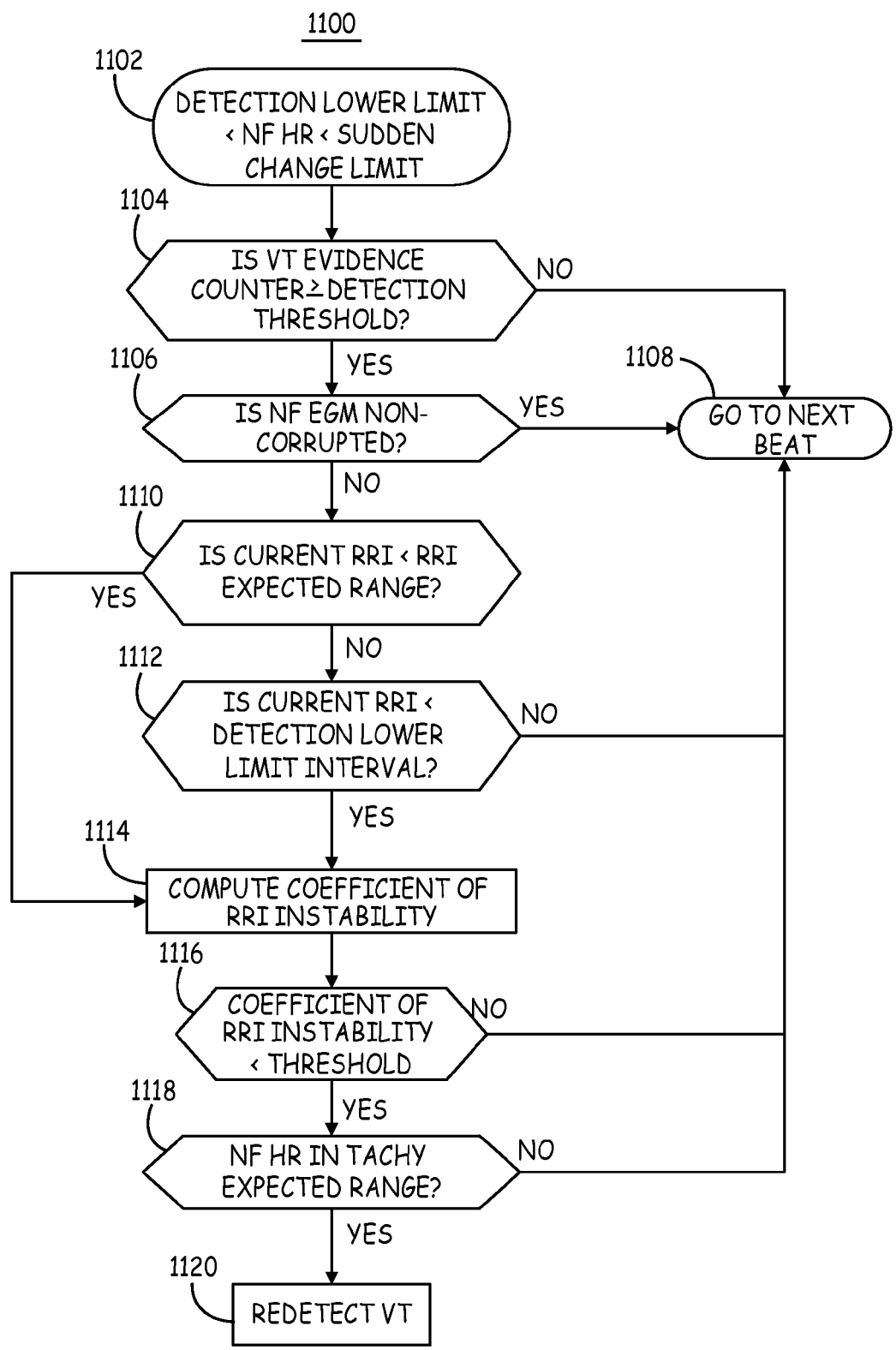
FIG. 23 is a flow chart of one method for redetecting VT during a post therapy mode of operation.

FIG. 23 is a flow chart 1100 of one method for redetecting VT during a post therapy mode of operation when the NF HR is greater than the tachycardia detection lower limit but less than the sudden change limit (block 1102). This method for redetection of a VT may be applied at block 984 of FIG. 21.

At block 1104, the VT evidence counter is compared to a detection threshold. If the detection threshold has not been reached, redetection does not occur on the current beat. The algorithm advances to the next beat at block 1108. If the VT evidence counter is equal to or greater than the detection threshold, but the NF EGM signal (or FF EGM signal post-ATP) is corrupted (negative branch of block 1106), redetection criteria are not met for the current beat. Corruption of the NF EGM signal may be identified based on the status of the "treatable rhythm" flag as described in conjunction with FIG. 18. Referring briefly to FIG. 21, the algorithm advances to the next beat by returning to block 956 to determine the next NFMS and NF HR estimate for applying redetection and/or termination criteria according to the next NF HR estimate as appropriate.

In FIG. 23, when the VT evidence counter has reached a detection threshold at block 1104 and the NF EGM signal is non-corrupted at block 1106, the current RRI is compared to the last stored expected RRI range at block 1110 and/or the detection lower limit interval at block 1112. When State 1 was exited during the LV mode of operation, an expected RRI range is stored for use in the comparison at block 1110. If State 1 was exited during the HV mode, the detection lower limit interval is used as a threshold for the comparison at block 1112 for redetection. If the current RRI is not shorter than the normal expected RRI range or the interval corresponding to the tachycardia detection lower limit, the VT is not redetected on the current beat. The detection algorithm advances to the next beat at block 1108.

If the current RRI is shorter than the normal expected range and/or shorter than the tachycardia detection lower limit interval, a coefficient of RRI instability is computed at block 1114. The coefficient of RRI instability is computed as a metric of the difference between the current RRI and a selected number of preceding post-therapy RRIs. The RRI stability metric computed for detecting termination as described in conjunction with FIG. 22 is based on consecutive RRI differences and is not dependent on trend in HR. The coefficient of RRI instability is computed using non-consecutive RRI differences and is sensitive to a trend in heart rate.

In one embodiment, a coefficient of RRI instability is computed as the cumulative sum of the absolute difference between the current RRI and each of the "a-1" most recent post-therapy RRIs divided by the mean of the "a" RRIs. This coefficient of RRI instability is compared to a threshold at block 1116. In one embodiment, the threshold applied to the coefficient of RRI instability is approximately 0.6. If the coefficient of RRI instability is greater than a redetection threshold at block 1116, redetection does not occur on the current beat and the algorithm advances to the next beat at block 1108.

If the ratio of the sum of absolute RRI differences to the mean of the RRIs is less than a threshold, the RRIs are considered highly stable and an indicator of a possibly serious VT. VT is redetected at block 1120 in response to the VT evidence remaining above a detection threshold, the NF EGM signal being non-corrupted, the current RRI being shorter than an RRI expected range or detection lower limit interval, and highly stable RRIs. In some embodiments, an additional requirement of the NF HR falling within than the last stored tachycardia expected range, must be satisfied at block 1118 in order to redetect the VT at block 1120.

Referring again to FIG. 21, if redetection criteria are met at block 984, and the NF signal is not corrupted (block 964), VT is redetected and a transition to convinced State 3 occurs at block 968.

The final HR condition used for selecting redetection/termination criteria during the post-therapy mode is a NF HR that is less than the tachycardia detection lower rate limit (negative branch of block 980). In this case, the current RRI is compared to the detection lower limit interval at block 982. If the current RRI is not less than the detection lower limit interval, a termination beat counter may be decreased (or kept at a zero count) at block 984. The process advances to the next beat by returning to block 956.

When the current RRI is greater than the detection lower limit interval, at block 982, the termination beat counter is increased at block 988 for the current beat. The termination beat counter is then compared to a threshold for detecting termination at block 990. If the termination beat threshold has not been reached, termination is not detected for the current beat. The process advances to the next beat by returning to block 956.

If the termination beat counter has reached a threshold for detecting termination at block 990, termination is detected at block 992. The VT has been successfully terminated by the delivered therapy. A transition back to state 1 occurs at block 994. A termination threshold applied to a termination beat counter may set to approximately 5 or another selected number such that termination may be detected in as few as the threshold number of beats post-therapy when each successive RRI is longer than the detection lower limit interval. In some embodiments, a fixed number of RRIs immediately following the therapy delivery, for example 2 to 3 post-therapy RRIs, may be ignored for the purposes of redetection and/or termination detection.

When the post-therapy mode is entered after shock delivery, various methods may be used to control when use of the FF EGM signal is restored. Recall that the post-therapy operating mode relies only upon the NF EGM signal when a shock has been delivered. The FF EGM signal may not return to a baseline, pre-therapy morphology for several seconds or even one or more minutes after delivering a shock therapy. A return to combined FF and NF signal processing which employs both signals for controlling state transitions may occur automatically upon detecting termination.

In other embodiments, the restoration of FF EGM signal processing may be independent of whether termination/redetection has occurred. In some embodiments, a fixed amount of time may be defined for ignoring the FF EGM signal. In this case, the NF EGM signal is used during the post-therapy mode until the timer expires. Upon expiration of the timer, combined FF and NF EGM signal processing is resumed. Timer expiration may occur before or after redetection or termination is detected and corresponding state transition. Restoration of combined FF and NF EGM signal processing is not necessarily dependent, therefore, on the detection algorithm state. In another embodiment, FF EGM signal processing may be restored when either termination is detected or a timer expires, whichever occurs first, or both may be required.

Alternatively, further analysis of the FF EGM signal at block 995 is performed to control when dual EGM signal processing is restored. Criteria may be applied to the FF EGM signal for determining when to use the FF EGM signal again. For example, the restoration of FF EGM signal analysis in addition to the NF EGM signal analysis may require a certain number of beats having a FFMS falling into the SVT confident zone as determined at block 995. Other criteria may be used for determining that the FF EGM signal has returned to pre-shock baseline morphology for controlling the transition from the post-shock NF-only signal processing to dual signal FF and NF EGM signal processing.

In one embodiment, after a FF unreliable timer expires after therapy delivery, the FFMS may be determined on a beat by beat basis for counting the number of beats having a normal or near normal morphology (e.g., FFMS falling into the SVT confident zone or whole SVT zone). When the FF EGM signal consistently demonstrates a normal or near-normal morphology, which may be tracked using a counter that is increased or decreased in response to the FFMS, restoration of FF signal processing mode may occur, regardless of the current detection algorithm state.

If termination is detected at block 990, resulting in a transition back to unconcerned State 1 at block 994, but the FF EGM signal has not returned to a baseline morphology (block 995), the detection algorithm may continue to operate using only the NF EGM signal (block 996). Only the NF EGM signal will be used to detect a sudden change in State 1. Once the FF EGM signal has returned to a baseline morphology, the detection algorithm returns to a "pre-therapy" operating mode which relies on both the NF and the FF EGM signal processing (block 998) for controlling state transitions.

It is to be understood that termination detection may not be required for restoring the FF EGM signal processing as shown in FIG. 21. If the FF EGM morphology is found to return to a baseline morphology while the detection algorithm remains in State 2 or State 3, the detection algorithm may begin using the FF EGM signal in addition to the NF EGM signal for applying beat feature rules, updating the VT evidence counter and controlling state transitions even before termination is detected.

In summary, in a pre-therapy mode, both FF and NF EGM signal processing occurs and detection algorithm criteria are applied to both the FF and NF signals for controlling the various state transitions. In a post-therapy mode, criteria for detecting termination (and transition from State 2 or State 3 to State 1) and criteria for redetection (transition from State 2 to State 3) are used which may be defined differently than the criteria used for controlling state transitions pre-therapy. Additionally, within the post-therapy mode, the signal processing methods used will depend on the type of therapy delivered. Post-ATP, both FF and NF signals may be used when applying termination and redetection criteria. Post-shock, however, only NF EGM signals are used until criteria are met for restoring the use of the FF EGM.

Once termination is detected and the FF EGM signal processing has been restored, the detection algorithm can be said to be operating in a pre-therapy mode again. If termination is not detected after a therapy, the detection algorithm may remain in the post-therapy mode, potentially redetecting and delivering another therapy one or more times, until termination criteria are met. Restoration of FF EGM signal processing may occur at any time during the post-therapy mode when a FF unreliable timer expires, morphology criteria are met, or other required conditions are met. If termination is detected but criteria for restoring the FF EGM signal are not met, only NF EGM signal processing continues but the various "pre-therapy" criteria and rules for controlling state transitions are used again by the detection algorithm rather than the post-therapy termination and redetection criteria. The detection algorithm returns to a full "pre-therapy" mode of operating once both termination is detected and FF EGM signal processing is restored.

Thus, a method and apparatus for detecting tachycardia have been presented in the foregoing description with reference to specific embodiments. It is appreciated that various modifications to the referenced embodiments may be made without departing from the scope of the disclosure as set forth in the following claims.

The invention claimed is:
1. A method, comprising:
sensing first cardiac events occurring in a heart chamber using a first cardiac electrode pair;
sensing second cardiac events occurring in the heart chamber using a second cardiac electrode pair;
estimating a first heart rate using the first cardiac events;
comparing the first heart rate to a heart rate threshold;
estimating a second heart rate using the second cardiac events in response to the first heart rate exceeding the heart rate threshold;
comparing the first heart rate and the second heart rate;

determining a patient heart rate exceeding the heart rate threshold in response to the second heart rate being within a predetermined matching range of the first heart rate;

determining the patient heart rate to be a lower one of the first heart rate and the second heart rate in response to the second heart rate not being within the predetermined matching range of the first heart rate;

determining whether the second cardiac events are unreliable; and setting the second heart rate equal to the first heart rate in response to the second cardiac events being unreliable.

2. The method of claim 1, wherein determining whether the second cardiac events are unreliable comprises detecting a threshold number of second cardiac events having a peak amplitude less than a reliable amplitude threshold.

3. The method of claim 1, wherein determining whether the second cardiac events are unreliable comprises detecting a threshold number of second cardiac events having a peak amplitude approximately equal to a cardiac event sensing threshold.

4. The method of claim 1, wherein determining whether the second cardiac events are unreliable comprises:
measuring an interval between a consecutive pair of the second cardiac events; and
comparing the interval to an unreliable interval threshold.

5. The method of claim 1, further comprising:
setting a counter to a maximum value in response to one of the second cardiac events being determined unreliable;
sensing a next second cardiac event;
determining if the next second cardiac event is unreliable; and
decreasing the counter in response to determining the next second cardiac event is reliable.

6. The method of claim 5, further comprising setting the second heart rate equal to the first heart rate as long as the counter has a value greater than zero.

7. The method of claim 1, wherein the first electrode pair comprises a first electrode and a second electrode and the second electrode pair comprises a third electrode and a fourth electrode, each of the third electrode and the forth electrode being different than the first electrode and the second electrode.

8. The method of claim 1, wherein the threshold heart rate corresponds to a tachycardia detection limit, the method further comprising detecting a concerning heart rhythm in response to the patient heart rate being greater than the threshold heart rate.

9. The method of claim 1, further comprising storing data corresponding to the first cardiac events and the second cardiac events in response to the first heart rate and the second heart rate not matching within the predetermined matching range.

10. The method of claim 1, further comprising:
delivering a pacing pulse using the first electrode pair;
generating a second cardiac event in response to the pacing pulse; and
estimating the second heart rate in response to the generated second cardiac event.

11. The method of claim 10, further comprising:
setting a blanking period in response to the pacing pulse;
tracking an amplitude of an evoked response to the pacing pulse using the second electrode pair; and
setting a cardiac event sensing threshold to a percentage of a peak amplitude tracked during the blanking period.

12. A medical device for monitoring a patient's heart rhythm, comprising:

a first cardiac electrode pair to sense first cardiac events occurring in a heart chamber;

a second cardiac electrode pair to sense second cardiac events occurring in the heart chamber; and a heart rate detector configured to estimate a first heart rate using the first cardiac events, compare the first heart rate to a heart rate threshold, estimate a second heart rate using the second cardiac events in response to the first heart rate exceeding the heart rate threshold, compare the first heart rate and the second heart rate, determine a patient heart rate exceeding the heart rate threshold in response to the second heart rate being within a predetermined matching range of the first heart rate, determine the patient heart rate to be a lower one of the first heart rate and the second heart rate in response to the second heart rate not being within the predetermined matching range of the first heart rate, determine whether the second cardiac events are unreliable, and set the second heart rate equal to the first heart rate in response to the second cardiac events being unreliable.

13. The device of claim 12, wherein determining whether the second cardiac events are unreliable comprises detecting a threshold number of second cardiac events having a peak amplitude less than a reliable amplitude threshold.

14. The device of claim 12, wherein determining whether the second cardiac events are unreliable comprises detecting a threshold number of second cardiac events having a peak amplitude approximately equal to a cardiac event sensing threshold.

15. The device of claim 12, wherein determining whether the second cardiac events are unreliable comprises:
measuring an interval between a consecutive pair of the second cardiac events; and
comparing the interval to an unreliable interval threshold.

16. The device of claim 12, wherein the heart rate detector is further configured to set a counter to a maximum value in response to one of the second cardiac events being determined unreliable, sense a next second cardiac event, determine if the next second cardiac event is unreliable, and decrease the counter in response to determining the next second cardiac event is reliable.

17. The device of claim 16, wherein the heart rate detector is further configured to set the second heart rate equal to the first heart rate as long as the counter has a value greater than zero.

18. The device of claim 12, wherein the first electrode pair comprises a first electrode and a second electrode and the second electrode pair comprises a third electrode and a fourth electrode, each of the third electrode and the forth electrode being different than the first electrode and the second electrode.

19. The device of claim 12, wherein the threshold heart rate corresponds to a tachycardia detection limit, and wherein the heart rate detector is further configured to detect a concerning heart rhythm in response to the patient heart rate being greater than the threshold heart rate.

20. The device of claim 12, further comprising a memory to store data corresponding to the first cardiac events and the second cardiac events in response to the first heart rate and the second heart rate not matching within a predetermined threshold.

21. The device of claim 12, further comprising a pulse generator to deliver a pacing pulse using the first electrode pair, wherein the heart rate detector is further configured to generate a second cardiac event in response to the pacing pulse and to use the generated second cardiac event to estimate the second heart rate.

22. The device of claim 21, wherein the heart rate detector is further configured to set a blanking period in response to the pacing pulse, track an amplitude of an evoked response to the pacing pulse using the second electrode pair, and set a cardiac event sensing threshold to a percentage of a peak amplitude tracked during the blanking period.

23. A non-transitory computer-readable medium storing a set of instructions for monitoring a patient's heart rhythm, which when implemented in a processor of a medical device causes the device to:
sense first cardiac events in a heart chamber using a first cardiac electrode pair;
sense second cardiac events in the heart chamber using a second cardiac electrode pair;
estimate a first heart rate using the first cardiac events;
compare the first heart rate to a heart rate threshold;
estimate a second heart rate using the second cardiac events in response to the first heart rate exceeding the heart rate threshold;
compare the first heart rate and the second heart rate;
determine a patient heart rate exceeding the heart rate threshold in response to the second heart rate being within a predetermined matching range of the first heart rate;
determine the patient heart rate to be a lower one of the first heart rate and the second heart rate in response to the second heart rate not being within the predetermined matching threshold of the first heart rate;
determining whether the second cardiac events are unreliable; and
setting the second heart rate equal to the first heart rate in response to the second cardiac events being unreliable.

* * * * *